US009181540B2

(12) United States Patent
Tabuchi et al.

(10) Patent No.: US 9,181,540 B2
(45) Date of Patent: *Nov. 10, 2015

(54) METHOD FOR PRODUCTION OF POLYPEPTIDE

(71) Applicant: Chugai Seiyaku Kabushiki Kaisha, Kita-ku, Tokyo (JP)

(72) Inventors: Hisahiro Tabuchi, Tokyo (JP); Satoshi Tainaka, Tokyo (JP); Tomoya Sugiyama, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/449,259

(22) Filed: Aug. 1, 2014

(65) Prior Publication Data

US 2014/0335565 A1 Nov. 13, 2014

Related U.S. Application Data

(63) Continuation of application No. 13/368,945, filed on Feb. 8, 2012, now Pat. No. 8,796,007, which is a continuation of application No. 12/450,161, filed as application No. PCT/JP2008/054579 on Mar. 13, 2008, now abandoned.

(30) Foreign Application Priority Data

Mar. 15, 2007 (JP) ................................ 2007-066172

(51) Int. Cl.

| | |
|---|---|
| ***C12N 9/88*** | (2006.01) |
| ***C12N 15/00*** | (2006.01) |
| ***C12N 1/20*** | (2006.01) |
| ***C07H 21/04*** | (2006.01) |
| ***C12P 21/00*** | (2006.01) |
| ***C12P 21/02*** | (2006.01) |
| ***C07K 16/00*** | (2006.01) |

(52) U.S. Cl.

CPC . *C12N 9/88* (2013.01); *C07K 16/00* (2013.01); *C12P 21/00* (2013.01); *C12P 21/02* (2013.01); *C12Y 401/01029* (2013.01)

(58) Field of Classification Search

CPC .................................................... C12N 9/2402
USPC .................................. 435/252.3, 320.1, 69.1
See application file for complete search history.

(56) References Cited

U.S. PATENT DOCUMENTS

| | | | |
|---|---|---|---|
| 5,658,786 | A | 8/1997 | Smith et al. |
| 6,184,007 | B1 | 2/2001 | Dusch et al. |
| 6,225,115 | B1 | 5/2001 | Smith et al. |
| 6,251,613 | B1 | 6/2001 | Kishimoto et al. |
| 6,316,238 | B1 | 11/2001 | Nakamura et al. |
| 6,812,339 | B1 | 11/2004 | Venter et al. |
| 7,413,536 | B1 | 8/2008 | Dower et al. |
| 7,919,086 | B2 | 4/2011 | Nakano et al. |
| 2003/0165495 | A1 | 9/2003 | Carulli et al. |
| 2005/0221466 | A1 | 10/2005 | Liao et al. |
| 2005/0265983 | A1 | 12/2005 | Melamed et al. |
| 2006/0014937 | A1 | 1/2006 | Kang et al. |
| 2007/0162995 | A1 | 7/2007 | Good et al. |
| 2007/0166362 | A1 | 7/2007 | Sakuma et al. |
| 2007/0190599 | A1 | 8/2007 | Nakano et al. |
| 2009/0191591 | A1 | 7/2009 | Tabuchi et al. |
| 2009/0221442 | A1 | 9/2009 | Dower et al. |
| 2010/0167346 | A1 | 7/2010 | Tabuchi et al. |
| 2010/0233759 | A1 | 9/2010 | Tabuchi et al. |
| 2010/0248359 | A1 | 9/2010 | Nakano et al. |
| 2011/0003334 | A1 | 1/2011 | Tabuchi et al. |
| 2011/0014654 | A1 | 1/2011 | Tabuchi et al. |
| 2012/0045795 | A1 | 2/2012 | Tabuchi et al. |

FOREIGN PATENT DOCUMENTS

| | | | |
|---|---|---|---|
| CN | 1612689 | A | 5/2005 |
| CN | 1838969 | A | 9/2006 |
| EP | 1 212 619 | B1 | 5/2007 |
| EP | 2 213 746 | A1 | 8/2010 |
| JP | 08-191693 | A | 7/1996 |
| JP | 10-075787 | A | 3/1998 |
| JP | 10-191984 | A | 7/1998 |
| JP | 2000-228990 | A | 8/2000 |
| JP | 2005-525100 | A | 8/2005 |
| JP | 2006-506086 | A | 2/2006 |
| WO | WO-92/04381 | A1 | 3/1992 |
| WO | WO 97/27485 | A1 | 7/1997 |
| WO | WO-01/20331 | A1 | 3/2001 |
| WO | WO-02/092768 | A2 | 11/2002 |
| WO | WO-03/039485 | A2 | 5/2003 |
| WO | WO-2005/076015 | A1 | 8/2005 |
| WO | WO-2006/006693 | A1 | 1/2006 |
| WO | WO-2006/119115 | A2 | 11/2006 |
| WO | WO-2007/056507 | A1 | 5/2007 |
| WO | WO 2007/119774 | A1 | 10/2007 |
| WO | WO-2008/114673 | A1 | 9/2008 |
| WO | WO-2009/020144 | A1 | 2/2009 |
| WO | WO-2009/051109 | A1 | 4/2009 |
| WO | WO-2009/054433 | A1 | 4/2009 |

OTHER PUBLICATIONS

Han et al., "Mechanisms of regulation of taurine transporter activity," Taurine 6, Edited by Oja and Saransaari, 2006, 79-90.

(Continued)

*Primary Examiner* — Maryam Monshipouri
(74) *Attorney, Agent, or Firm* — Foley & Lardner LLP

(57) ABSTRACT

The present invention provides a method capable of producing a natural or recombinant protein in high yield. The present invention relates to a method of producing a polypeptide, comprising culturing a cell which strongly expresses cysteine sulfinic acid decarboxylase and has a transferred DNA encoding a desired polypeptide and thereby allowing the cell to produce the polypeptide. Hamster cysteine sulfinic acid decarboxylase, a DNA encoding the same, a recombinant vector and a transformed cell are also provided.

12 Claims, 26 Drawing Sheets

(56) References Cited

OTHER PUBLICATIONS

Herman et al., "Low dose methotrexate induces apoptosis with reactive oxygen species involvement in T lymphocytic cell lines to a greater extent than in monocytic lines," Inflammation Research, 2005, 54:273-280.
Alper, Seth L., "Moleclar physiology of SLC4 anion exchangers," Exp. Physiol., 2006, 91:153-161.
Arden et al., "Life and death in mammalian cell culture; strategies for apoptosis inhibition," Trends in Biotechnology, apr. 2004, 22(4):174-180.
Beckmann et al., "Coexpression of band 3 mutants and Rh polypeptides: diffrential effects of band 3 on the expression of the Rh complex containing D polypeptide and the Rh complex containing CcEe polypeptide," Blood, Apr. 15, 2001, 97(8):2496-2505.
Bell et al., "Genetic Engineering of Hybridoma Glutamine Metabolism," Enzyme and Microbial Technology, 1995, 17(2):98-106.
Butler, Michael, "Animal cell cultures: recent achievements and perspectives in the production of biopharmaceuticals," Appl. Microbiol. Biotechnol., Aug. 2005, 68(3):283-291.
Chambard et al., "Sugar transport by mammalian members of the SLC26 superfamilty of anion-bicarbinate exchangers," J. Physiol., 2003, 550:667-677.
Christensen et al., "High expression of the taurine transporter TauT in primary cilia of NIH3T3 fibroblasts," Cell Biology International, 2005, 29:347-351.
Christie et al., "The Adaptation of BHK Cells to a Non-Ammoniagenic Glutamate-Based Culture Medium," Biotechnology and Bioengineering, Aug. 5, 1999, 64(3):298-309.
Database DDBJ/EMBL/GenBank [online], Accession No. NM_000342, uploaded Sep. 25, 2007, Keskanokwong et al., Definition: *Homo sapiens* solute carrier family 4, anion exchanger, member 1 (erythrocyte membrane protein band 3, Diego blood group) (SLC4A1), mRNA, retrieved Nov. 11, 2008, 12 pages.
Database EMBL [Online] July 23, 1992, XP002593029, retrieved from EBI acdession No. EMBL:M95495, 3 pages.
Database Uniprot [Online] Jan. 10, 2006, XP002593032, retrieved from EBI accession No. UNIPROT:Q2VRP7, 1 page.
Database UniProt [Online] Jul.1, 1993, XP002593028, retrieved from EBI accession No. UNIPROT:Q00589, 2 pages.
Database UniProt [Online] Jun. 1, 2001, "RecName: Full=Cysteine sulfinic acid decarboxylase; EC=<A>; AltName: Full=Cysteine-sulfinate decarboxylase; AltName: full=Sulfinoalanine decarboxylase;" XP002597738 retreived from EBI accession No. UNIPROT:Q9DBE0 Database accession No. W9DBE0, one page.
Database Uniprot [Online] March 15, 2005, XP002593030, retreived from EBI accession No. UNIPROT:Q5F431, 1 page.
Database Uniprot [Online] Oct. 1, 2000, XP002593031, retreived from EBI accession No. UNIPROT:Q9MZ34, 2 pages.
de la Cruz Edmonds et al., "Development of Transffection and High-Producer Screening Protocols for the CHOK1SV Cell System," Molecular Biology, Oct. 1, 2006, 34(2):179-190.
de la Rosa et al., "Evidence for a Rate-Limiting Role of Cysteinesulfinate Decarboxylase Activity in Taurine Biosynthesis In Vivo," Comp. Biochem. Physiol., 1985, 81(3):565-571.
De La Rosa et al., "Evidence for a Rate-Limiting Role of Cysteinesulfinate Decarboxylase Activity in Taurine Biosynthesis In Vivo," Comp. Biochem. Physiol. B, 1985, 81(3):565-571.
Dusch et al., "Expression of the Corynebacterium glutamicum panD Gene Encoding L-Aspartate-α-Decarboxylase Leads to Pantothenate Overproduction in *Escherichia coli*," Applied and Environmental Microbiology, Apr. 1999, 65(4):1530-1539.
Final Office Action dated Dec. 17, 2010 in U.S. Appl. No. 12/226,195.
Final Office Action dated Mar. 1, 2012 in U.S. Appl. No. 12/733,052.
Final Office Action dated Mar. 2, 2012 in U.S. Appl. No. 12/734,283
Final Office Action dated Aug. 23, 2011 in U.S. Appl. No. 12/733,815.
Fu et al., "Direct interaction and cooperative role of tumor suppressor p16 with band 3 (AE1)," FEBS Letters, 2005, 579(10):2105-2110.
Ganapathy et al., "Expression and Regulation of the Taurine Transporter in Cultured Cell Lines of Human Origin," Advances in Experimental Medicine and Biology, 1994, 359:51-57, XP009123192.
GenBank Accession No. AEQ38544, Oct. 2011, 2 pages.
GenBank Accession No. EGW01898, Aug. 2011, 2 pages.
Good et al., "Engineering nitrogen use efficiency with alanine aminotransferase," Canadian Journal of Botany, Mar. 1, 2007, 85(3):252-262.
Griffith, Owen W., "Crysteinesulfinate Metabolism, Altered Partitioning Between Transamination and Decarboxylation Following Administration of β-Methyleneaspartate," J. Biol. Chem., Feb. 10, 1983, 258(3):1591-1598.
Hammer et al., "β-Alanine but not taurine can function as an organic osmolyte in preimplantation mouse embryos cultured from fertilized eggs," Molecular Reproduction and Development, Oct. 2003, 66(2):153-161.
Han et al., "Is TauT an Anti-Apoptotic Gene?" Taurine 6, Oja et al. Eds., 2006, 59-67.
Han et al., "Regulation of TauT by cisplatin in LLC-PK1 renal cells," Pediatr. Nephrol., 2005, 20:1067-1072.
Hwang et al., "Expression and purification of recombinant human angiopoietin-2 produced in Chinese hamster ovary cells," Protein Expression and Purification, 2005, 39:175-183.
Ifandi et al., "Regulation of Cell Proliferation and Apoptosis in CHO-K1 Cells by the Coexpression of c-Myc and Bcl-2," Biotechnol. Prog., 2005, 21:671-677.
International Search Report mailed Jun. 17, 2008, in corresponding PCT/JP2008/054579, 10 pages.
Ishiguro et al., "CO2 permeability and bicarbonate transport in microperfused interlobular ducts isolated from guinea-pig pancreas," Journal of Physiology, 2000, 528.2:305-315.
Ito et al., "Expression of taurine transporter is regulated through the TonE (tonicity-responsive element)/TonEBP (TonE-binding protein) pathway and contributes to cytoprotection in HepG2 cells," Biochem. J., 2004, 382:177-182.
Jhiang et al., "Cloning of the human taurine transporter and characterization of taurine uptake in thyroid cells," FEBS Letters, Mar. 1993, 318(2):139-144.
Kalwy et al., "Toward More Efficient Protein Expression," Molecular Biotechnology, Oct. 2006, 34(2):151-156.
Kennell et al,. "Principles and Practices of Nucleic Acid Hybridization," Prog. Nucleic Acid Res. Mol. Biol., 1971, 11:259-270.
Kim et al., "Response of recombinant Chinese hamster ovary cells to hyperosmotic pressure: effect of Bcl-2 overexpression," Journal of Biotechnology, 2002, 95:237-248.
Kim et al., "Characterization of Chimeric Antibody Producing CHO Cells in the Course of Dihydrofolate Reductase-Mediated Gene Amplification and Their Stability in the Absence of Selective Pressure," Biotechnology and Bioengineering, Apr. 5, 1998, 58(1):73-84.
Kondo et al., "Modulation of apoptosis by endogenous Bcl-xL expression in MKN-45 human gastric cancer cells," Oncogene, 1998, 17:2585-2591.
Lee et al., "Development of Apoptosis-Resistant Dihydrofolate Reductase-Deficient Chinese Hamster Ovary Cell Line," Biotechnol. Bioengineer., 2003, 82:872-876.
Liu et al., "Cloning and expression of a cDNA encoding the transporter of taurine and β-alanine in mouse brain," Proc. Natl. Acad. Sci. USA, Dec. 1992, 89(24):12145-12149.
Lux et al., "Cloning and characterization of band 3, the human erythrocyte anion-exchange protein (AE1)," Proc. Natl. Acad. Sci. USA, Dec. 1989, 86:9089-9093.
Miyasaka et al., "Characterization of Human Taurine Transporter Expressed in Insect Cells Using a Recombinant Baculovirus," Protein Expression and Purification, 2001, 23(3):389-397.
Morgan et al., "Interactions of transmembrane carbonic anhydrase, CAIX, with bicarbonate transporters," Am. J. Physiol. Cell Physiol., Aug. 2007, 293(2):C738-C748.
Mount et al., "The SLC26 gene family of multifunctional anion exchangers," Pflugers Arch.—Eur. J. Physiol., 2004, 447:710-721.
Ngo et al., "Computational Complexity, Protein Structure Prediction, and the Levinthal Paradox," The Protein Folding Problem and Tertiary Structure Prediction, Merz et al. (Eds.), 1994, 433 and 492-495.

(56) References Cited

OTHER PUBLICATIONS

Notice of Allowance dated Dec. 20, 2012 in U.S. Appl. No. 12/733,052.
Office Action dated Jan. 6, 2011 in U.S. Appl. No. 12/733,815.
Office Action dated Feb. 27, 2013 in U.S. Appl. No. 13/138,909.
Office Action dated May 12, 2011 in U.S. Appl. No. 12/733,052.
Office Action dated May 18, 2010 in U.S. Appl. No. 12/226,195.
Office Action dated Aug. 3, 2011 in U.S. Appl. No. 12/734,283.
Porter et al., "Non-steady-state kinetics of brain glutamate decarboxylase resulting from interconversion of the apo- and holoenzyme," Biochimica et Biophysica Acta, 1988, 874:235-244.
Pushkin et al., "SLC4 base (HCO-3, CO-23) transporters: classification, function, structure, genetic diseases, and knockout models," Am. J. Physiol. Renal Physiol., 2006, 290:F580-F599.
Ramamoorthy et al., "Functional characterization and chromosomal localization of a cloned taurine transporter from human placenta," Biochem. J., 1994, 300:893-900.
Reymond et al., "Molecular cloning and sequence analysis of the cDNA encoding rat liver cysteine sulfinate decarboxylase (CDS)," Biochimica et Biophysica Acta, 1996, 1307:152-156.
Rudinger, J., "Characteristics of the amino acids as components of a peptide hormone sequence," Peptide Hormones, Parsons (Ed.), 1976, 1-7.
Shen et al., "Expression of Anion Exchanger 1 Sequestrates p16 in the Cytoplasm in Gastric and Colonic Adenocarcinoma," Neoplasia, Oct. 2007, 9(10):812-819.
Shibayama et al., "Effect of Methotrexate Treatment on Expression Levels of Organic Anion Transporter Polypeptide 2,P-Glycoprotein and Bile Salt Export Pump in Rats," Biol. Pharm. Bull., Mar. 2009, 32(3):493-496.
Smith et al., "Cloning and Expression of a High Affinity Taurine Transporter from Rat Brain," Molecular Pharmacology, 1992, 42(4):563-569.
Supplementary European Search Report dated Sep. 13, 2010, in EP 08738650.4, 9 pages.
Tabuchi et al., "Overexpression of Taurine Transporter in Chinese Hamster Ovary cells Can Enhance Cell Viability and Product Yield, While Promoting Glutamine Consumption," Biotechnology and Bioengineering, 2010, 107(6):998-1003.
Tang et al., "Protein Phosphorylation and Taurine Biosynthesis in Vivo and in Vitro," Journal of Neuroscience, Sep. 15, 1997, 17(18):6947-6951.
Tanner et al., "The complete amino acid sequence of the human erythrocyte membrane anion-transport protein deduced from the cDNA sequence," Biochem. J., 1988, 256:703-712.
Tappaz et al., "Characterization of the cDNA Coding for Rat Brain Cysteine Sulfinate Decarboxylase: Brain and Liver Enzymes are Identical Proteins Encoded by Two Distince mRNAs," J. Neurochem., 1999, 73(3):903-912.
Tinland et al., "Agrobacterium tumefaciens transfers single-stranded transferred DNA (T-DNA) into the plant cell nucleus," Proc. Natl. Acad. Sci. USA, Aug. 1994, 91:8000-8004.
Trill et al., "Production of monoclonal antibodies in COS and CHO cells," Current Opinion in Biotechnology, 1995, 6:553-560.
Uchida et al., "Molecular cloning of the cDNA for an MDCK cell Na+- and Cl-dependent taurine transporter that is regulated by hypertonicity," PNAS, Sep. 1992, 89(17):8230-8234.
Voss et al., "Regulation of the expression and subcellular localization of the taurine transporter TauT in mouse NIH3T3 fibroblasts," Eur. J. Biochem., Dec. 2004, 271(23-24):4646-4658.
Wirth et al., "Isolation of overproducing recombinant mammalian cell lines by a fast and simple selection procedure," Gene, 1988, 73:419-426.
Wu et al., "Overexpression of Anion Exchanger 2 in Human Hepatocellular Carcinoma," Chinese Journal of Physiology, 2006, 49(4):192-198.
Yang et al., "Human Hepatitis B Viral e Antigen Interacts with Cellular Interleukin-1 Receptor Accessory Protein and Triggers Interleukin-1 Response," Journal of Biological Chemistry, Nov. 10, 2006, 281(45):34525-34536.
Yang et al., "cDNA Cloning, Genomic Structure, Chromosomal Mapping, and Functional Expression of a Novel Human Alanine Aminotransferase," Genomics, Mar. 1, 2002, 79(3):445-450.
Zhang et al., "Metabolic characteristics of recombinant Chinese hamster ovary cells expressing glutamine synthetase in presence and absence of glutamine," Cytotechnology, 2006, 51(1):21-28.

Fig. 1

```
        10          20          30          40          50          60          70          80          90         100         110         120
atggctgactcaaaaccactcaatgccctggatggggaccctgtggctgtggagtccttactccgggatgtgtttgggattgttgtagatgaggccattcggaaagggaccagtgcctcg
M  A  D  S  K  P  L  N  A  L  D  G  D  P  V  A  V  E  S  L  L  R  D  V  F  G  I  V  V  D  E  A  I  R  K  G  T  S  A  S
       130         140         150         160         170         180         190         200         210         220         230         240
gagaaggtttgtgaatggaaggagcctgaagagctcaagcatctgctggatttggagctgcagagccagggcgagtctcaagagcagattctagagcgctgccgggctgtgattcactac
E  K  V  C  E  W  K  E  P  E  E  L  K  H  L  L  D  L  E  L  Q  S  Q  G  E  S  Q  E  Q  I  L  E  R  C  R  A  V  I  H  Y
       250         260         270         280         290         300         310         320         330         340         350         360
agtgtcaagactggtcacccccggttcttcaaccagctcttctcagggttagacccccatgctctggctgggcgcatcatcacagaaagcctcaacaccagccagtacacatatgagatt
S  V  K  T  G  H  P  R  F  F  N  Q  L  F  S  G  L  D  P  H  A  L  A  G  R  I  I  T  E  S  L  N  T  S  Q  Y  T  Y  E  I
       370         380         390         400         410         420         430         440         450         460         470         480
gcccctgtgtttgtcctcatggaagaggaggtgctgaagaaactccgtgccctggtgggctggaactctggggatggggtcttctgtcctggtggctccatctcgaacatgtatgccatg
A  P  V  F  V  L  M  E  E  E  V  L  K  K  L  R  A  L  V  G  W  N  S  G  D  G  V  F  C  P  G  G  S  I  S  N  M  Y  A  M
       490         500         510         520         530         540         550         560         570         580         590         600
aacctggcccgctatcagcgctacccagactgcaagcaaagaggcctccgggccctgccgcccttggctctcttcacttcaaaggagtgtcactactccatcagtaagggagctgctttt
N  L  A  R  Y  Q  R  Y  P  D  C  K  Q  R  G  L  R  A  L  P  P  L  A  L  F  T  S  K  E  C  H  Y  S  I  S  K  G  A  A  F
       610         620         630         640         650         660         670         680         690         700         710         720
ctgggacttggcactgacagtgtccgagtggtcaaggctgatgagagagggaaaatgatccctgaggatctggagaggcagatcagtctggctgaggcagagggctctgtgccatttctg
L  G  L  G  T  D  S  V  R  V  V  K  A  D  E  R  G  K  M  I  P  E  D  L  E  R  Q  I  S  L  A  E  A  E  G  S  V  P  F  L
       730         740         750         760         770         780         790         800         810         820         830         840
gtcagtaccacctctggtaccaccgtgctaggggcctttgaccccctggatgcaattgctgatgtttgccagcgtcacggattatggttacacgtggatgccgcctggggtgggagcgtc
V  S  T  T  S  G  T  T  V  L  G  A  F  D  P  L  D  A  I  A  D  V  C  Q  R  H  G  L  W  L  H  V  D  A  A  W  G  G  S  V
       850         860         870         880         890         900         910         920         930         940         950         960
ctgctgtcccggacacacaggcatctcctggatgggatccagagggctgactctgtggcctggaaccctcacaagcttctcggtgcagggctgcagtgctctgctcttcttctccgggac
L  L  S  R  T  H  R  H  L  L  D  G  I  Q  R  A  D  S  V  A  W  N  P  H  K  L  L  G  A  G  L  Q  C  S  A  L  L  L  R  D
       970         980         990        1000        1010        1020        1030        1040        1050        1060        1070        1080
acctcgaacctgctcaagcgctgccatgggtcccaggccagctacctgttccagcaggacaaattctatgacgtggctcttgacactggagacaaggtggtgcagtgtggccgccgtgtg
T  S  N  L  L  K  R  C  H  G  S  Q  A  S  Y  L  F  Q  Q  D  K  F  Y  D  V  A  L  D  T  G  D  K  V  V  Q  C  G  R  R  V
      1090        1100        1110        1120        1130        1140        1150        1160        1170        1180        1190        1200
gactgtctgaagttgtggctcatgtggaaggcacagggtgggcaaggactggagcggcgcatcgaccaggcctttgctctcacccggtacctggtggaggagataaaaaagcgggaagga
D  C  L  K  L  W  L  M  W  K  A  Q  G  G  Q  G  L  E  R  R  I  D  Q  A  F  A  L  T  R  Y  L  V  E  E  I  K  K  R  E  G
      1210        1220        1230        1240        1250        1260        1270        1280        1290        1300        1310        1320
tttgagttggtcatggagcctgagtttgtcaatgtgtgcttctggtttgtgcctcccagcctgcgggggaagaaagagagtccagattacagcaaaaggctgtctcaggtggcgcctgta
F  E  L  V  M  E  P  E  F  V  N  V  C  F  W  F  V  P  P  S  L  R  G  K  K  E  S  P  D  Y  S  K  R  L  S  Q  V  A  P  V
      1330        1340        1350        1360        1370        1380        1390        1400        1410        1420        1430        1440
ctcaaggagcgcatggtgaagaagggctccatgatgattggctaccagccccatgggacccgggccaacttcttccggatggtggtggccaaccccacactgacccaggctgatatagac
L  K  E  R  M  V  K  K  G  S  M  M  I  G  Y  Q  P  H  G  T  R  A  N  F  F  R  M  V  V  A  N  P  T  L  T  Q  A  D  I  D
      1450        1460        1470        1480
ttccttctgggcgagctggagcgtctgggccaggacctgtga
F  L  L  G  E  L  E  R  L  G  Q  D  L  *
```

Fig. 2

```
        10        20        30        40        50        60        70        80        90       100       110       120
atggaacggaccgagctgctgaagccgcggaccctggccgacctcatccgcatcttgcatgagctcttcgcgggcgacgaggtcaacgtagaggaggtgcaggctgtactggaagcctac
 M  E  R  T  E  L  L  K  P  R  T  L  A  D  L  I  R  I  L  H  E  L  F  A  G  D  E  V  N  V  E  E  V  Q  A  V  L  E  A  Y
       130       140       150       160       170       180       190       200       210       220       230       240
gagagcaatccagccgagtgggctttgtacgccaaattcgaccagtacaggtatactcgaaatcttgtggatcaaggaaatgggaagtttaatctgatgattctgtgctggggtgaagga
 E  S  N  P  A  E  W  A  L  Y  A  K  F  D  Q  Y  R  Y  T  R  N  L  V  D  Q  G  N  G  K  F  N  L  M  I  L  C  W  G  E  G
       250       260       270       280       290       300       310       320       330       340       350       360
catggcagcagtattcacgatcacacggactcccactgcttttgaagatgctgcaaggaaacctaaaggagacattgtttgcctggcctgacaaaaaatcaaatgagatgatcaagaag
 H  G  S  S  I  H  D  H  T  D  S  H  C  F  L  K  M  L  Q  G  N  L  K  E  T  L  F  A  W  P  D  K  K  S  N  E  M  I  K  K
       370       380       390       400       410       420       430       440       450       460       470       480
tcagaaaggaccttaagggaaaaccagtgtgcctacattaatgattccattgggttacatcgagtagagaatgtcagccacacggagcctgctgtgagccttcacttgtacagtccacct
 S  E  R  T  L  R  E  N  Q  C  A  Y  I  N  D  S  I  G  L  H  R  V  E  N  V  S  H  T  E  P  A  V  S  L  H  L  Y  S  P  P
       490       500       510       520       530       540       550       560       570       580       590       600
ttcgatacatgccatgcctttgatcaaagaacgggacacaaaaacaaagtcaccatgacattccacagcaaatttggaatcaggactccatttccaacttcaggttcactggagaacaac
 F  D  T  C  H  A  F  D  Q  R  T  G  H  K  N  K  V  T  M  T  F  H  S  K  F  G  I  R  T  P  F  P  T  S  G  S  L  E  N  N

taa
 *
```

Fig. 16

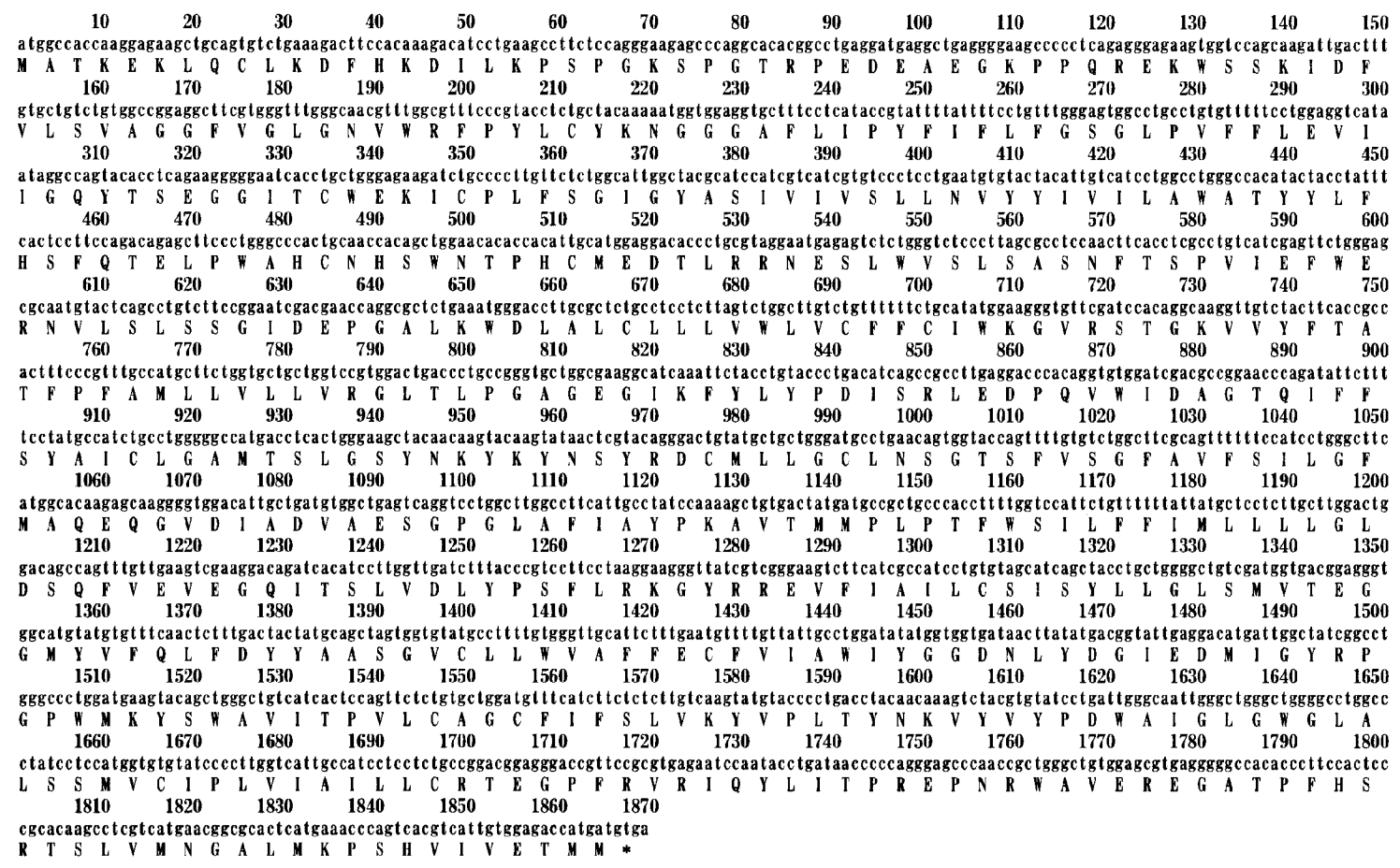

```
        10        20        30        40        50        60        70        80        90       100       110       120       130       140       150
atggccaccaaggagaagctgcagtgtctgaaagacttccacaaagacatcctgaagccttctccagggaagagcccaggcacacggcctgaggatgaggctgaggggaagcccccctcagagggagaagtggtccagcaagattgacttt
M  A  T  K  E  K  L  Q  C  L  K  D  F  H  K  D  I  L  K  P  S  P  G  K  S  P  G  T  R  P  E  D  E  A  E  G  K  P  P  Q  R  E  K  W  S  S  K  I  D  F
       160       170       180       190       200       210       220       230       240       250       260       270       280       290       300
gtgctgtctgtggccggaggcttcgtgggtttgggcaacgtttggcgtttcccgtacctctgctacaaaaatggtggaggtgctttcctcataccgtatttatttcctgtttgggagtggcctgcctgtgtttttcctggaggtcata
V  L  S  V  A  G  G  F  V  G  L  G  N  V  W  R  F  P  Y  L  C  Y  K  N  G  G  G  A  F  L  I  P  Y  F  I  F  L  F  G  S  G  L  P  V  F  F  L  E  V  I
       310       320       330       340       350       360       370       380       390       400       410       420       430       440       450
ataggccagtacacctcagaagggggaatcacctgctgggagaagatctgccccttgttctctggcattggctacgcatccatcgtcatcgtgtccctcctgaatgtgtactacattgtcatcctggcctgggccacatactacctattt
I  G  Q  Y  T  S  E  G  G  I  T  C  W  E  K  I  C  P  L  F  S  G  I  G  Y  A  S  I  V  I  V  S  L  L  N  V  Y  Y  I  V  I  L  A  W  A  T  Y  Y  L  F
       460       470       480       490       500       510       520       530       540       550       560       570       580       590       600
cactccttccagacagagcttccctgggcccactgcaaccacagctggaacacaccacattgcatggaggacaccctgcgtaggaatgagagtctctgggtctcccttagcgcctccaacttcacctcgcctgtcatcgagttctgggag
H  S  F  Q  T  E  L  P  W  A  H  C  N  H  S  W  N  T  P  H  C  M  E  D  T  L  R  R  N  E  S  L  W  V  S  L  S  A  S  N  F  T  S  P  V  I  E  F  W  E
       610       620       630       640       650       660       670       680       690       700       710       720       730       740       750
cgcaatgtactcagcctgtcttccggaatcgacgaaccaggcgctctgaaatgggaccttgcgctctgcctcctcttagtctggcttgtctgtttttctgcatatggaagggtgttcgatccacaggcaaggttgtctacttcaccgcc
R  N  V  L  S  L  S  S  G  I  D  E  P  G  A  L  K  W  D  L  A  L  C  L  L  L  V  W  L  V  C  F  F  C  I  W  K  G  V  R  S  T  G  K  V  V  Y  F  T  A
       760       770       780       790       800       810       820       830       840       850       860       870       880       890       900
actttcccgtttgccatgcttctggtgctgctggtccgtggactgaccctgccgggtgctggcgaaggcatcaaattctacctgtaccctgacatcagccgccttgaggacccacaggtgtggatcgacgccggaacccagatattcttt
T  F  P  F  A  M  L  L  V  L  L  V  R  G  L  T  L  P  G  A  G  E  G  I  K  F  Y  L  Y  P  D  I  S  R  L  E  D  P  Q  V  W  I  D  A  G  T  Q  I  F  F
       910       920       930       940       950       960       970       980       990      1000      1010      1020      1030      1040      1050
tcctatgccatctgcctgggggccatgacctcactgggaagctacaacaagtacaagtataactcgtacagggactgtatgctgctgggatgcctgaacagtggtaccagtttgtgtctggcttcgcagtttttccatcctgggcttc
S  Y  A  I  C  L  G  A  M  T  S  L  G  S  Y  N  K  Y  K  Y  N  S  Y  R  D  C  M  L  L  G  C  L  N  S  G  T  S  F  V  S  G  F  A  V  F  S  I  L  G  F
      1060      1070      1080      1090      1100      1110      1120      1130      1140      1150      1160      1170      1180      1190      1200
atggcacaagagcaaggggtggacattgctgatgtggctgagtcaggtcctggcttggccttcattgcctatccaaaagctgtgactatgatgccgctgcccaccttttggtccattctgtttttattatgctcctcttgcttggactg
M  A  Q  E  Q  G  V  D  I  A  D  V  A  E  S  G  P  G  L  A  F  I  A  Y  P  K  A  V  T  M  M  P  L  P  T  F  W  S  I  L  F  F  I  M  L  L  L  L  G  L
      1210      1220      1230      1240      1250      1260      1270      1280      1290      1300      1310      1320      1330      1340      1350
gacagccagtttgttgaagtcgaaggacagatcacatccttggttgatctttacccgtccttcctaaggaagggttatcgtcgggaagtcttcatcgccatcctgtgtagcatcagctacctgctggggctgtcgatggtgacggaggt
D  S  Q  F  V  E  V  E  G  Q  I  T  S  L  V  D  L  Y  P  S  F  L  R  K  G  Y  R  R  E  V  F  I  A  I  L  C  S  I  S  Y  L  L  G  L  S  M  V  T  E  G
      1360      1370      1380      1390      1400      1410      1420      1430      1440      1450      1460      1470      1480      1490      1500
ggcatgtatgtgtttcaactctttgactactatgcagctagtggtgtatgccttttgtgggttgcattctttgaatgttttgttattgcctggatatatggtggtgataacttatatgacggtattgaggacatgattggctatcggcct
G  M  Y  V  F  Q  L  F  D  Y  Y  A  A  S  G  V  C  L  L  W  V  A  F  F  E  C  F  V  I  A  W  I  Y  G  G  D  N  L  Y  D  G  I  E  D  M  I  G  Y  R  P
      1510      1520      1530      1540      1550      1560      1570      1580      1590      1600      1610      1620      1630      1640      1650
gggccctggatgaagtacagctgggctgtcatcactccagttctctgtgctggatgtttcatcttctctcttgtcaagtatgtacccctgacctacaacaaagtctacgtgtatcctgattggcaattggctgggctggggcctggcc
G  P  W  M  K  Y  S  W  A  V  I  T  P  V  L  C  A  G  C  F  I  F  S  L  V  K  Y  V  P  L  T  Y  N  K  V  Y  V  Y  P  D  W  A  I  G  L  G  W  G  L  A
      1660      1670      1680      1690      1700      1710      1720      1730      1740      1750      1760      1770      1780      1790      1800
ctatcctccatggtgtgtatccccttggtcattgccatcctcctctgccggacggagggaccgttccgcgtgagaatccaatacctgataacccccagggagcccaaccgctgggctgtggagcgtgagggggccacacccttccactcc
L  S  S  M  V  C  I  P  L  V  I  A  I  L  L  C  R  T  E  G  P  F  R  V  R  I  Q  Y  L  I  T  P  R  E  P  N  R  W  A  V  E  R  E  G  A  T  P  F  H  S
      1810      1820      1830      1840      1850      1860      1870
cgcacaagcctcgtcatgaacggcgcactcatgaaacccagtcacgtcattgtggagaccatgatgtga
R  T  S  L  V  M  N  G  A  L  M  K  P  S  H  V  I  V  E  T  M  M  *
```

METHOD FOR PRODUCTION OF POLYPEPTIDE

CROSS-REFERENCE TO RELATED APPLICATIONS

This application is a Continuation of U.S. application Ser. No. 13/368,945, filed Feb. 8, 2012, which is a Continuation of U.S. application Ser. No. 12/450,161, which is the U.S. National Stage application of PCT/PCT/JP2008/054579, filed Mar. 13, 2008, which claims priority from Japanese application JP 2007-066172, filed Mar. 15, 2007, the entire contents of which are incorporated herein by reference.

The instant application contains a Sequence Listing which has been submitted in ASCII format via EFS-WEB and is hereby incorporated by reference in its entirety. Said ASCII copy, created on Feb. 7, 2012, is named sequence.txt and is 69 KB.

TECHNICAL FIELD

The present invention relates to a method of producing a polypeptide, more specifically, a method of producing a polypeptide using a cell which strongly expresses cysteine sulfinic acid decarboxylase.

BACKGROUND ART

When proteins useful as pharmaceuticals are produced with the recombinant DNA technique, use of animal cells enables complicated post-translational modification and folding which prokaryotic cells can not perform. Therefore, animal cells are frequently used as host cells for producing recombinant proteins.

Recently, a large number of biopharmaceuticals, such as antibodies and physiologically active proteins, have been developed. Techniques that permit efficient production of recombinant proteins by animal cells lead to cost reduction of biopharmaceuticals and promise their stable supply to patients.

Under these circumstances, a method of protein production with higher production efficiency is desired.

β-alanine, by itself, has pH-buffering action and antioxidant action. Such β-alanine is also a precursor of stronger carnosine (Non-Patent Document 1).

In addition, it has been known that β-alanine functions as a signal peptide, organic osmolyte (Non-Patent Documents 2 and 3), and that it plays a role in maintaining enzyme activity by its chaperone-like activity (Non-Patent Document 4).

On the other hand, it has never been known that an increase in the concentration of β-alanine in cells contributes to the improvement of production of a desired recombinant protein in cultured cells.

As a β-alanine synthetase found in the brain, glutamate decarboxylase (GAD) (EC 4.1.1.15) (Non-Patent Document 5) has been known. GAD is also a decarboxylase having activity for synthesizing hypotaurine or taurine. In general, enzymes known to be used in the synthesis of taurine from a sulfur-containing amino acid such as cysteine (Non-Patent Documents 6 and 7) include cysteine sulfinic acid decarboxylase (CSAD) (EC 4.1.1.29) and cysteine dioxygenase (CDO) (EC 1.13.11.20). However, it has not been known that a large amount of β-alanine is produced if cysteine sulfinic acid decarboxylase is strongly expressed in CHO cells. Further, hamster cysteine sulfinic acid decarboxylase and hamster cysteine dioxygenase have not been known, either.

[Non-Patent Document 1]
Babizhayev, M. A., Biochim. Biophys. Acta (1989) 1004, 363-371
[Non-Patent Document 2]
Hammer, M. A., Baltz, J. M., Mol. Reprod. Dev. (2003) 66(2), 153-61
[Non-Patent Document 3]
Mariapia, V., et. al. Biochim. Biophys. Acta (2002) 1587, 83-91
[Non-Patent Document 4]
Mehta, A. D., Seidler, N. W., Journal of Enzyme Inhibition and Medicinal Chemistry (2005) 20(2), 199-203
[Non-Patent Document 5]
Kelly, C., Carter, N. D., Johnstone, A. P. and Nussey, S. S., Lancet (1991) 338 (8780), 1468-1469
[Non-Patent Document 6]
M. L. Tappaz, Neurochemical Research, Vol. 29, No. 1, January 2004, pp. 83-96
[Non-Patent Document 7]
Ian Henry Lambert, Neurochemical Research, Vol. 29, No. 1, January 2004, pp. 27-63

DISCLOSURE OF THE INVENTION

Problem for Solution by the Invention

It is an object of the present invention to provide a method which is capable of producing a natural or recombinant protein in high yield.

Means to Solve the Problem

As a result of extensive and intensive researches toward the solution of the above problem, the present inventors have found that it is possible to increase the yield of a desired polypeptide by using a cell which strongly expresses cysteine sulfinic acid decarboxylase. Thus, the present invention has been achieved. Moreover, the amount of a desired polypeptide produced could be further increased by using cells which strongly coexpresses cysteine sulfinic acid decarboxylase and a taurine transporter. Furthermore, the present inventors have found that such cells that strongly express cysteine sulfinic acid decarboxylase significantly increase the amount of β-alanine produced. Since it was anticipated that β-alanine would neutralize the fatigue substance lactate by its antioxidant action and bind it to redundant sugar in cells to eliminate them from body, an increase in the β-alanine concentration in the cells was considered to contribute to an increase in the amount of a desired polypeptide produced. Further, as a result of studies conducted by the present inventors, it was found that even when β-alanine was added to a medium for cell culture, the intracellular concentration of β-alanine could not be said to have increased, and thus that mere addition of β-alanine to a medium was insufficient.

The present invention may be summarized as follows.

(1) A method for producing a polypeptide, in which cells capable of high-yield production of β-alanine and into which DNA encoding a desired polypeptide has been transferred are cultured to produce the desired polypeptide.

(2) The production method of (1) above, wherein the cells capable of high-yield production of β-alanine are cells into which DNA encoding a protein having enzyme activity for synthesizing β-alanine from aspartic acid has been transferred.

(3) The production method of (1) above, wherein the cells capable of high-yield production of β-alanine are cells into which DNA encoding cysteine sulfinic acid decarboxylase, glutamate decarboxylase, or a mutant thereof has been transferred.

(4) The production method of any one of (1) to (3) above, wherein the cells capable of high-yield production of β-alanine are cells in which the ratio of the intracellular concentration of β-alanine on the $6^{th}$ or subsequent days after the initiation of the culture to that at the initiation of the culture is 2 or greater.

(5) The production method of any one of (1) to (3) above, wherein the cells capable of high-yield production of β-alanine are capable of increasing the β-alanine concentration in the culture medium on $6^{th}$ or subsequent days after the initiation of the culture by 50 μM or more.

(6) A cultured cell, in which the ratio of the intracellular concentration of β-alanine on the $6^{th}$ or subsequent days after the initiation of the culture to that at the initiation of the culture is 2 or greater.

(7) A cultured cell, which is capable of increasing the β-alanine concentration in the culture medium on the $6^{th}$ or subsequent days after the initiation of the culture by 50 μM or more.

(8) A method for producing a polypeptide, in which cells that strongly express cysteine sulfinic acid decarboxylase and into which DNA encoding a desired polypeptide has been transferred are cultured to produce the desired polypeptide.

(9) The production method of (8) above, wherein the cells that strongly express cysteine sulfinic acid decarboxylase are cells into which DNA encoding cysteine sulfinic acid decarboxylase has been transferred.

(10) The production method of (8) or (9) above, wherein the cells that strongly express cysteine sulfinic acid decarboxylase further express a taurine transporter strongly.

(11) The production method of (10) above, wherein the cells that strongly express a taurine transporter are cells into which DNA encoding a taurine transporter has been transferred.

(12) The method of (9) or (11) above, wherein the cell is Chinese hamster ovary cells.

(13) The method of any one of (8) to (12) above, wherein the desired polypeptide is an antibody.

(14) The method of any one of (9) to (13) above, wherein the DNA encoding the cysteine sulfinic acid decarboxylase is any one of the following (a) to (e):

(a) a DNA encoding a polypeptide having the amino acid sequence as shown in SEQ ID NO: 2, 4, 6 or 8;

(b) a DNA encoding a polypeptide which has an amino acid sequence derived from the amino acid sequence as shown in SEQ ID NO: 2, 4, 6 or 8 by substitution, deletion, addition and/or insertion of one or more amino acid residues and yet has cysteine sulfinic acid decarboxylase activity;

(c) a DNA encoding a polypeptide having 70% or more amino acid sequence homology with the amino acid sequence as shown in SEQ ID NO: 2, 4, 6 or 8 and yet having cysteine sulfinic acid decarboxylase activity;

(d) a DNA having the nucleotide sequence as shown in SEQ ID NO: 1, 3, 5 or 7;

(e) a DNA which hybridizes to a DNA complementary to a DNA having the nucleotide sequence as shown in SEQ ID NO: 1, 3, 5 or 7 under stringent conditions and yet encodes a polypeptide having cysteine sulfinic acid decarboxylase activity.

(15) A DNA encoding cysteine sulfinic acid decarboxylase, which is any one of the following (a) to (e), provided that DNA having the nucleotide sequence as shown in SEQ ID NO: 3, DNA having the nucleotide sequence as shown in SEQ ID NO: 5, and DNA having the nucleotide sequence as shown in SEQ ID NO: 7 are excluded:

(a) a DNA encoding a polypeptide having the amino acid sequence as shown in SEQ ID NO: 2;

(b) a DNA encoding a polypeptide which has an amino acid sequence derived from the amino acid sequence as shown in SEQ ID NO: 2 by substitution, deletion, addition and/or insertion of one or more amino acid residues and yet has cysteine sulfinic acid decarboxylase activity;

(c) a DNA encoding a polypeptide having 97% or more amino acid sequence homology with the amino acid sequence as shown in SEQ ID NO: 2 and yet having cysteine sulfinic acid decarboxylase activity;

(d) a DNA having the nucleotide sequence as shown in SEQ ID NO: 1;

(e) a DNA which hybridizes to a DNA complementary to a DNA having the nucleotide sequence as shown in SEQ ID NO: 1 under stringent conditions and yet encodes a polypeptide having cysteine sulfinic acid decarboxylase activity.

(16) A polypeptide which is any one of the following (A) to (E), provided that a polypeptide having the amino acid sequence as shown in SEQ ID NO: 4, a polypeptide having the amino acid sequence as shown in SEQ ID NO: 6, and a polypeptide having the amino acid sequence as shown in SEQ ID NO: 8 are excluded:

(A) a polypeptide having the amino acid sequence as shown in SEQ ID NO: 2;

(B) a polypeptide which has an amino acid sequence derived from the amino acid sequence as shown in SEQ ID NO: 2 by substitution, deletion, addition and/or insertion of one or more amino acid residues and yet has cysteine sulfinic acid decarboxylase activity;

(C) a polypeptide having 97% or more amino acid sequence homology with the amino acid sequence as shown in SEQ ID NO: 2 and yet having cysteine sulfinic acid decarboxylase activity;

(D) a polypeptide encoded by a DNA having the nucleotide sequence as shown in SEQ ID NO: 1;

(E) a polypeptide encoded by a DNA which hybridizes to a DNA complementary to a DNA having the nucleotide sequence as shown in SEQ ID NO: 1 under stringent conditions and yet encodes a polypeptide having cysteine sulfinic acid decarboxylase activity.

(17) A recombinant vector comprising the DNA of (15) above.

(18) A cell into which the DNA of (15) above has been transferred.

(19) A cell which has a transferred DNA encoding cysteine sulfinic acid decarboxylase and a transferred DNA encoding a desired polypeptide.

(20) The cell according to (19) above, which further has a transferred DNA encoding a taurine transporter.

(21) A cell which has a transferred DNA encoding cysteine sulfinic acid decarboxylase and a transferred DNA encoding a taurine transporter.

(22) A cell capable of high-yield production of β-alanine which can be obtained by transferring a DNA encoding cysteine sulfinic acid decarboxylase.

(23) The cell of (22) above, which further has a transferred DNA encoding a desired polypeptide.

Effect of the Invention

According to the present invention, it has become possible to increase the yield of a desired polypeptide.

The present specification encompasses the contents disclosed in the specification and/or the drawings of Japanese Patent Application No. 2007-66172 based on which the present patent application claims priority.

BRIEF DESCRIPTION OF THE DRAWINGS

FIG. 1 shows the nucleotide sequence of a newly cloned, CHO cell-derived hamster CSAD gene and the amino acid sequence deduced therefrom.

FIG. 2 shows the nucleotide sequence of a newly cloned, CHO cell-derived hamster CDO1 gene and the amino acid sequence deduced therefrom.

FIG. 16 shows the nucleotide sequence of a cloned, CHO cell-derived hamster taurine transporter gene and the amino acid sequence deduced therefrom.

BEST MODE FOR CARRYING OUT THE INVENTION

Figure 3:
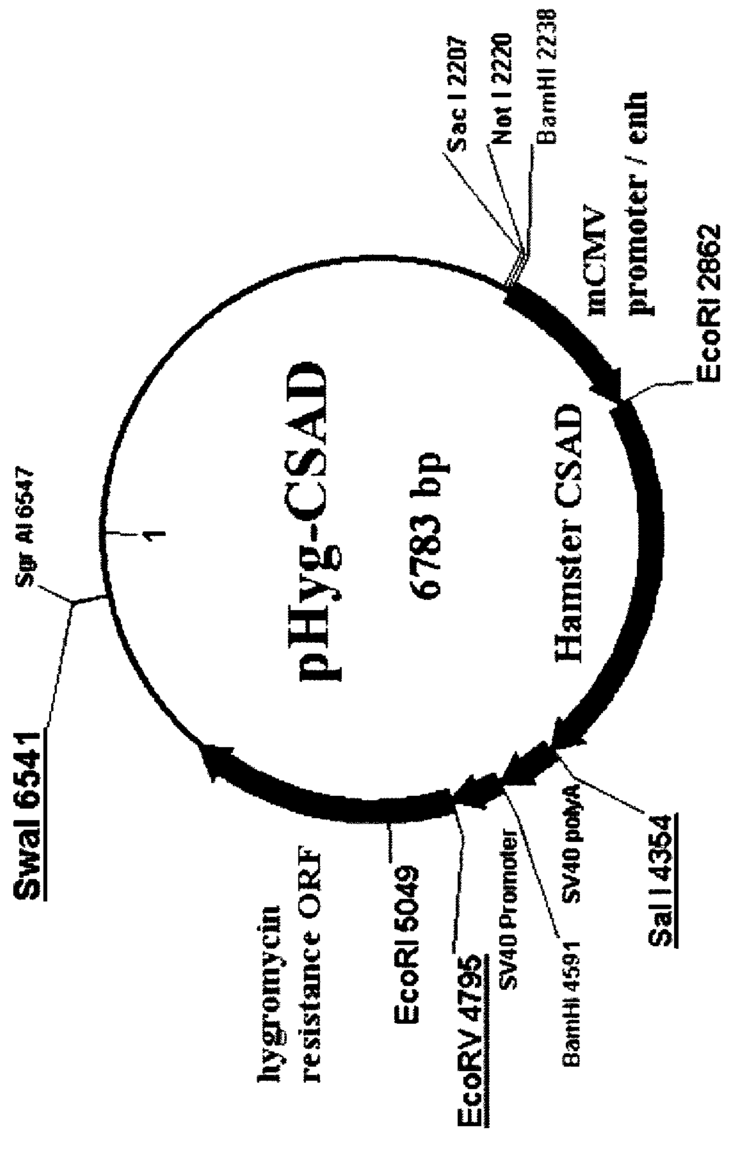
FIG. 3 shows a plasmid which was used for expressing hamster CSAD (493 amino acids).

Hereinbelow, embodiments of the present invention will be described in more detail.

The present invention provides a method of producing a polypeptide, comprising culturing a cell which strongly expresses cysteine sulfinic acid decarboxylase and has a transferred DNA encoding a desired polypeptide and thereby allowing the cell to produce the polypeptide.

In the method of the present invention, the cell may be either a natural cell capable of producing the desired polypeptide or a transformed cell into which a DNA encoding the desired polypeptide has been transferred. Preferably, a transformed cell into which a DNA encoding the desired polypeptide has been transferred is used.

In the method of the present invention, the desired polypeptide is not particularly limited. The polypeptide may be any polypeptide such as an antibody (e.g., anti-IL-6 receptor antibody, anti-IL-6 antibody, anti-glypican-3 antibody, anti-CD3 antibody, anti-CD20 antibody, anti-GPIIb/IIIa antibody, anti-TNF antibody, anti-CD25 antibody, anti-EGFR antibody, anti-Her2/neu antibody, anti-RSV antibody, anti-CD33 antibody, anti-CD52 antibody, anti-IgE antibody, anti-CD11a antibody, anti-VEGF antibody, anti-VLA4 antibody, and the like) or a physiologically active protein (e.g., granulocyte-colony stimulating factor (G-CSF), granulocyte macrophage-colony stimulating factor (GM-CSF), erythropoietin, interferon, interleukin such as IL-1 or IL-6, t-PA, urokinase, serum albumin, blood coagulation factor, PTH, and the like). An antibody is particularly preferred, and may be any antibody such as a natural antibody, a low molecular sized antibody (e.g., Fab, scFv, sc(Fv)2), a chimeric antibody, a humanized antibody, etc.

By using a cell which strongly expresses cysteine sulfinic acid decarboxylase, the yield of a polypeptide in the cell can be increased.

Cysteine sulfinic acid decarboxylase is originally known as an enzyme that converts alanine-3-sulfinic acid to hypotaurine. If cysteine sulfinic acid decarboxylase is strongly expressed in a CHO cell, the cell synthesizes an excess amount of β-alanine.

A cell which strongly expresses cysteine sulfinic acid decarboxylase is not particularly limited as long as the cell has an increased expression level of cysteine sulfinic acid decarboxylase compared to a corresponding natural cell. The natural cell is not particularly limited. A cell which is used as a host in the production of a recombinant protein (e.g., CHO cells) may be used.

As a cell which strongly expresses cysteine sulfinic acid decarboxylase, a cell into which a cysteine sulfinic acid decarboxylase gene has been artificially transferred may be given. A cell into which a cysteine sulfinic acid decarboxylase gene has been artificially transferred can be prepared by methods known to those skilled in the art. For example, such a cell may be prepared by incorporating a cysteine sulfinic acid decarboxylase gene into a vector and transforming the vector into a cell. Furthermore, the concept of "cells into which a cysteine sulfinic acid decarboxylase gene has been artificially transferred" encompasses herein cells in which an endogenous cysteine sulfinic acid decarboxylase gene has been activated by gene activation technology (see, for example, International Publication WO94/12650) so that cysteine sulfinic acid decarboxylase is strongly expressed.

As cysteine sulfinic acid decarboxylase to be strongly expressed in a cell, cysteine sulfinic acid decarboxylase derived from any organism may be used. Specifically, cysteine sulfinic acid decarboxylase derived from human, a rodent (such as mouse, rat or hamster), a puffer (such as Tiger puffer) or a sea squirt (such as *Ciona intestnalis*) may be used. Preferably, cysteine sulfinic acid decarboxylase derived from human, a rodent or the same species as the host cell may be used. For example, when the cell which is allowed to strongly express cysteine sulfinic acid decarboxylase is Chinese hamster ovary cells (CHO cells), the cysteine sulfinic acid decarboxylase is preferably derived from human or hamster.

Further, as a cysteine sulfinic acid decarboxylase gene to be strongly expressed in a cell, any one of the following DNAs (a) to (e) may be used.

(a) a DNA encoding a polypeptide having the amino acid sequence as shown in SEQ ID NO: 2, 4, 6 or 8;
(b) a DNA encoding a polypeptide which has an amino acid sequence derived from the amino acid sequence as shown in SEQ ID NO: 2, 4, 6 or 8 by substitution, deletion, addition and/or insertion of one or more amino acid residues and yet has cysteine sulfinic acid decarboxylase activity;
(c) a DNA encoding a polypeptide having 70% or more amino acid sequence homology with the amino acid sequence as shown in SEQ ID NO: 2, 4, 6 or 8 and yet having cysteine sulfinic acid decarboxylase activity;
(d) a DNA having the nucleotide sequence as shown in SEQ ID NO: 1, 3, 5 or 7;
(e) a DNA which hybridizes to a DNA complementary to a DNA having the nucleotide sequence as shown in SEQ ID NO: 1, 3, 5 or 7 under stringent conditions and yet encodes a polypeptide having cysteine sulfinic acid decarboxylase activity.

The cell which strongly expresses cysteine sulfinic acid decarboxylase may be any cell, for example, eukaryotic cell such as animal, plant and yeast cells, prokaryotic cell such as *E. coli* and *B. subtilis*, etc. Preferably, animal cells such as CHO and COS cells are used, CHO cells are particularly preferred. In order to prepare a desired polypeptide, cells suitable for transfer of a gene encoding the desired polypeptide such as CHO-dhfr-cells are preferred.

Preferably, the cell of the present invention which strongly expresses cysteine sulfinic acid decarboxylase further expresses a taurine transporter strongly in order to prepare a desired polypeptide. By transferring a gene encoding the desired polypeptide into the cell and culturing the resultant cell in a medium, the desired polypeptide can be produced in a greater amount.

When a desired polypeptide is produced using a cell into which a cysteine sulfinic acid decarboxylase gene has been artificially transferred, the order of the transfer of a cysteine sulfinic acid decarboxylase gene and the transfer of a gene encoding a desired polypeptide is not particularly limited. A gene encoding a desired polypeptide may be transferred after the transfer of a cysteine sulfinic acid decarboxylase gene. Alternatively, a cysteine sulfinic acid decarboxylase gene may be transferred after the transfer of a gene encoding a desired polypeptide. It is also possible to transfer a cysteine sulfinic acid decarboxylase gene and a gene encoding a desired polypeptide simultaneously.

A cysteine sulfinic acid decarboxylase gene and a gene encoding a desired polypeptide may be transferred simultaneously in a single vector. Alternatively, they may be transferred separately using a plurality of vectors.

By using a cell which strongly expresses cysteine sulfinic acid decarboxylase and a taurine transporter, an intracellular ammonia concentration can decline.

It is known that taurine transporter is a membrane protein having the osmoregulatory function of taking up amino acids (such as taurine and β-alanine) into cells.

A cell which strongly expresses a taurine transporter is not particularly limited as long as the cell has an increased expression level of a taurine transporter compared to a corresponding natural cell. The natural cell is not particularly limited. A cell which is used as a host in the production of a recombinant protein (e.g., CHO cells) may be used.

As a cell which strongly expresses a taurine transporter, a cell into which a taurine transporter gene has been artificially transferred may be given. A cell into which a taurine transporter gene has been artificially transferred can be prepared by methods known to those skilled in the art. For example, such a cell may be prepared by incorporating a taurine transporter gene into a vector and transforming the vector into a cell.

As a taurine transporter to be strongly expressed in a cell, a taurine transporter derived from any organism may be used. Specifically, a taurine transporter derived from human or a rodent (such as mouse, rat or hamster) may be used. Preferably, a taurine transporter derived from human, a rodent or the same species as the host cell may be used. For example, when the cell which is allowed to strongly express a taurine transporter is Chinese hamster ovary cells (CHO cells), the taurine transporter is preferably derived from human or hamster.

Further, as a taurine transporter gene to be strongly expressed in a cell, any one of the following DNAs (a) to (e) encoding a taurine transporter may be used.

(a) a DNA encoding a polypeptide having the amino acid sequence as shown in SEQ ID NO: 20, 22, 24 or 26;
(b) a DNA encoding a polypeptide which has an amino acid sequence derived from the amino acid sequence as shown in SEQ ID NO: 20, 22, 24 or 26 by substitution, deletion, addition and/or insertion of one or more amino acid residues and yet has taurine transporter activity;

(c) a DNA encoding a polypeptide having 70% or more amino acid sequence homology with the amino acid sequence as shown in SEQ ID NO: 20, 22, 24 or 26 and yet having taurine transporter activity;

(d) a DNA having the nucleotide sequence as shown in SEQ ID NO: 19, 21, 23 or 25;

(e) a DNA which hybridizes to a DNA complementary to a DNA having the nucleotide sequence as shown in SEQ ID NO: 19, 21, 23 or 25 under stringent conditions and yet encodes a polypeptide having taurine transporter activity.

Production of a desired polypeptide may be performed by transferring a gene encoding the desired polypeptide into a cell which strongly expresses a taurine transporter gene and a cysteine sulfinic acid decarboxylase gene and culturing the resultant cell in a medium. Furthermore, a desired polypeptide can be prepared by using a cell in which an endogenous gene has been activated by gene activation technology (see, for example, International Publication WO94/12650) so that a desired polypeptide has been produced.

When a desired polypeptide is produced using a cell into which a taurine transporter gene and a cysteine sulfinic acid decarboxylase gene have been artificially transferred, the order of the transfer of a taurine transporter gene, the transfer of a cysteine sulfinic acid decarboxylase gene and the transfer of a gene encoding a desired polypeptide is not particularly limited. A gene encoding a desired polypeptide may be transferred after the transfer of a taurine transporter gene and a cysteine sulfinic acid decarboxylase gene. Alternatively, a taurine transporter gene and a cysteine sulfinic acid decarboxylase gene may be transferred after the transfer of a gene encoding a desired polypeptide. It is also possible to transfer a taurine transporter gene, a cysteine sulfinic acid decarboxylase gene and a gene encoding a desired polypeptide simultaneously.

A taurine transporter gene, a cysteine sulfinic acid decarboxylase gene and a gene encoding a desired polypeptide may be transferred simultaneously in a single vector. Alternatively, they may be transferred separately using a plurality of vectors.

For culturing the cell which strongly expresses cysteine sulfinic acid decarboxylase (and which may strongly express a taurine transporter), media used in conventional cell culture (preferably, animal cell culture) may be used. These media usually contain amino acids, vitamins, lipid factors, energy sources, osmotic regulators, iron sources and pH regulators. The contents of these components are usually as follows: amino acids 0.05-1500 mg/L, vitamins 0.001-10 mg/L, lipid factors 0-200 mg/L, energy sources 1-20 g/L, osmotic regulators 0.1-10000 mg/L, iron sources 0.1-500 mg/L, pH regulators 1-10000 mg/L, trace metal elements 0.00001-200 mg/L, surfactants 0-5000 mg/L, growth cofactors 0.05-10000 μg/L and nucleosides 0.001-50 mg/L. However, the contents are not limited to these ranges and may be appropriately selected depending on the type of the cell to be cultured, the type of the desired polypeptide, and so on.

In addition to these components, trace metal elements, surfactants, growth cofactors, nucleosides, and the like may be added.

Specific examples of such components include amino acids, such as L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, preferably, L-alanine, L-arginine, L-asparagine, L-aspartic acid, L-cystine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine; vitamins, such as i-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin $B_{12}$ and ascorbic acid, preferably, biotin, folic acid, lipoic acid, nicotinamide, calcium pantothenate, pyridoxal hydrochloride, riboflavin, thiamine hydrochloride, vitamin $B_{12}$ and ascorbic acid; lipid factors, such as choline chloride, choline tartrate, linoleic acid, oleic acid and cholesterol, preferably, choline chloride; energy sources, such as glucose, galactose, mannose, and fructose, preferably, glucose; osmotic regulators, such as sodium chloride, potassium chloride, and potassium nitrate, preferably, sodium chloride; iron sources, such as iron EDTA, ferric citrate, ferrous chloride, ferric chloride, ferrous sulfate, ferric sulfate, and ferric nitrate, preferably, ferric chloride, iron EDTA, and ferric citrate; and pH regulators, such as sodium hydrogencarbonate, calcium chloride, sodium dihydrogenphosphate, HEPES and MOPS, preferably, sodium hydrogencarbonate. Culture media containing any of these components may be given as examples.

Besides the above components, there may be added trace metal elements, such as copper sulfate, manganese sulfate, zinc sulfate, magnesium sulfate, nickel chloride, tin chloride, magnesium chloride and sodium subsilicate, preferably, copper sulfate, zinc sulfate and magnesium sulfate; surfactants, such as Tween 80 and Pluronic F68; growth cofactors, such as recombinant insulin, recombinant IGF-1, recombinant EGF, recombinant FGF, recombinant PDGF, recombinant TGF-α, ethanolamine hydrochloride, sodium selenite, retinoic acid and putrescine dihydrochloride, preferably, sodium selenite, ethanolamine hydrochloride, recombinant IGF-1 and putrescine dihydrochloride; and nucleosides, such as deoxyadenosine, deoxycytidine, deoxyguanosine, adenosine, cytidine, guanosine and uridine. In preferable examples of above media, antibiotics, such as streptomycin, penicillin-G potassium and gentamicin, and pH-indicators, such as Phenol Red, may be contained.

The pH of the medium varies depending on the cell to be cultured. Generally, pH 6.8-7.6 is appropriate. In many cases, pH 7.0-7.4 is appropriate.

It is also possible to use a commercial medum for animal cell culture, e.g., D-MEM (Dulbecco's Modified Eagle Medium), D-MEM/F-12 1:1 Mixture (Dulbecco's Modified Eagle Medium: Nutrient Mixture F-12), RPMI1640, CHO-S-SFMII (Invitrogen), CHO-SF (Sigma-Aldrich), EX-CELL 301 (JRH Biosciences), CD-CHO (Invitrogen), IS CHO-V (Irvine Scientific), PF-ACF-CHO (Sigma-Aldrich) or the like.

Alternatively, the medium may be a serum-free medium.

When the cell which strongly expresses cysteine sulfinic acid decarboxylase (and which may strongly express a taurine transporter) is CHO cells, CHO cells may be cultured by methods known to those skilled in the art. For example, CHO cells may be cultured usually in an atmosphere with a $CO_2$ concentration in the gas phase of 0 to 40%, preferably 2 to 10%, at 30 to 39° C., preferably about 37° C.

As is clear from the Examples described later, production of waste products (such as lactate) which turn to be cell growth inhibitory substances can be inhibited in a cell strongly expressing cysteine sulfinic acid decarboxylase. As a result, the cell shows the effect of maintaining a high survival ratio. The cell of the present invention is capable of culturing for twenty days or a longer period, preferably thirty days or a longer period, more preferably two months or a still longer period.

Further, when a desired polypeptide, such as an antibody, is produced in cultured cells, the cells come into a highly concentrated state (about $1\times10^7$ cells/ml) at the late-stage of culture, and the influence of waste products such as lactate becomes extremely high. When a desired polypeptide is produced using the cell which strongly expresses cysteine sulfinic acid decarboxylase, a high survival ratio is maintained even at the late-stage of culture, and an improvement can be expected in the yield of the desired polypeptide.

An appropriate culture period for producing a desired polypeptide using the cell which strongly expresses cysteine sulfinic acid decarboxylase is usually 1 day to 3 months, preferably 1 day to 2 months, more preferably 1 day to 1 month.

With respect to various culture devices for animal cell culture, a fermentor type tank culture device, an air lift type culture device, a culture flask type culture device, a spinner flask type culture device, a microcarrier type culture device, a fluidized bed type culture device, a hollow fiber type culture device, a roller bottle type culture device, a packed bed type culture device, or the like may be used.

Culture may be performed by any culture method such as batch culture, fed-batch culture or continuous culture. Preferably, fed-batch culture or continuous culture is used. Fed-batch culture is more preferred.

When the cell which strongly expresses cysteine sulfinic acid decarboxylase (and which may strongly express a taurine transporter) is cultured, taurine may be added to the medium in order to promote taurine uptake into cells.

The present invention provides a novel polypeptide which is any one of the following (A) to (E), provided that a polypeptide having the amino acid sequence as shown in SEQ ID NO: 4, a polypeptide having the amino acid sequence as shown in SEQ ID NO: 6, and a polypeptide having the amino acid sequence as shown in SEQ ID NO: 8 are excluded:

(A) a polypeptide having the amino acid sequence as shown in SEQ ID NO: 2;

(B) a polypeptide which has an amino acid sequence derived from the amino acid sequence as shown in SEQ ID NO: 2 by substitution, deletion, addition and/or insertion of one or more amino acid residues and yet has cysteine sulfinic acid decarboxylase activity;

(C) a polypeptide having 97% or more amino acid sequence homology with the amino acid sequence as shown in SEQ ID NO: 2 and yet having cysteine sulfinic acid decarboxylase activity;

(D) a polypeptide encoded by a DNA having the nucleotide sequence as shown in SEQ ID NO: 1; or (E) a polypeptide encoded by a DNA which hybridizes to a DNA complementary to a DNA having the nucleotide sequence as shown in SEQ ID NO: 1 under stringent conditions and yet encodes a polypeptide having cysteine sulfinic acid decarboxylase activity.

The novel polypeptides of the present invention are hamster cysteine sulfinic acid decarboxylase and those polypeptides which are functionally equivalent thereto. In the present invention, the expression "a polypeptide that is functionally equivalent to cysteine sulfinic acid decarboxylase" is used to mean that the polypeptide has a decarboxylation activity that is equivalent to the activity possessed by hamster cysteine sulfinic acid decarboxylase, such as enzyme activity for synthesizing hypotaurine from 3-sulfinic acid alanine, enzyme activity for synthesizing taurine from cysteic acid, and enzyme activity as of glutamate decarboxylase for synthesizing β-alanine from aspartic acid. Such a polypeptide encompasses, for example, mutants of hamster cysteine sulfinic acid decarboxylase.

As methods well-known to those skilled in the art for preparing polypeptides functionally equivalent to a specific polypeptide, methods of introducing mutations into polypeptides may be given. For example, those skilled in the art could prepare polypeptides functionally equivalent to hamster cysteine sulfinic acid decarboxylase by appropriately introducing mutations into amino acids of hamster cysteine sulfinic acid decarboxylase by site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc Natl Acad Sci USA. 82, 488-492; Kunkel (1988) Methods Enzymol. 85, 2763-2766). Mutations in amino acids may also occur in nature. Thus, a polypeptide which has an amino acid derived from the amino acid sequence of the hamster cysteine sulfinic acid decarboxylase of the present invention by mutation of one or more amino acids and is functionally equivalent to hamster cysteine sulfinic acid decarboxylase is also included in the novel polypeptide of the present invention.

Specific examples of polypeptides functionally equivalent to the hamster cysteine sulfinic acid decarboxylase of the present invention include, but are not limited to, a polypeptide having an amino acid sequence derived from the amino acid sequence of the hamster cysteine sulfinic acid decarboxylase by deletion of one or more amino acids, preferably 1-30 amino acids, more preferably 1-10 amino acids; a polypeptide having an amino acid sequence derived from the amino acid sequence of the hamster cysteine sulfinic acid decarboxylase by addition of one or more amino acids, preferably 1-30 amino acids, more preferably 1-10 amino acids; and a polypeptide having an amino acid sequence derived from the amino acid sequence of the hamster cysteine sulfinic acid decarboxylase by substitution of one or more amino acids, preferably 1-30 amino acids, more preferably 1-10 amino acids, with other amino acids.

Amino acid residues to be mutated are not particularly limited. Preferably, amino acid residues are mutated to other amino acids in which the nature of the initial amino acid side chain is conserved. Specific examples of the nature of amino acid side chain include hydrophobic amino acids (A, I, L, M, F, P, W, Y and V), hydrophilic amino acids (R, D, N, C, E, Q, G, H, K, S and T), amino acids with an aliphatic side chain (G A, V, L, I and P), amino acids with a hydroxyl group-containing side chain (S, T and Y), amino acids with a sulfur atom-containing side chain (C and M), amino acids with a carboxylic acid and amide-containing side chain (D, N, E and Q), amino acids with a base-containing side chain (R, K and H) and amino acids with an aromatic-containing side chain (H, F, Y and W) (In parentheses are one-letter codes for amino acids).

It has been reported that a polypeptide having an amino acid sequence derived from an original amino acid sequence by modification (such as deletion, addition and/or substitution of one or more amino acids) maintains the biological activity of the original polypeptide (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G et al., Proc. Natl. Acad. Sci. USA (1982) 79, 6409-6413).

As one example of the polypeptide in which one or more amino acid residues are added to the hamster cysteine sulfinic acid decarboxylase of the present invention, a fusion polypeptide comprising the hamster cysteine sulfinic acid decarboxylase may be given. Such a fusion polypeptide is composed of the protein of the invention (hamster cysteine sulfinic acid decarboxylase) and other polypeptide fused thereto. Such a fusion polypeptide is included in the present invention. Such a fusion polypeptide may be prepared by linking a gene encoding the hamster cysteine sulfinic acid decarboxylase of the present invention in frame with a gene encoding the other polypeptide, transferring the resultant DNA into an expression vector and expressing the DNA in a host cell. Techniques known to those skilled in the art may be used. There is no limitation on the polypeptide to be fused to the polypeptide of the present invention.

Examples of polypeptides to be fused to the polypeptide of the present invention include, but are not limited to, FLAG (Hopp, T. P. et al., BioTechnology (1988) 6, 1204-1210), 6×His comprising six histidine (His) residues, 10×His, influenza hemagglutinin (HA), human c-myc fragment, VSV-GP fragment, p18HIV fragment, T7-tag, HSV-tag, E-tag, SV40T antigen fragment, lck tag, α-tubulin fragment, B-tag, protein C fragment, glutathione-S-transferase (GST), influenza hemagglutinin (HA), immunoglobulin constant region, β-galactosidase and maltose-binding protein (MBP).

A commercially available gene encoding such polypeptide is fused to the gene encoding the polypeptide of the present invention. The fused gene thus prepared is expressed to prepare a fused polypeptide.

An alternative method known to those skilled in the art for preparing polypeptides functionally equivalent to a specific polypeptide is a method using the hybridization technique (Sambrook, J et al., Molecular Cloning 2nd ed., 9.47-9.58, Cold Spring Harbor Lab. Press, 1989). Those skilled in the art could routinely isolate a DNA highly homologous to the DNA sequence of the hamster cysteine sulfinic acid decarboxylase of the present invention based on that DNA sequence or a part thereof, and isolate polypeptides functionally equivalent to the hamster cysteine sulfinic acid decarboxylase from that DNA. Thus, a polypeptide which is encoded by a DNA hybridizing to the DNA, or a part thereof, encoding the hamster cysteine sulfinic acid decarboxylase of the present invention and is functionally equivalent to the hamster cysteine sulfinic acid decarboxylase of the present invention is also included in the polypeptide of the present invention.

Hybridization conditions for isolating a DNA encoding a polypeptide functionally equivalent to the hamster cysteine sulfinic acid decarboxylase of the present invention can be appropriately selected by those skilled in the art. For example, low stringent hybridization conditions may be given. Low stringent hybridization conditions are, for example, 42° C., 2×SSC and 0.1% SDS, preferably 50° C., 2×SSC and 0.1% SDS. More preferably, high stringent conditions may be given. For example, high stringent conditions are 65° C., 2×SSC and 0.1% SDS. Under these conditions, as the hybridization temperature is lowered, not only DNAs with high homology but also DNAs with only low homology are obtained. Conversely, it is expected that only those DNAs with high homology are obtained as the hybridization temperature is elevated. However, not only the temperature but also a plurality of factors (such as salt concentrations) affect the stringency of hybridization. Those skilled in the art could appropriately select these factors to realize similar stringency.

The polypeptide encoded by a DNA isolated by these hybridization techniques usually has high homology with the hamster cysteine sulfinic acid decarboxylase of the present invention in the amino acid sequence. The polypeptide of the present invention also include those polypeptides which are functionally equivalent to the hamster cysteine sulfinic acid decarboxylase of the present invention and have high homology with the amino acid sequence of the hamster cysteine sulfinic acid decarboxylase of the present invention. The term "high homology" refers to usually 97% or more homology, preferably 98% or more homology, more preferably 99% or more homology. For determination of the homology of polypeptides, the algorithm described in Wilbur, W. J. and Lipman, D. J., Proc. Natl. Acad. Sci. USA (1983) 80, 726-730 may be followed.

The polypeptide of the present invention may vary in amino acid sequence, molecular weight, isoelectric point, presence or absence of sugar chains, morphology, etc. depending on the cell or host that produce the polypeptide or the purification method that will be described later. However, as long as the resultant polypeptide has functions equivalent to the functions of the hamster cysteine sulfinic acid decarboxylase of the present invention, the polypeptide is included in the present invention. For example, when the polypeptide of the present invention is expressed in a prokaryote (e.g., *Escherichia coli*), a methionine reside is added to the N-terminus of the initial amino acid sequence of the polypeptide. When the polypeptide of the present invention is expressed in a eukaryote (e.g., a mammalian cell), the N-terminal signal sequence is removed. The polypeptide of the present invention includes such polypeptides.

The polypeptide of the present invention may be prepared as a recombinant polypeptide or a natural polypeptide by methods known to those skilled in the art. A recombinant polypeptide may be prepared by incorporating a DNA encoding the polypeptide of the present invention in an appropriate expression vector, introducing the vector into an appropriate host cell, collecting the resultant transformant, extracting a crude polypeptide, and then purifying the polypeptide by chromatography (such as ion exchange, reversed phase or gel filtration chromatography, or affinity chromatography in which an antibody to the polypeptide of the present invention is fixed in a column) or a combination of these chromatographic techniques.

When the polypeptide of the present invention is expressed in a host cell (e.g., animal cell or *E. coli*) as a fusion polypeptide with glutathione-S-transferase polypeptide or as a recombinant polypeptide with histidine residues added thereto, the expressed polypeptide may be purified with a glutathione column or a nickel column.

After purification of a fusion polypeptide, regions other than the polypeptide of interest may be cut off by thrombin or factor Xa and removed from the fusion polypeptide.

When the polypeptide of the present invention is a natural polypeptide, the polypeptide may be isolated by purification methods known to those skilled in the art. For example, an extract from tissues or cells expressing the polypeptide of the present invention may be applied to an affinity column to which an antibody to the hamster cysteine sulfinic acid decarboxylase described later is bound. The antibody may be either a polyclonal antibody or a monoclonal antibody.

Further, the present invention provides a novel DNA encoding cysteine sulfinic acid decarboxylase, which is any one of the following (a) to (e), provided that DNA having the nucleotide sequence as shown in SEQ ID NO: 3, DNA having the nucleotide sequence as shown in SEQ ID NO: 5, and DNA having the nucleotide sequence as shown in SEQ ID NO: 7 are excluded:

(a) a DNA encoding a polypeptide having the amino acid sequence as shown in SEQ ID NO: 2;

(b) a DNA encoding a polypeptide which has an amino acid sequence derived from the amino acid sequence as shown in SEQ ID NO: 2 by substitution, deletion, addition and/or insertion of one or more (several) amino acid residues and yet has cysteine sulfinic acid decarboxylase activity;

(c) a DNA encoding a polypeptide having 97% or more amino acid sequence homology with the amino acid sequence as shown in SEQ ID NO: 2 and yet having cysteine sulfinic acid decarboxylase activity;

(d) a DNA having the nucleotide sequence as shown in SEQ ID NO: 1; or (e) a DNA which hybridizes to a DNA complementary to a DNA having the nucleotide sequence as shown in SEQ ID NO: 1 under stringent conditions and yet encodes a polypeptide having cysteine sulfinic acid decarboxylase activity.

The novel DNA of the present invention is used to prepare a cell which strongly expresses cysteine sulfinic acid decarboxylase and thereafter used in the in vivo or in vitro production of a desired polypeptide as described above. The novel DNA of the present invention may take any form as long as it is capable of encoding a polypeptide having cysteine sulfinic acid decarboxylase activity. That is, the DNA may be, for example, a cDNA synthesized from mRNA, a genomic DNA or a chemically synthesized DNA. It should be noted that, as long as the DNA is capable of encoding the polypeptide of the present invention, the DNA may have any nucleotide sequence based on the degeneracy of genetic codes.

The DNA of the present invention may be prepared by methods known to those skilled in the art. For example, the DNA may be prepared by preparing a cDNA library from a cell expressing a polypeptide having cysteine sulfinic acid decarboxylase activity and performing hybridization using a part of the DNA sequence of the present invention (e.g., SEQ ID NO: 1) as a probe. The cDNA library may be prepared, for example, by the method described in Sambrook, J. et al., Molecular Cloning, Cold Spring Harbor Laboratory Press (1989). Alternatively, a commercial cDNA library may be used. It is also possible to prepare the DNA of the present invention by preparing RNA from a cell expressing a polypeptide having cysteine sulfinic acid decarboxylase activity, synthesizing oligo DNA molecules based on the DNA sequence of the present invention (e.g., SEQ ID NO: 1), and performing PCR using the oligo DNA molecules as primers to thereby amplify a cDNA encoding cysteine sulfinic acid decarboxylase.

Further, by determining the nucleotide sequence of the resultant cDNA, it is possible to determine the translation region encoding the polypeptide and to obtain the amino acid sequence of the polypeptide of the present invention. Further, by screening a genomic library using the resultant cDNA as a probe, it is possible to isolate a genomic DNA.

Specifically, the following procedures may be used. First, mRNA is isolated from cells, tissues or the like expressing the polypeptide of the present invention. For the isolation of mRNA, the total RNA is prepared by known methods, for example, the guanidine ultracentrifugation method (Chirgwin, J. M. et al., Biochemistry (1979) 18, 5294-5299), the AGPC method (Chomczynski, P. and Sacchi, N., Anal. Biochem. (1987) 162, 156-159) or the like, and then mRNA is purified from the total RNA using mRNA Purification Kit (Pharmacia), etc. Alternatively, mRNA may be prepared directly using QuickPrep mRNA Purification Kit (Pharmacia).

From the resultant mRNA, cDNA is synthesized using a reverse transcriptase. Alternatively, cDNA may be synthesized using a kit such as AMV Reverse Transcriptase First-Strand cDNA Synthesis Kit (SEIKAGAKU CORPORATION). It is also possible to synthesize and amplify cDNA according to the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) using 5'-Ampli FINDER RACE Kit (Clontech) and polymerase chain reaction (PCR) with primers.

A DNA fragment of interest is prepared from the resultant PCR product and ligated to a vector DNA to thereby prepare a recombinant vector. The vector is introduced into a host (e.g., E. coli), followed by selection of resultant colonies to thereby obtain a desired recombinant vector. The nucleotide sequence of the DNA of interest may be confirmed by a known method such as the dideoxynucleotide chain termination method.

Further, a nucleotide sequence of a higher expression efficiency can be designed for the DNA of the present invention by considering the frequency of codon usage in the host to be used for expression (Grantham, R. et al., Nucleic Acids Research (1981) 9, p. 43-74). Further, the DNA of the present invention can be modified using commercially available kits or known methods. Examples of such modifications include, but are not limited to, digestion with restriction enzymes, insertion of synthetic oligonucleotides or appropriate DNA fragments, addition of linkers, and insertion of an initiation codon (ATG) and/or a termination codon (TAA, TGA or TAG).

The DNA of the present invention also includes a DNA which hybridizes to a DNA having the nucleotide sequence as shown in SEQ ID NO: 1 under stringent conditions and encodes a polypeptide functionally equivalent to cysteine sulfinic acid decarboxylase.

Stringent conditions can be appropriately selected by those skilled in the art, including, for example, low stringent conditions. Low stringent conditions refer to, for example, 42° C., 2×SSC and 0.1% SDS, preferably 50° C., 2×SSC and 0.1% SDS. More preferably, high stringent conditions may be selected. High stringent conditions refer to, for example, 65° C., 2×SSC and 0.1% SDS. Under these conditions, as the hybridization temperature is elevated, DNAs with a higher homology can be obtained. The above-described DNA which hybridizes is preferably a DNA derived from nature, e.g., cDNA or chromosomal DNA.

These DNAs isolated by hybridization techniques usually have a high nucleotide sequence identity with a DNA encoding the hamster cysteine sulfinic acid decarboxylase of the present invention. The DNA of the present invention also includes a DNA which encodes a polypeptide functionally equivalent to the hamster cysteine sulfinic acid decarboxylase of the present invention and has high identity with a DNA encoding the hamster cysteine sulfinic acid decarboxylase of the present invention. The term "high identity" refers to usually 96% or more homology, preferably 98% or more homology, more preferably 99% or more identity. The identity of nucleotide sequences may be determined by algorithm BLAST (Karlin and Altschul, Proc. Natl. Acad. Sci. USA 90:5873-5877, 1993). Based on this algorithm, programs such as BLASTN and BLASTX have been developed (Altschul et al. J. Mol. Biol. 215:403-410, 1990). When nucleotide sequences are analyzed by BLASTN based on BLAST, parameters may be set as score=100 and wordlength=12, for example. Specific procedures for these analysis methods are known (http://www.ncbi.nlm.nih.gov.).

Further, the present invention provides a vector into which the DNA of the present invention has been inserted. The vector of the present invention is useful for retaining the DNA of the present invention within the host cell and for permitting expression of the polypeptide of the present invention (i.e., hamster cysteine sulfinic acid decarboxylase or a polypeptide functionally equivalent thereto). The vector of the present invention is also useful for permitting the host cell to strongly express the cysteine sulfinic acid decarboxylase. By permitting the host cell to strongly express the cysteine sulfinic acid decarboxylase, a production of a desired polypeptide in the host cell can be increased.

When the host cell to be used is *E. coli*, it is preferable that the vector has a replication origin ("ori") so that the vector is largely amplified in *E. coli* (e.g., JM109, DH5α, HB101 and XL1-Blue) and prepared in large quantity, and also genes for selecting transformed *E. coli* (e.g., drug resistance genes that enable discrimination of transformant with some drugs such as ampicillin, tetracycline, kanamycin or chloramphenicol). Examples of preferable vectors include, but are not limited to, M13 vectors, pUC vectors, pBR322, pBluescript and pCR-Script. In addition to these vectors, pGEM-T, pDIRECT, pT7, etc. may be enumerated when the vector is used for the purpose of subcloning a cDNA and cutting off the subcloned cDNA. When the vector is used for the purpose of producing the polypeptide of the present invention, an expression vector is especially useful. When expression in *E. coli* is intended, the expression vector preferably has the above-described features so that the vector is amplified in *E. coli*, and it also preferably has a promoter which allows efficient expression in *E. coli* such as JM109, DH5α, HB101 or XL1-Blue, e.g., lacZ promoter (Ward et al, Nature (1989) 341, 544-546; FASEB J. (1992) 6, 2422-2427), araB promoter (Better et al, Science (1988) 240, 1041-1043) or T7 promoter. Specific examples of such vector include, in addition to those listed above, pGEX-5X-1 (Pharmacia), QIAexpress system (Qiagen), pEGFP, or pET (for its host, T7 RNA polymerase-expressing BL21 is preferred).

The vector may comprise signal sequences for polypeptide secretion. When the polypeptide is to be produced in the periplasm of *E. coli*, pelB signal sequence (Lei, S. P. et al., J. Bacteriol. (1987) 169, 4379) may be used as a signal sequence for polypeptide secretion. Introduction of the vector into a host cell may be performed, for example, by the calcium chloride method or electroporation.

In cases where a host cell other than *E. coli* is used, vectors useful for producing the polypeptide of the present invention include, but are not limited to, mammal-derived expression vectors [e.g., pcDNA3 from Invitrogen; pEGF-BOS (Nucleic Acids. Res. 1990, 18(17), p. 5322); pEF, pCDM8], insect cell-derived expression vectors (e.g., Bac-to-BAC baculovairus expression system from GIBCO BRL; pBacPAK8), plant-derived expression vectors (e.g., pMH1, pMH2), animal virus-derived expression vectors (e.g., pHSV, pMV, pAdex-Lcw), retrovirus-derived expression vectors (e.g., pZIpneo), yeast-derived expression vectors (e.g., *Pichia* Expression Kit fron Invitrogen; pNVll; SP-Q01), and *Bacillus subtilis*-derived expression vectors (e.g., pPL608, pKTH50).

When expression of the polypeptide in animal cells (such as CHO cells, COS cells, NIH3T3 cells, etc.) is intended, the vector preferably has a promoter necessary for expressing the polypeptide in those cells. Examples of such promoter include, but are not limited to, SV40 promoter (Mulligan et al, Nature (1979) 277, 108), MMLV-LTR promoter, EF1α promoter (Mizushima et al., Nucleic Acids Res. (1990) 18, 5322) and CMV promoter. More preferably, the vector also has genes for selecting transformed cells (e.g., drug resistance genes that enable discrimination with drugs such as neomycin or G418). Examples of vectors having such properties include, but are not limited to, pMAM, pDR2, pBK-RSV, pBK-CMV, pOPRSV and pOP13.

Further, when stable expression of a gene of interest and intracellular amplification of the copy number of the gene are indented, the following method may be used. Briefly, into CHO cells lacking a nucleic acid synthesis pathway, a vector having DHFR gene that complements the lack (e.g., pCHOI) is introduced, followed by amplification with methotrexate (MTX). On the other hand, when tentative expression of a gene of interest is intended, a method may be used in which COS cells carrying a gene expressing SV40T antigen on the chromosome is transformed with a vector having the replication origin of SV40 (e.g., pcD). As the replication origin, a replication origin derived from polyomavirus, adenovirus or bovine papillomavirus (BPV) may also be used. Further, the expression vector may contain selectable markers for amplifying the copy number of the gene in a host cell system. Examples of such selectable markers include, but are not limited to, aminoglycoside phosphotransferase (APH) gene, thymidine kinase (TK) gene, *E. coli* xanthine-guanine phosphoribosyl transferase (Ecogpt) gene and dihydrofolate reductase (dhfr) gene.

The present invention also provides a host cell into which the DNA of the present invention (which may be incorporated into a vector) has been transferred. The host cell into which the DNA of the present invention (which may be incorporated into a vector) is transferred is not particularly limited. For example, *E. coli* or various animal cells may be used. The host cell of the present invention may be used, for example, as a production system for the preparation or expression of the polypeptide of the present invention. If DNA encoding a desired polypeptide is transferred into the host cell of the present invention, the host cell of the present invention can strongly express cysteine sulfinic acid decarboxylase, which leads to an increased production of the desired polypeptide. DNA encoding a taurine transporter (which may be incorporated into a vector) may be further transferred into the host cell of the present invention. By transferring DNA encoding a desired polypeptide and DNA encoding a taurine transporter into the host cell of the present invention, the yield of the desired polypeptide can be increased. For the production of the polypeptide, there are in vivo and in vitro production systems. Examples of in vitro production systems include systems using eukaryotes and systems using prokaryotes.

The present invention also provides a cell into which DNA encoding cysteine sulfinic acid decarboxylase and DNA encoding a taurine transporter have been transferred.

When eukaryotes are used, animal cells, plant cells, fungal cells, etc. may be used as the host. Specific examples of animal cells include mammalian cells, such as CHO cells (J. Exp. Med. (1995) 108, 945), COS cells, 3T3 cells, myeloma cells, BHK (baby hamster kidney) cells, HeLa cells and Vero cells; amphibian cells, such as oocytes of *Xenopus laevis* (Valle, et al., Nature (1981) 291, 358-340); or insect cells, such as sf9, sf21 and Tn5 cells. Among CHO cells, dhfr-CHO lacking DHFR gene (Proc. Natl. Acad. Sci. USA (1980) 77, 4216-4420) and CHO K-1 (Proc. Natl. Acad. Sci. USA (1968) 60, 1275) are used with particular advantage. When high expression is intended in an animal cell, CHO cells are especially preferred. Introduction of DNA (which may be incorporated into a vector) into the host cell may be performed by such methods as the calcium phosphate method, the DEAE dextran method, a method using a cationic ribosome DOTAP (Boehringer-Mannheim), electroporation, lipofection, etc.

As plant cells for polypeptide production, a *Nicotiana tabacum*-derived cell is known as a polypeptide production system and this may be subjected to callus culture. As fungal cells for polypeptide production, specific examples include yeast belonging to the genus *Saccharomyces*, e.g., *Saccharomyces cerevisiae*, and filamentous fungi belonging to the genus *Aspergillus*, e.g., *Aspergillus niger.*

When prokaryotes are used, production systems using bacterial cells are known. Specific examples of such bacterial cells include *E. coli* (such as JM109, DH5α, HB101) and *Bacillus subtilis*.

The polypeptide encoded by a gene of interest may be obtained by transforming these cells with the gene of interest and culturing the transformed cells in vitro. The culture may be performed by known methods. For example, as a culture broth for animal cells, a medium such as DMEM, MEM, RPMI1640 or IMDM may be used. A serum supplement such as fetal calf serum (FCS) may be used jointly. Alternatively, serum-free culture may be performed. The pH during culture is preferably about 6 to 8. The culture is usually performed at about 30-40° C. for about 15-200 hours. If necessary, replacement of the medium, aeration and agitation are carried out.

On the other hand, in vivo production systems include those using animals or plants. A gene of interest is transferred into these animals or plants to produce the polypeptide in the animal bodies or plant bodies. Then, the polypeptide is collected. The term "host" as used herein includes such animals or plants.

When animals are used, available production systems include those using mammals or insects. Goat, pig, sheep, mouse and cattle may be used as mammals (Vicki Glaser, SPECTRUM Biotechnology Applications, 1993). When mammals are used, transgenic animals may be used.

First, a gene of interest is fused to a gene encoding a polypeptide produced inherently in milk (such as goat β-casein) to thereby prepare a fusion gene. A DNA fragment containing this fusion gene is injected into a goat embryo, which is then implanted in the uterus of a female goat. The polypeptide of interest can be obtained from the milk produced by transgenic goats born from the goat which accepted the embryo or the offspring of the transgenic goats. In order to increase the yield of milk containing the polypeptide produced by the transgenic goats, hormones may be appropriately administered to the transgenic goats (Ebert, K. M. et al., Bio/Technology (1994) 12, 699-702).

Examples of insects which may be used include silkworm. In this case, silkworm is infected with baculovirus carrying a transferred gene encoding the polypeptide of interest. The polypeptide of interest can be obtained from the body fluid of the silkworm (Susumu, M. et al., Nature (1985) 315, 592-594).

Furthermore, when plants are used, tobacco can typically be used. When tobacco is used, a gene encoding the polypeptide of interest is inserted into a plant expression vector (e.g., pMON 530), which is then transferred into a bacterium such as *Agrobacterium tumefaciens*. A tobacco plant (e.g., *Nicotiana tabacum*) is infected with the resultant bacterium. The polypeptide of interest can be obtained from leaves of this plant (Julian, K.-C. Ma et al., Eur. J. Immunol. (1994) 24, 131-138).

The polypeptide thus obtained can be isolated from the inside of the host cell or from its outside (e.g., medium), and purified to a substantially pure and homogeneous polypeptide. Isolation and purification of polypeptides can be performed using conventional isolation and purification methods for polypeptides, and are not limited in any way. For example, polypeptides can be isolated and purified by appropriate selection and combination of various tools and techniques, such as chromatography columns, filters, ultrafiltration, salting-out, precipitation with solvent, extraction with solvent, distillation, immunoprecipitation, SDS-polyacrylamide gel electrophoresis, isoelectric focusing, dialysis, recrystallization, etc.

Examples of chromatography include affinity chromatography, ion exchange chromatography, hydrophobic chromatography, gel filtration, reverse-phase chromatography, adsorption chromatography, etc. (Strategies for Protein Purification and Characterization: A Laboratory Course Manual. Ed. Daniel R. Marshak et al., Cold Spring Harbor Laboratory Press, 1996). These chromatographic techniques can be carried out using liquid phase chromatography, for example, HPLC, FPLC, etc. The present invention also includes those polypeptides highly purified using these purification methods.

Before or after the purification, it is also possible to give optional modifications to the polypeptide or remove a partial peptide therefrom by reacting the polypeptide with an appropriate polypeptide modification enzyme. Examples of such enzyme include, but are not limited to, trypsin, chymotrypsin, lysyl endopeptidase, protein kinase and glucosidase.

The present invention also provides an antibody that binds to the polypeptide of the present invention. The form of the antibody of the present invention is not particularly limited; the antibody of the present invention includes polyclonal antibodies and monoclonal antibodies. In addition, antisera obtained by immunizing immune animals such as rabbit with the polypeptide of the present invention, and polyclonal antibodies and monoclonal antibodies of every class are also included in the antibody of the present invention.

The polypeptide used as a sensitizing antigen may be an intact polypeptide or a partial peptide thereof. Examples of such partial peptides include amino (N)-terminal fragments and carboxyl (C)-terminal fragments of the polypeptide. The term "antibody" as used herein means an antibody that reacts with the full length polypeptide or fragments thereof.

After inserting a gene encoding the polypeptide of the present invention or a fragment thereof into a known expression vector and transforming the host cell described earlier in this specification with this expression vector, the desired polypeptide or a fragment thereof is obtained from inside and outside of the host cells by a known method. This polypeptide or a fragment thereof may be used as a sensitizing antigen. Alternatively, cells expressing the polypeptide of the present invention or a lysate thereof, or a chemically synthesized polypeptide of the present invention may also be used as a sensitizing antigen.

Although there is no particular limitation on the species of mammals to be immunized with a sensitizing antigen, it is preferable to select mammals taking into consideration the compatibility with the parent cell to be used for cell fusion, and animals of the rodent, lagomorph and primate are generally used.

For example, mouse, rat, hamster and the like are used as rodent animals; rabbit is used as a lagomorphic animal, and monkey is used as a primate animal. Among monkeys, catarrhine monkeys (old world monkeys) are used, as exemplified by cynomolgus monkey (*Macaca fascicularis*), rhesus monkey, baboon, chimpanzee and the like.

Immunization of animals with a sensitizing antigen is carried out according to any known method. Generally, immunization is performed by intraperitoneal or subcutaneous injection of the antigen to mammals. Specifically, the antigen is appropriately diluted and suspended in PBS (Phosphate-Buffered Saline), physiological saline or the like, optionally mixed with a suitable amount of usual adjuvant (e.g., Freund's complete adjuvant), emulsified and then administered to mammals, preferably followed by several booster injections of the antigen mixed with an appropriate amount of Freund's incomplete adjuvant every 4 to 21 days. In addition, suitable carriers can be used at the time of immunization with the antigen. Subsequently, elevation of the level of a desired antibody in the sera of animals is confirmed by a conventional method.

In order to obtain polyclonal antibodies to the polypeptide of the present invention, the blood of mammals sensitized with the antigen is withdrawn after confirming elevation of the level of a desired antibody in sera. Then, sera are isolated from the blood by a known method. A serum containing a polyclonal antibody may be used as the polyclonal antibody. If necessary, a fraction containing the polyclonal antibody may be further isolated from the serum and used as the polyclonal antibody. For example, a fraction recognizing only the polypeptide of the present invention is obtained by using an affinity column to which the polypeptide of the present invention has been coupled, and further purified by using protein A or protein G column to prepare immunoglobulin G or M.

Monoclonal antibodies can be obtained by removing immunocytes from the mammals sensitized with the above-described antigen, after confirming the elevation of the level of a desired antibody in their sera, and then subjecting the immunocytes to cell fusion. Immunocytes preferably used for cell fusion are spleen cells. Parent cells to be fused to the above-described immunocytes are preferably mammalian myeloma cells, more preferably myeloma cells which have acquired characteristics for the selection of fused cells with drugs.

Cell fusion between the above-described immunocytes and myeloma cells can be carried out according to a known method, for example, the method of Milstein et al. (Galfre, G and Milstein, C., Methods Enzymol. (1981) 73, 3-46).

Hybridomas thus obtained by cell fusion are selected by culturing them in a conventional selection medium, for example, HAT culture medium (culture broth containing hypoxanthine, aminopterin and thymidine). Culturing in the HAT medium is continued for a sufficient time to kill other cells (non-fused cells) than desired hybridomas, usually for several days to several weeks. Then, conventional limiting culture-dilution method is performed to carry out screening and cloning of hybridomas producing the antibody of interest.

Subsequently, the resultant hybridomas are transplanted into the abdominal cavities of mice, and abdominal dropsies are collected from the mice to thereby obtain monoclonal antibodies. These monoclonal antibodies may be purified by ammonium sulfate precipitation, with protein A or protein G column, by DEAE ion exchange chromatography, with affinity column to which the polypeptide of the present invention has been coupled, etc. The antibody of the present invention can be used for purification and detection of the polypeptide of the present invention.

Further, the thus obtained monoclonal antibodies can also be prepared as recombinant antibodies using recombinant DNA techniques (see, for example, Borrebaeck, C. A. K. and Larrick, J. W., THERAPEUTIC MONOCLONAL ANTIBODIES, Published in the United Kingdom by MACMILLAN PUBLISHERS LTD, 1990). A recombinant antibody is produced by cloning a gene encoding the recombinant antibody from hybridomas or the antibody-producing immunocytes (such as sensitized lymphocytes), incorporating the gene into an appropriate vector, and transferring the vector into host cells for antibody production. The produced recombinant antibody is also included in the present invention.

The antibody of the present invention may be antibody fragments or modified antibodies as long as they are capable of binding to the polypeptide of the present invention. Examples of such antibody fragments include Fab, F(ab') 2, Fv, or a single-chain Fv (scFv) prepared by linking the Fv of H-chain to the Fv of L-chain via a suitable linker (Huston, J. S. et al., Proc. Natl. Acad. Sci. USA (1988) 85, 5879-5883). Specifically, antibody fragments are produced by digesting the antibody with enzymes, for example, papain or pepsin; or by constructing a gene encoding such a fragment, inserting the gene into an expression vector, and expressing it in a suitable host cell (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enymol. (1986) 121, 652-663; Rousseaux, J. et al., Methods Enzymol. (1986) 121, 663-669; Bird, R. E. and Walker, B. W., Trends Biotechnol. (1991) 9, 132-137).

As a modified antibody, the antibody bound to various molecules such as polyethylene glycol (PEG) may be also used. The "antibody" of present invention also includes these modified antibodies. These modified antibodies can be prepared by chemically modifying the antibody obtained as described above. These modification methods have been already established in the art.

Antibodies obtained as described above can be purified to homogeneity. For the isolation and purification of the antibody used in present invention, any methods of isolation and purification used for conventional polypeptides may be used. For example, chromatography columns such as affinity chromatography columns, filters, ultrafiltration, salting-out, dialysis, SDS-polyacrylamide gel electrophoresis, isoelectric focusing, etc. may be used independently or in appropriate combinations (Antibodies: A Laboratory Manual. Ed Harlow and David Lane, Cold Spring Harbor Laboratory, 1988) but these are not the sole examples. Concentration of the antibody obtained as described above can be determined by measuring absorbance or by a method such as enzyme-linked immunosorbent assay (ELISA).

Examples of columns used in affinity chromatography include protein A column and protein G column. As columns using protein A, Hyper D, POROS, Sepharose F. F. (Pharmacia), etc. may be given.

Examples of chromatography other than affinity chromatography include ion exchange chromatography, hydrophobic chromatography, gel filtration, reversed-phase chromatography, adsorption chromatography, etc. (Strategies for Protein Purification and Characterization: A Laboratory Course Manual. Ed Daniel R. Marshak et al., Cold Spring Harbor Laboratory Press, 1996). These chromatographic techniques can be carried out using liquid phase chromatography such as HPLC, FPLC, etc.

Furthermore, absorbance measurement, ELISA, EIA (enzyme immunoassay), RIA (radioimmunoassay) or fluorescent antibody technique can be used as methods for measuring the antigen-binding activity of the antibody of present invention. When ELISA is used, the polypeptide of the present invention is added to plates on which the antibody of the present invention has been immobilized, and then a sample containing an antibody of interest (e.g., culture supernatant of antibody-producing cells or purified antibody) is added to the plates. A secondary antibody labeled with an enzyme (e.g., alkaline phosphatase) that recognizes the antibody is added to the plates. After incubating and washing the plates, a substrate for the enzyme (e.g., p-nitrophenyl phosphate) is added to determine the absorbance to thereby evaluate the antigen-binding activity. Instead of the entire polypeptide, a fragment thereof may be used. For example, fragments comprising its C-terminal or N-terminal may be used. For evaluating the activity of the antibody of the present invention, BIAcore (Pharmacia) may be used.

In one aspect, the present invention provides a method for producing a desired polypeptide, which is characterized in that cells capable of high-yield production of β-alanine and into which a desired polypeptide has been introduced, are cultured to increase the intracellular concentration of β-alanine in the cells during the culture, thereby improving production of the desired polypeptide.

The term “cells capable of high-yield production of β-alanine” is used herein to mean: cells in which the ratio of the intracellular concentration of β-alanine on the $6^{th}$ or subsequent days after the initiation of the culture to that at the initiation of the culture is 2 or greater, and preferably 5 or greater; or cells which are capable of increasing the β-alanine concentration in the culture medium on the $6^{th}$ or subsequent days after the initiation of the culture by 50 μM or more, and preferably by 100 μM or more.

As a method of measuring the ratio of two intracellular concentrations of β-alanine, the following method may be applied. Samples are collected at appropriate times from a culture medium containing cells in a 1-L jar feeding culture tank, such that the number of cells per sample is 50 to $500\times10^5$, preferably 100 to $450\times10^5$, and most preferably approximately $200\times10^5$. The collected samples are centrifuged, and the obtained culture supernatants are isolated as samples for use in the subsequent measurement of amino acids in the culture medium. Thereafter, 1 ml of cooled sterile water having a protease inhibitor (Complete Mini; Roche Diagnostics; Protease inhibitor cocktail tablets) dissolved therein is added to the cell pellets, which are then pulsed on ice for 5 seconds using an ultrasonic cell disruptor (MISONIX ASTRASON MODEL XL2020), and such pulsing operation is then suspended for 5 seconds. This cycle is defined as one set of treatment, and a total of 12 sets of treatment are carried out, so as to completely disrupt the cells. The total amount of the solution after the treatment is applied to a centrifugal filtration unit to prepare filtrates with molecular weights of 5000 and less. The filtrates are used as samples for the measurement of intracellular amino acids. The absorbance at 570 nm of each sample is detected using a ninhydrin test solution-L 8500 set (Wako Pure Chemical Industries, Ltd.) and an improved model of a fully automatic amino acid analyzer (L-8500) manufactured by Hitachi, Ltd., and the obtained values are then compared with one another. Thus, the concentrations of various amino acids in the samples are determined. The concentration of β-alanine in the culture medium is directly measured. Thus, the determined concentrations are compared with one another on the μM order. Now consider the concentration of intracellular β-alanine. Since 1 mL of cooled sterile water has been added to the cell pellets, followed by ultrasonic cell disruption, the detection value of intracellular β-alanine derived from the CSAD strongly expressing strain at the initiation of the culture is defined as 1, and this detection value is compared with the detection values for each of the strongly expressing strains at the initiation of the culture, and on the $6^{th}$ and $12^{th}$ days after the initiation of the culture, so that each ratio is obtained. It is to be noted that the aforementioned culture is preferably carried out with 1 to $10\times10^5$ cells/mL in an initial stage. In an exemplary method of measuring the concentration of β-alanine in a culture medium, culture may be carried out in a 1-L jar feeding culture tank, under the condition of approximately $2\times10^5$ cells/mL in an initial stage and the concentration of β-alanine in the culture medium may be measured over time.

Alternatively, is another method of measuring the concentration of β-alanine in a culture medium, a culture supernatant may be measured using an amino acid analyzer, as described above.

In order to increase the amount of β-alanine produced in the cultured cells, a gene of a polypeptide having a function of accumulating intracellular β-alanine such as a protein having enzyme activity for synthesizing β-alanine from aspartic acid, may be expressed strongly, preferably by introducing DNA encoding the aforementioned gene into the cells.

Such proteins having enzyme activity for synthesizing β-alanine from aspartic acid include cysteine sulfinic acid decarboxylase, glutamate decarboxylase (GAD) (EC. 4.1.1.15), aspartate 1-decarboxylase (EC. 4.1.1.1), and the like.

Cells in which the intracellular concentration of β-alanine has been increased include cells into which DNA encoding cysteine sulfinic acid decarboxylase, glutamate decarboxylase (GAD), aspartate 1-decarboxylase (EC. 4.1.1.1), or a mutant thereof has been introduced.

A specific example of the cell of the present invention that are capable of high-yield production of β-alanine is cells in which the ratio of the concentration of intracellular β-alanine on the $6^{th}$ or subsequent days after the initiation of the culture to that at the initiation of the culture is 2 or greater, or the ratio of the concentration of intracellular β-alanine on the $12^{th}$ or subsequent days after the initiation of the culture to that at the initiation of the culture is 5 or greater, as measured by the same method as that described later in Examples.

Another specific example of the cells of the present invention that are capable of high-yield production of β-alanine is cells which are capable of increasing the β-alanine concentration in the culture medium on the $6^{th}$ or subsequent days after the initiation of the culture by 50 μM or more, and preferably by 100 μM or more, as measured by the same method as that described later in Examples.

In another aspect, the present invention provides a cultured cell in which the ratio of the intracellular concentration of β-alanine on the $6^{th}$ or subsequent days after the initiation of the culture to that at the initiation of the culture is 2 or greater.

In a further aspect, the present invention provides a cultured cell which is capable of increasing the β-alanine concentration in the culture medium on the $6^{th}$ or subsequent days after the initiation of the culture by 50 μM or more, and preferably by 100 μM or more.

In the present invention, the concept of “cells into which DNA has been transferred” encompasses not only cells into which exogenous DNA has been incorporated by genetic recombination technology; but also cells in which endogenous DNA has been activated by gene activation technology (see, for example, International Publication WO94/12650) so that expression of a protein corresponding to the endogenous DNA or transcription of the DNA has been initiated or increased.

EXAMPLES

Hereinbelow, the present invention will be described in more detail with reference to the following Examples. It should be noted that these Examples are provided only for illustrating the present invention and not for limiting the scope of the present invention.

Example 1

Cloning of CHO Cell-Derived Hamster Cysteine Sulfinic Acid Decarboxylase (CSAD) and Cysteine Dioxygenase, Type I (CDO1) Genes Total RNA was extracted from anti-IL-6 receptor antibody-producing cells (A CHO DXB11 cell line into which an anti-IL-6 receptor antibody gene had been transferred) (Japanese Unexamined Patent Publication No. Hei 8-99902), and then cDNA was synthesized therefrom in a poly(A) dependent manner. Hamster CSAD and CDO1 genes were obtained by PCR using as a template the cDNA fragmented with three restriction enzymes, SalI, XhoI and EcoRI. As PCR primers, those containing the 5'-end and the 3'-end sequence conserved between rat and mouse CSADs or CDO1s were designed. The nucleotide sequences of the cloned genes were determined. From its homology with other CSAD or CDO1 genes of known species, the cloned gene was confirmed to encode hamster CASD (FIG. 1) or CDO1 (FIG. 2). The amino acid sequence of hamster CSAD has high homology with the known amino acid sequences of mouse CSAD (96% identity), rat CSAD (96% identity) and human CSAD (91% identity); it was predicted that hamster CSAD is an enzyme having the same activity. The amino acid sequence of hamster CDO1 has high homology with the known amino acid sequences of mouse CDO1 (99% identity), rat CDO1 (98% identity) and human CDO1 (93% identity); it was predicted that hamster CDO1 is an enzyme having the same activity. The nucleotide sequences of hamster, rat, mouse and human CSAD are shown in SEQ ID NOs: 1, 3, 5 and 7, respectively. The amino acid sequences of hamster, rat, mouse and human CSAD are shown in SEQ ID NOs: 2, 4, 6 and 8, respectively. The nucleotide sequences of hamster, rat, mouse and human CDO1 are shown in SEQ ID NOs: 9, 11, 13 and 15, respectively. The amino acid sequences of hamster, rat, mouse and human CDO1 are shown in SEQ ID NOs: 10, 12, 14 and 16, respectively. The nucleotide and amino acid sequences of bovine CDO1 are shown in SEQ ID NOs: 17 and 18, respectively.

Example 2

Figure 4:
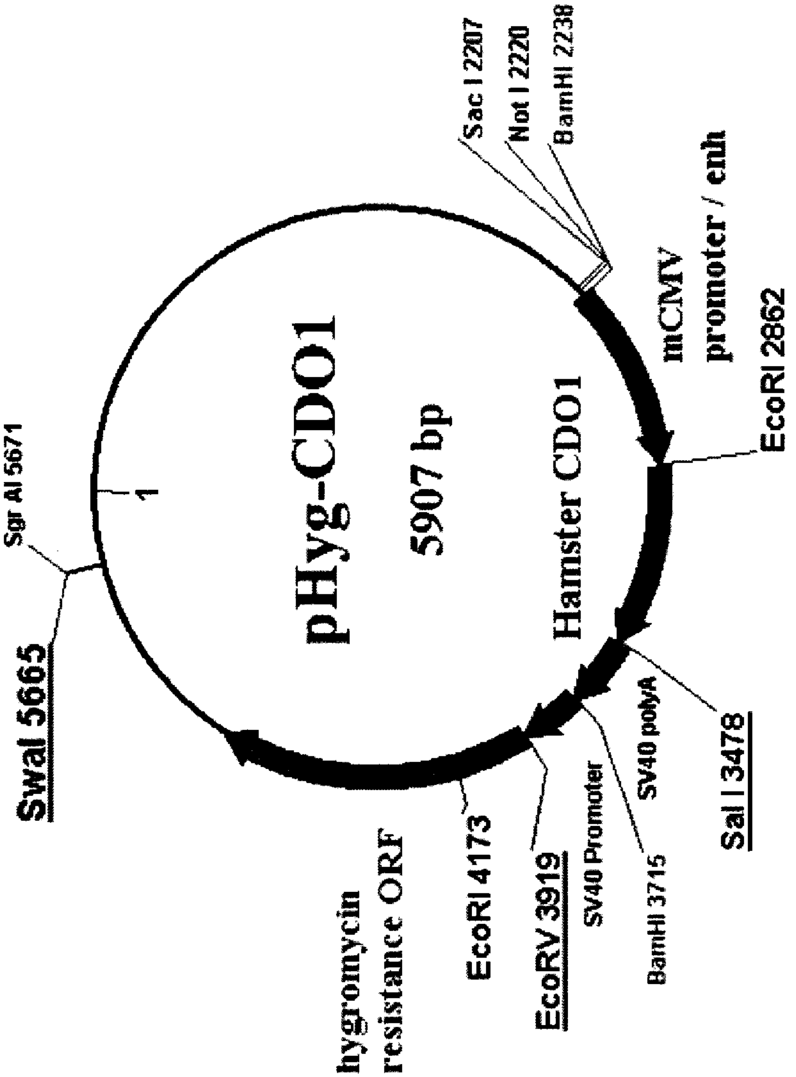
FIG. 4 shows a plasmid which was used for expressing hamster CDO1 (200 amino acids).
Figure 5:
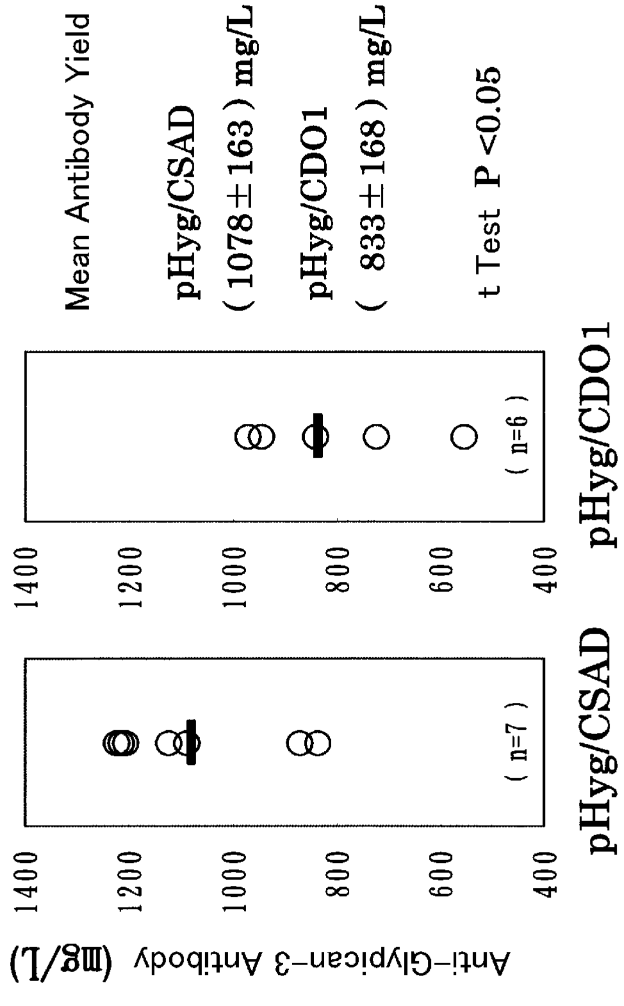
FIG. 5 shows anti-glypican-3 antibody yield plots on day 14 of 50 ml shaker flask fed-batch culture.
Figure 6:
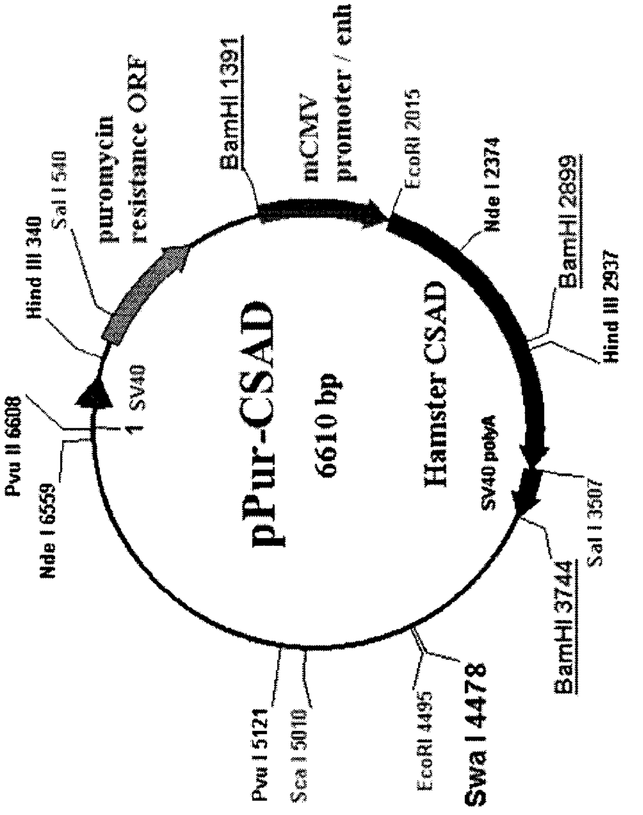
FIG. 6 shows a plasmid which was used for expressing Hamster CSAD (493 amino acids) in a TauT strongly expressing strain.
Figure 7:
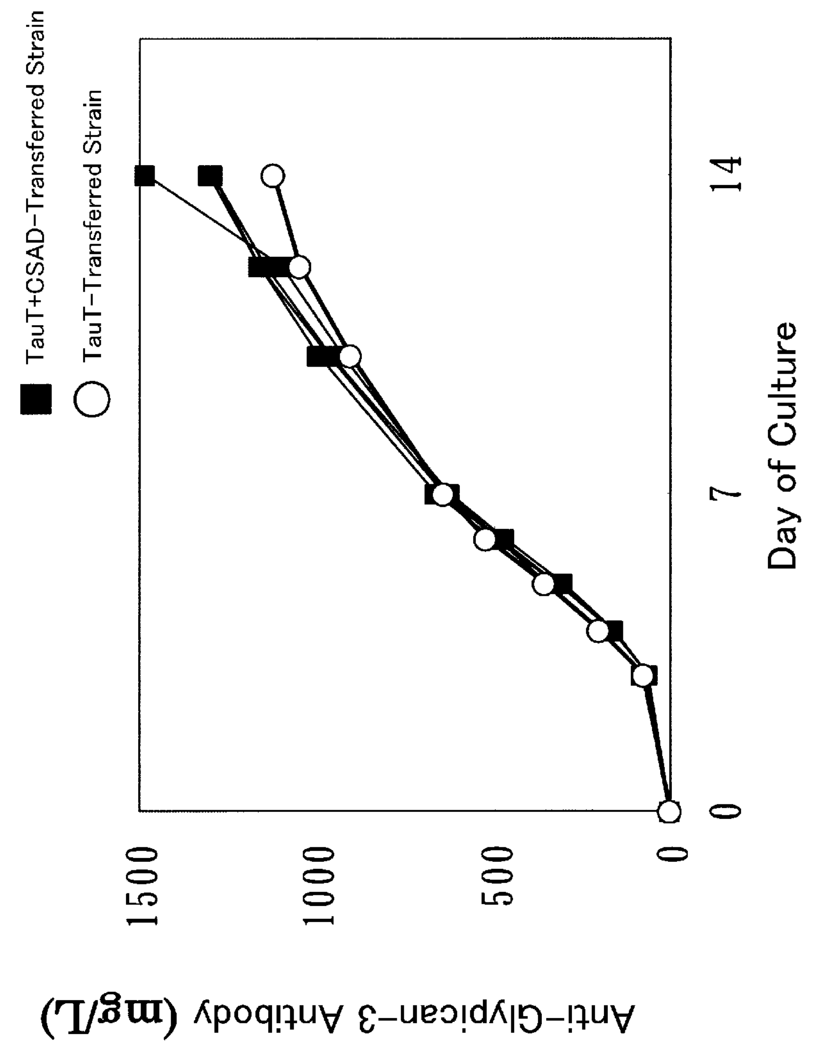
FIG. 7 is a graph showing the amounts of antibodies produced in the feeding cultures of four pPur/CSAD-transferred TauT strongly expressing strains and TauT strongly expressing cells as a parent strain in 50-ml shakers.
Figure 9:
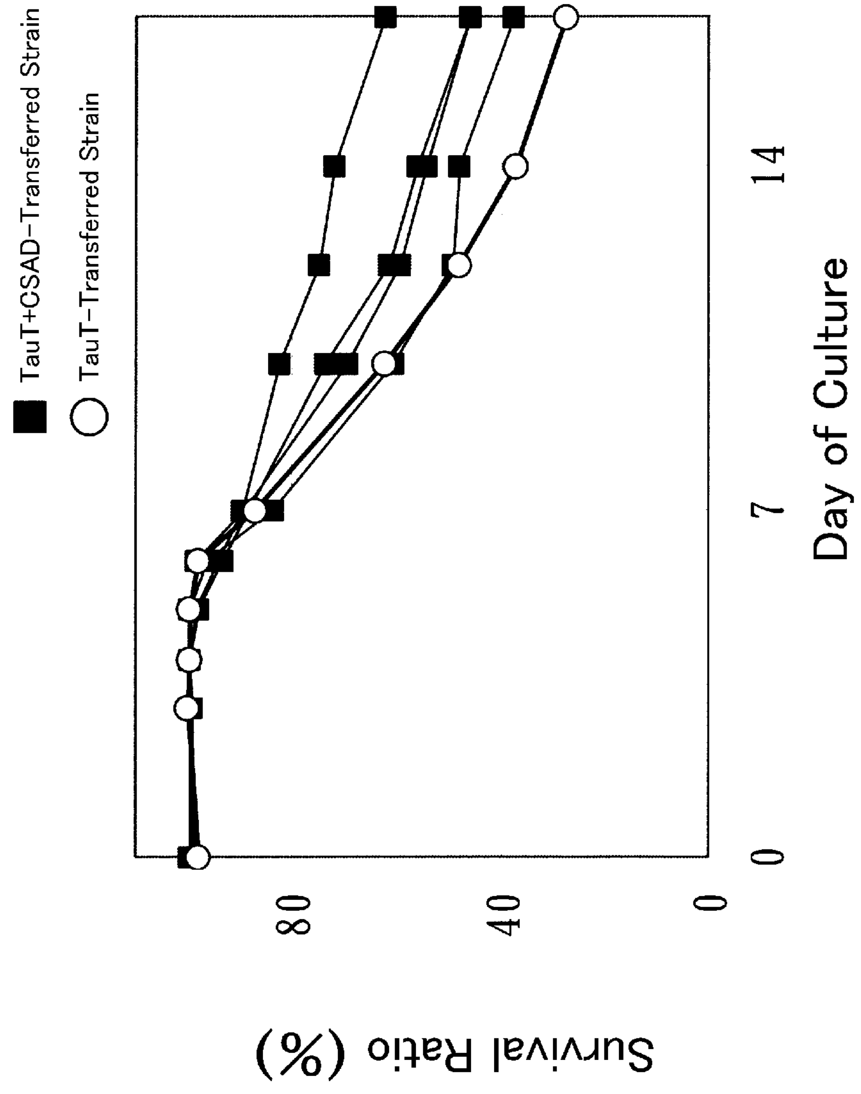
FIG. 9 is a graph showing the survival ratio of the cells in the feeding cultures in 50-ml shakers. The survival ratio was maintained in the pPur/CSAD-transferred TauT strongly expressing strains.
Figure 10:
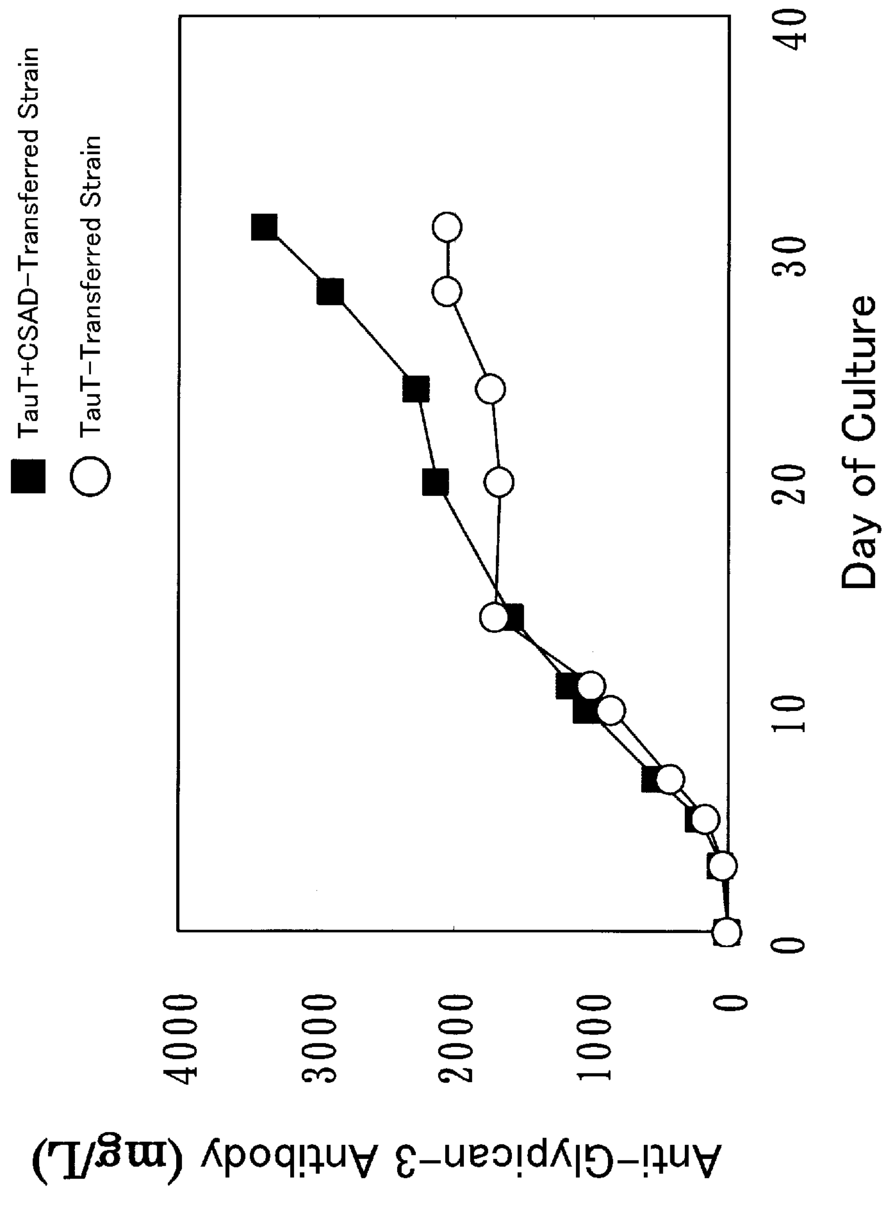
FIG. 10 is a graph showing the amount of an antibody produced in the feeding culture in a 1-L jar of the pPur/CSAD-transferred TauT strongly expressing strain that shows the highest survival ratio in FIG. 9.

Increase in Antibody Yield, Inhibition of Lactate Production and Maintenance of Survival Ratio, as Caused by Transfer of Hamster CSAD CMV promoter expression plasmid pHyg/CSAD (FIG. 3) or pHyg/CDO1 (FIG. 4) was constructed by adding Kozak sequence to the hamster CSAD (hereinafter, CSAD) or the hamster CDO1 (hereinafter, CDO1) gene obtained by cloning in Example 1. The plasmid pHyg/CSAD or pHyg/CDO1 was introduced by electroporation into the parent strain anti-glypican-3 antibody producing CHO cell (see WO 2006/006693). After selection of expression plasmid-transferred cells in the presence of hygromycin (200 μg/ml), all of the stably growing cell strains were expanded (pHyg/CSAD: 7 strains; pHyg/CDO1: 6 strains). The mRNA expression levels of CSAD and CDO1 were quantified by a TaqMan method. The two strains were confirmed to express mRNA at levels superior to that with the parent strain (in both CSAD and CDO1, the mRNA expression was 200 times or greater than that of the parent strain). The aforementioned cells ($2\times10^5$ cells/mL in an initial stage) were subjected to feeding culture in a 50-ml shaker. A comparison was made for the amount of an anti-glypican-3 antibody generated on the $14^{th}$ day at the late stage of the culture. The amount of the antibody produced in pHyg/CSAD-transferred cells was significantly higher than that in pHyg/CDO1-transferred cells (t-test: $p<0.05$) (FIG. 5). This result suggests that a strain capable of high-yield antibody production can be obtained by artificially expressing hamster CSAD. Subsequently, in anticipation of a synergistic effect that might be obtained by introduction of CSAD and TauT, pPur/CSAD (FIG. 6) was constructed and then introduced by electroporation into the pHyg/TauT-transferred cells (T10) prepared in Reference example 2. Selection was carried out in the presence of puromycin (6 μg/ml), and four stably growing strains were then amplified (pHyg/TauT+pPur/CSAD:TauT+CSAD-transferred strains). The mRNAs expression levels of TauT and CSAD in the 4 strains were quantified by a TaqMan method. As a result, strong expression of TauT and CSAD was confirmed in all the strains (expression of TauT mRNA in the 4 strains was almost at the same level as that of the parent TauT-transferred strain, and expression of CSAD mRNA in the 4 strains was 130 to 580 times higher than that of the TauT-transferred strain). The TauT-transferred strain was compared for culture profile with the TauT+CSAD-transferred strain by feeding culture of the cells in a 50-ml shaker ($2\times10^5$ cells/mL in an initial stage). As FIG. 7 shows, the average amount of an anti-glypican-3 antibody produced on the $14^{th}$ day at the late stage of culture in the TauT+CSAD-transferred strain (1343 mg/L) was higher than that in the TauT-transferred strain (1122 mg/L). Moreover, in terms of suppression of lactate production (FIG. 8) and retention of the survival ratio (FIG. 9) as well, the TauT+CSAD-transferred strain showed a higher potential. Furthermore, in order to confirm high potential in the amount of an antibody produced, the TauT+CSAD-transferred strain showing the highest survival ratio in FIG. 9 and the TauT-transferred strain were subjected to feeding culture in a 1-L jar (FIG. 10). A significant difference in the amount of an antibody produced on the $31^{st}$ day of the culture was observed between the two types of strains (TauT-transferred strain: 2050 mg/L; TauT+CSAD-transferred strain: 3383 mg/L). The amount of an antibody produced in the CSAD-transferred strain was 2170 mg/L. Moreover, since the survival ratio of a strain into which neither type of genes had been-transferred was low at the late stage of the culture, the maximum value of the amount of an antibody produced was 2006 mg/L on the $14^{th}$ day of the culture.

Figure 11A:
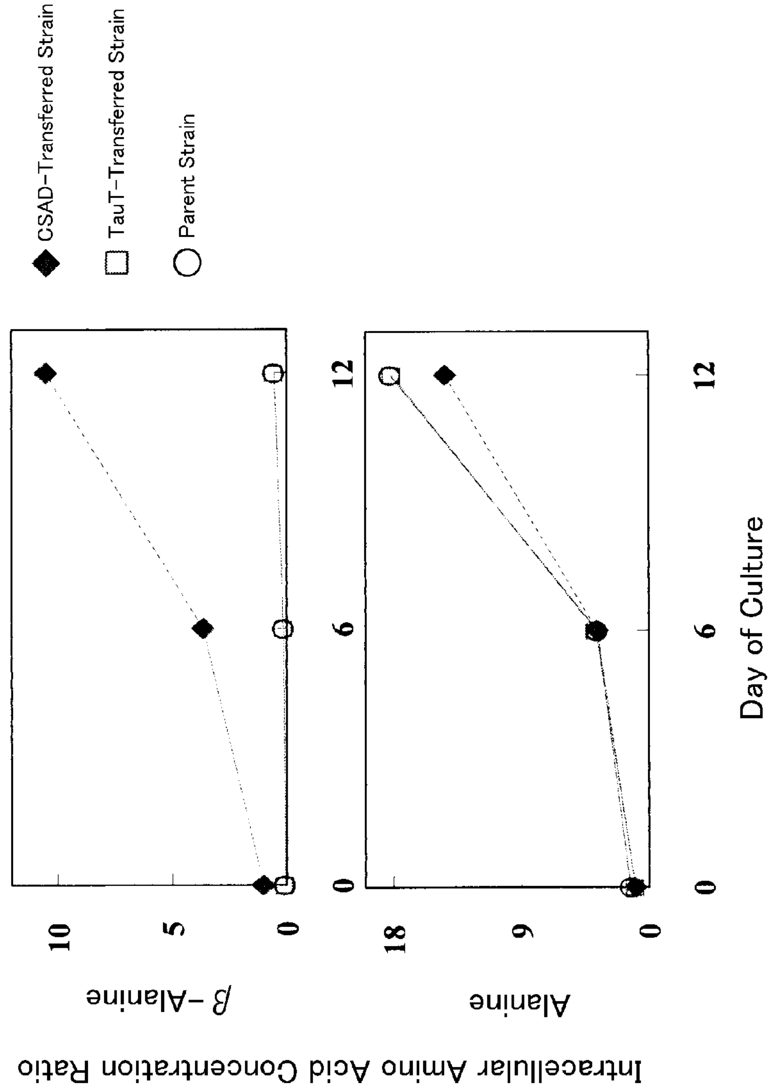
FIG. 11*a* is a graph showing the contents (concentration ratios) of intracellular alanine and intracellular β-alanine during feeding cultures in 1-L jars.
Figure 11B:
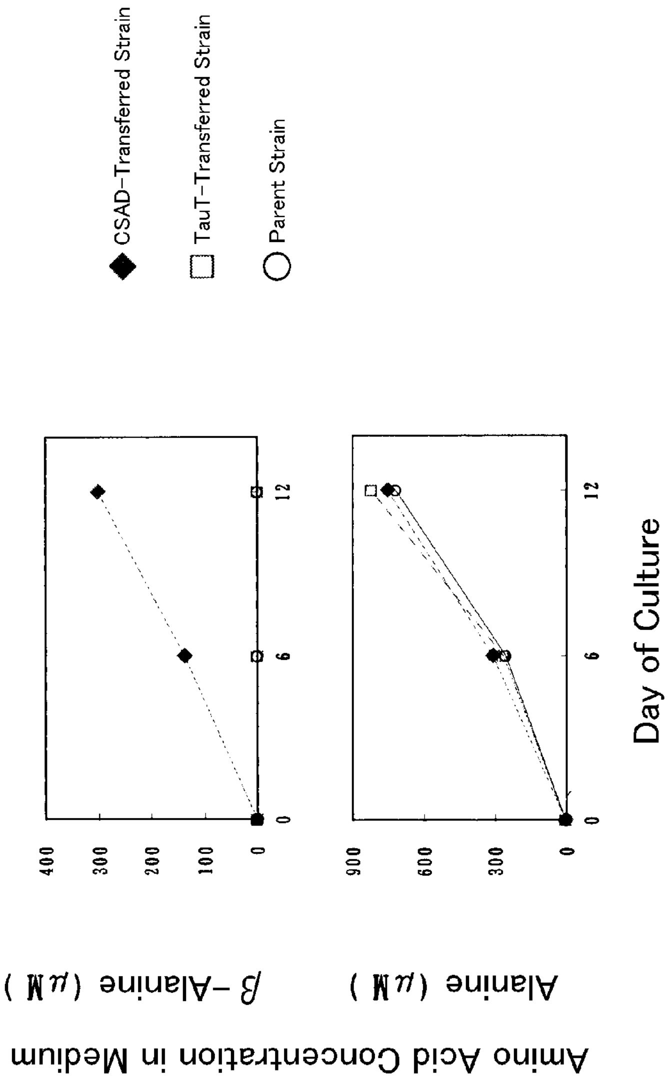
FIG. 11*b* is a graph showing the concentrations of alanine and β-alanine in the culture media during feeding cultures in 1-L jars.
Figure 13:
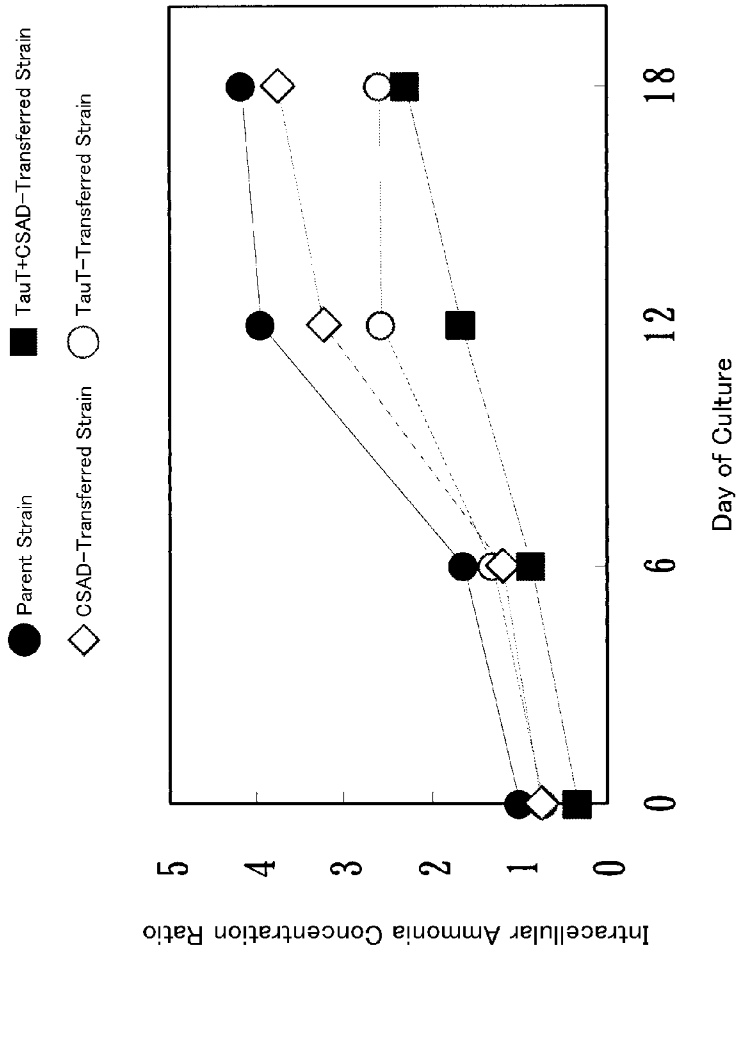
FIG. 13 is a graph showing the content (concentration ratio) of intracellular ammonia during feeding cultures in 1-L jars. Ammonia generation in the pPur/CSAD-transferred TauT strongly expressing strain was significantly suppressed, as compared with the parent strain.

In order to examine the effect of a CSAD strongly expressing strain, four strains (into which 4 different genes had been introduced) were cultured in a 1-L jar feeding culture tank ($2\times10^5$ cells/mL in an initial stage). The culture medium was collected at appropriate times. ($450\times10^5$ cells were collected from each of the parent strain, TauT-transferred strain, and CSAD-transferred strain, and $200\times10^5$ cells were collected from the TauT+CSAD-transferred strain. As a result, with regard to intracellular concentration, only the measurement value for the TauT+CSAD-transferred strain was corrected by multiplying by 2.25, and the thus corrected value was used.) The collected culture media were centrifuged to give culture supernatants used as samples for use in the subsequent measurement of amino acids in the culture medium. Thereafter, 1 ml of cooled sterile water having a protease inhibitor (Complete Mini; Roche Diagnostics; Protease inhibitor cocktail tablets) dissolved therein was added to the cell pellets, which were then pulsed on ice for 5 seconds using an ultrasonic cell disruptor (MISONIX ASTRASON MODEL XL2020). Such pulsing operation was then suspended for 5 seconds. This cycle was defined as one set of treatment, and a total of 12 sets of treatment were carried out, so as to completely disrupt the cells. The total amount of the solution after the treatment was applied to a centrifugal filtration unit to prepare filtrates with molecular weights of 5000 and less. The filtrates were used as samples for the measurement of intracellular amino acids. The absorbance at 570 nm of each sample was detected using a ninhydrin test solution-L 8500 set (Wako Pure Chemical Industries, Ltd.) and an improved model of a fully automatic amino acid analyzer (L-8500) manufactured by Hitachi, Ltd., and the obtained values were then compared with one another. Thus, the concentrations of various amino acids in the samples were determined. The concentrations of various amino acids and ammonia in the culture medium were directly measured. Thus, the determined concentrations were compared with one another on the μM order. With regard to intracellular concentration, since 1 mL of cooled sterile water was added to the cell pellets, followed by ultrasonic cell disruption, the measurement values of various amino acids and ammonia were converted to values per cell, and the thus converted values were compared with one another (FIGS. 11 and 13). With regard to the amino acid concentration ratio shown in FIG. 11*a*, the detection value of intracellular β-alanine (in $450\times10^5$ cells) derived from the CSAD strongly expressing strain at the initiation of the feeding culture in a 1-L jar was defined as 1, and this detection value was compared with the detection values for each strongly expressing strain at the initiation of the culture and on the $6^{th}$ and $12^{th}$ days after the initiation of the culture, so that each ratio was obtained. With regard to the ammonia concentration ratio shown in FIG. 13, the detection value of ammonia in the parent strain (in $450\times10^5$ cells) at the initiation of the feeding culture in a 1-L jar was defined as 1, and this detection value was compared with the detection values at the initiation of the culture and on the $6^{th}$, $12^{th}$, and $18^{th}$ days after the initiation of the culture, so that each ratio was obtained. Moreover, changes over time in the concentrations of alanine and β-alanine in the culture medium during the culture were also measurement values derived from the aforementioned amino acid analysis.

Figure 8:
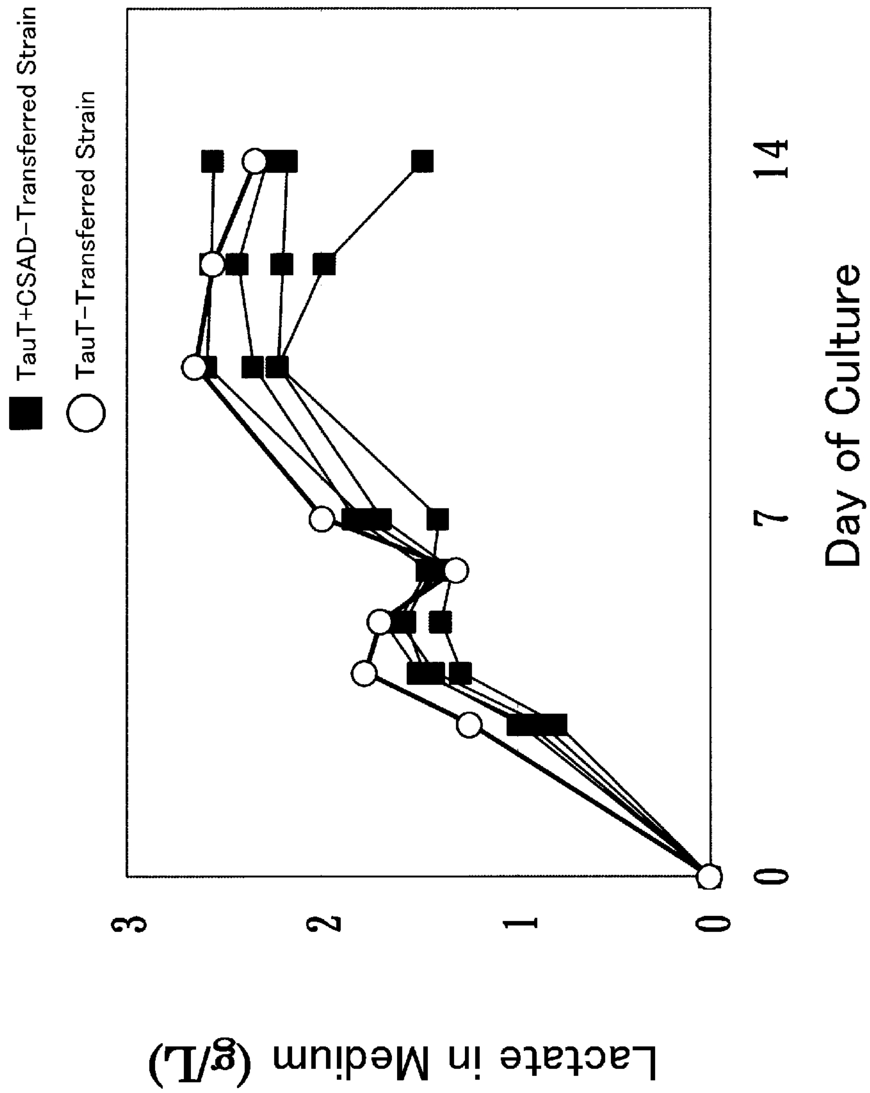
FIG. 8 is a graph showing the amount of lactate produced in the feeding cultures in 50-ml shakers. Suppressed the production of lactate was observed in the pPur/CSAD-transferred TauT strongly expressing strains.
Figure 12:
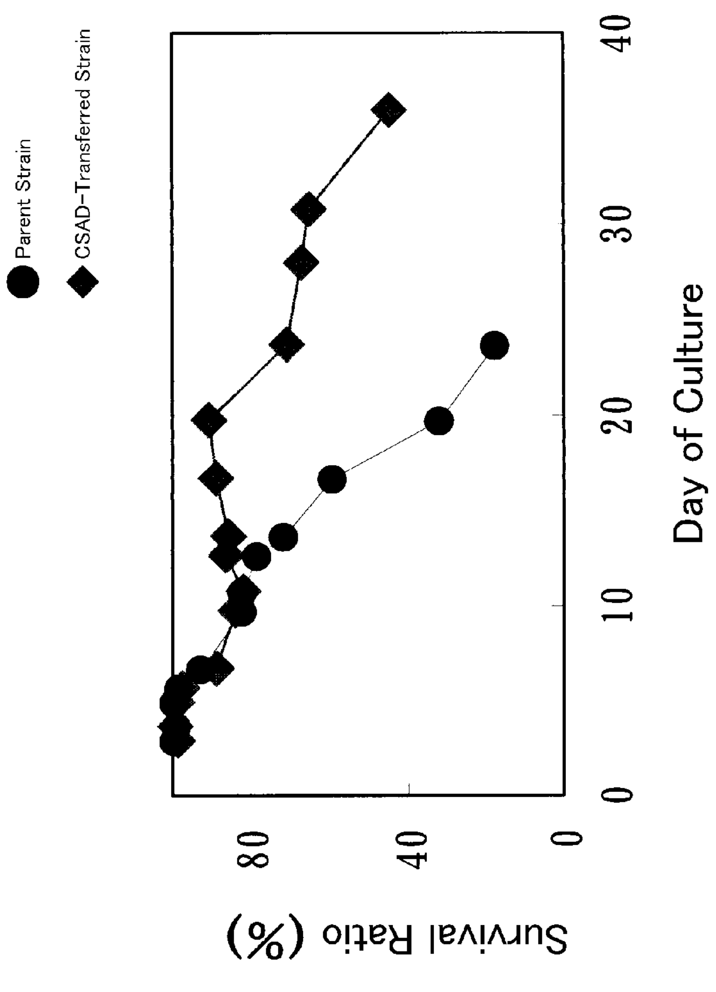
FIG. 12 is a graph showing the survival ratio of the cells in feeding cultures in 1-L jars. The pPur/CSAD-transferred cells maintained their survival ratio in comparison with the parent strain.

As a result, no significant differences in intracellular amino acid concentration were observed by almost all amino acids among various types of gene-transferred strains. Only pHyg/CSAD, a CSAD strongly expressing strain, produced a high-yield of β-alanine that was not contained in the medium. This was also clear from the fact that when the concentrations of β-alanine and alanine in the culture medium were measured during the culture, the concentration of β-alanine significantly increased in the culture medium of the CSAD strongly expressing strain (FIG. 11*b*). β-alanine is an organic osmolyte that acts to regulate osmotic pressure, and it has pH-buffering action and antioxidant action by itself. In addition, since such β-alanine is a precursor of carnosine (β-alanyl-L-histidine) which has a potent antioxidant activity, it can neutralize the fatigue substance lactate by its antioxidant action. Suppression of the amount of lactate produced as shown in FIG. 8 is considered to be brought about by β-alanine effect. Such β-alanine effect of the CSAD strongly expressing strain was significant in terms of survival ratio in feeding cultures in 1-L jar (FIG. 12). Moreover, intracellular ammonia in the TauT+CSAD-transferred strain was maintained at low concentration (FIG. 13), which is considered to contribute to high-yield production of antibodies.

The present invention can be applied to all types of antibody-producing cells.

Example 3

Survival Ratio-Maintaining Effect in the Presence of β-Alanine

Figure 14:
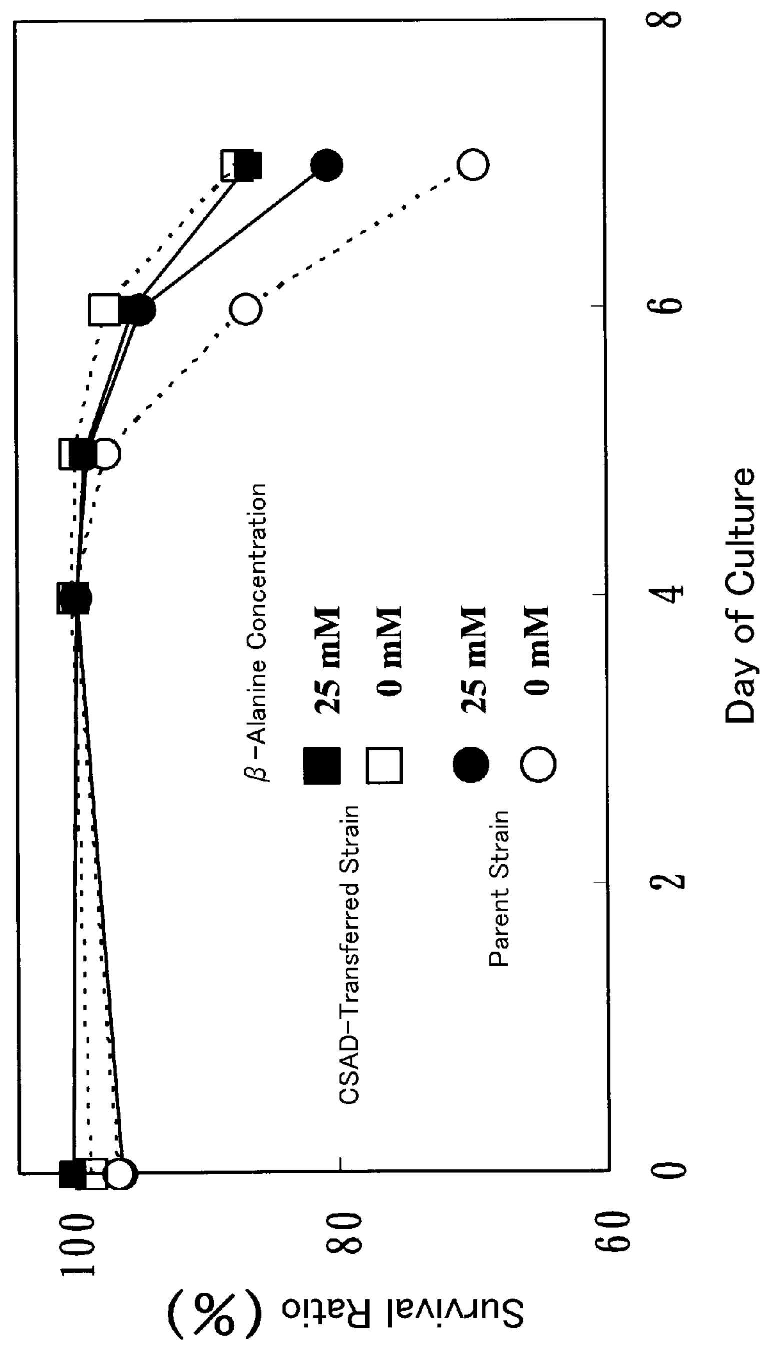
FIG. 14 is a graph showing the survival ratio of the cells in batch cultures in 50-ml shakers. As a result of addition of β-alanine (25 mM) to the parent strain, the survival ratio of the parent strain was maintained at levels equivalent to that of a CSAD-transferred strain capable of high-yield production of β-alanine.
Figure 15:
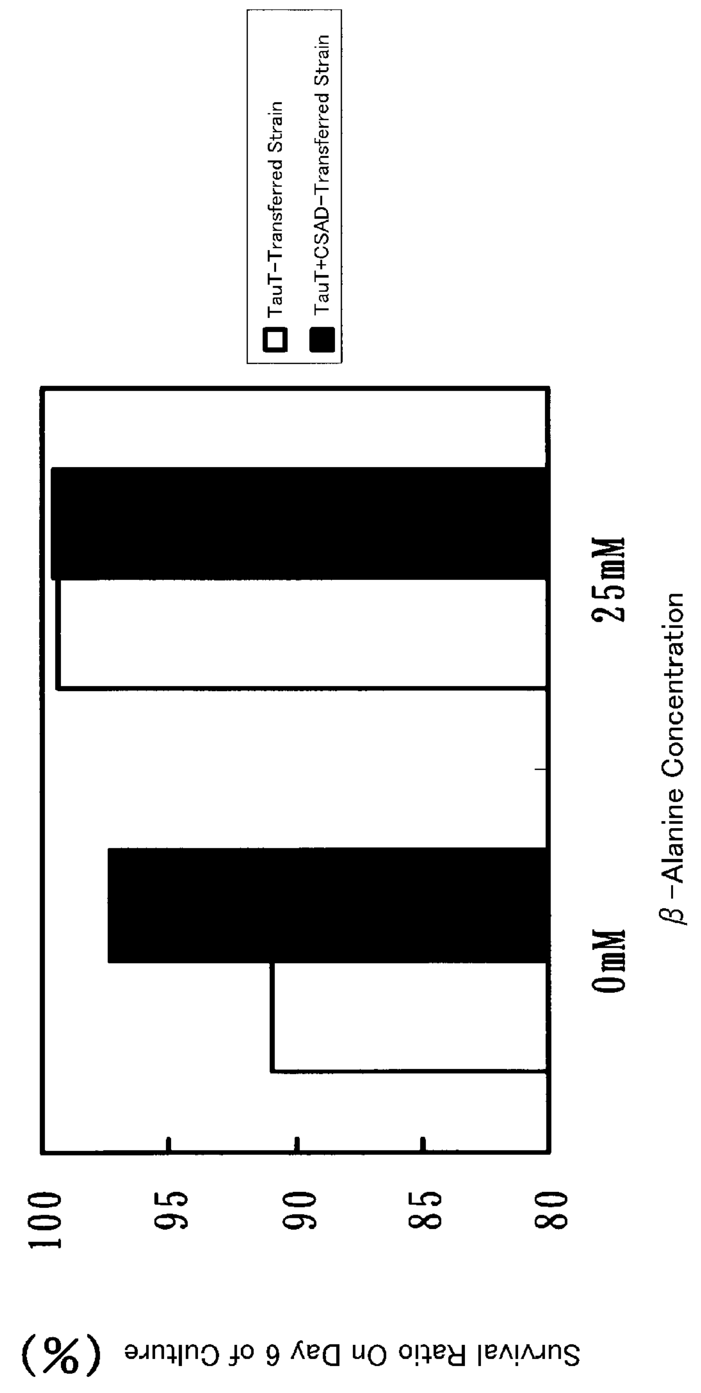
FIG. 15 is a graph showing the survival ratio of the cells on the $6^{th}$ day of batch cultures in 50-ml shakers. As a result of addition of β-alanine (25 mM) to the TauT-transferred strain, the survival ratio of the TauT-transferred strain was maintained at a level equivalent to that of a TauT+CSAD-transferred strain capable of high-yield production of β-alanine.

The parent strain and the CSAD-transferred strain were subjected to batch culture in a 50-ml shaker ($2\times10^5$ cells/mL in an initial stage) in the presence or absence of β-alanine (25 mM), and a comparison was made for their survival ratio. As FIG. 14 shows, on the $6^{th}$ day of the culture, the survival ratio of the CSAD-transferred strain capable of high-yield production of β-alanine was maintained in the absence of β-alanine (0 mM). In contrast, on the $6^{th}$ day of the culture, the survival ratio of the parent strain in capable of high-yield production of β-alanine decreased in the absence of β-alanine. The survival ratio of the parent strain on the $6^{th}$ day of the culture was maintained in the presence of β-alanine (25 mM), demonstrating the survival ratio maintaining effect of addition of β-alanine. However, from the survival ratio of the CSAD-transferred strain on the $7^{th}$ day of the culture, it was found that the survival ratio of the strain that became capable of high-yield production produced a large amount of β-alanine in the cells was maintained even in the absence of β-alanine (0 mM) at a level higher than that for the parent strain in the medium to which 25 mM β-alanine was added. Further, as shown in FIG. 15, even in the case where CSAD was co-transferred into a TauT-transferred strain to synthesize β-alanine in the cells, the survival ratio of the strain on the $6^{th}$ day of the culture was maintained in the absence of β-alanine (0 mM). On the other hand, as in the case of the parent strain of FIG. 14, a strain into which TauT was transferred but CSAD was not co-transferred maintained the survival ratio on the $6^{th}$ day of the culture in the presence of β-alanine (25 mM). There results demonstrate the survival ratio-maintaining effect of β-alanine that acts in cells. Thus, the results also demonstrate that the culture of cells capable of high-yield production of β-alanine is superior to the mere addition of β-alanine to a medium for cell culture in terms of the maintenance of the survival ratio of the cells or an increase in the yield of a desired polypeptide produced. Accordingly, the cell of the present invention which is capable of high-yield production of β-alanine is useful as a cell for producing all types of polypeptides such as an antibody or a physiologically active protein.

Reference Example 1

Cloning of CHO Cell-Derived Hamster Taurine Transporter Gene

Figure 17:
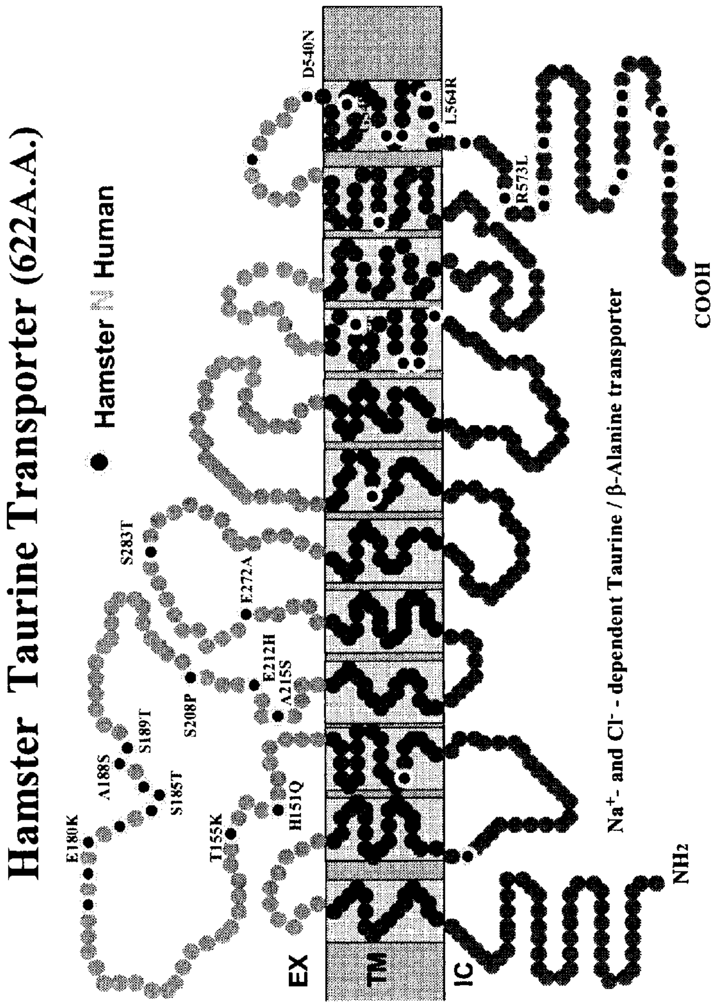
FIG. 17 is a taurine transporter membrane topology of a newly cloned, CHO cell-derived hamster TauT.

Total RNA was extracted from anti-IL-6 receptor antibody-producing cells (A CHO DXB11 cell line into which an anti-IL-6 receptor antibody gene had been transferred) (Japanese Unexamined Patent Publication No. Hei 8-99902), and then cDNA was synthesized therefrom in a poly(A) dependent manner. Hamster taurine transporter (TauT) gene was obtained by PCR using as a template the cDNA fragmented with three restriction enzymes, SalI, XhoI and EcoRI. As PCR primers, those containing the 5'-end and the 3'-end sequence conserved between rat and mouse TauTs were designed. The nucleotide sequence of the cloned gene was determined. From its homology with other TauT genes of known species, the cloned gene was confirmed to encode hamster TauT (FIG. 16). The amino acid sequence of hamster TauT has high homology with mouse TauT (96% identity), rat TauT (96% identity) and human TauT (93% identity); it was predicted that hamster TauT is a transporter with 12 transmembrane regions (FIG. 17).

Reference Example 2

Figure 18:
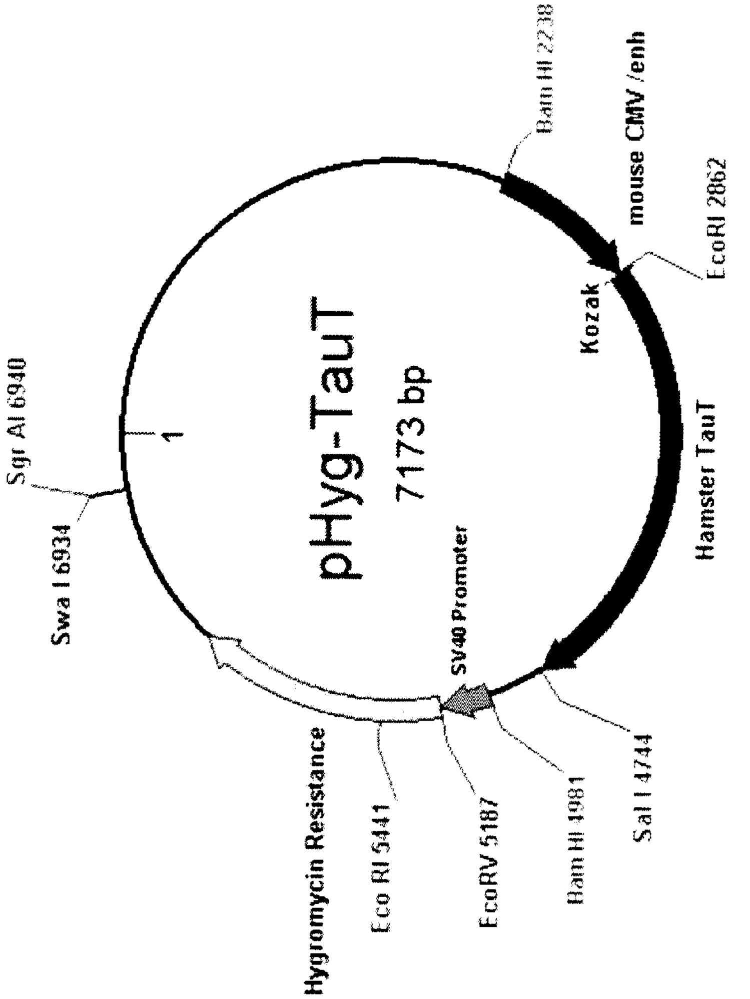
FIG. 18 shows a plasmid which was used for expressing hamster TauT (622 amino acids).
Figure 19:
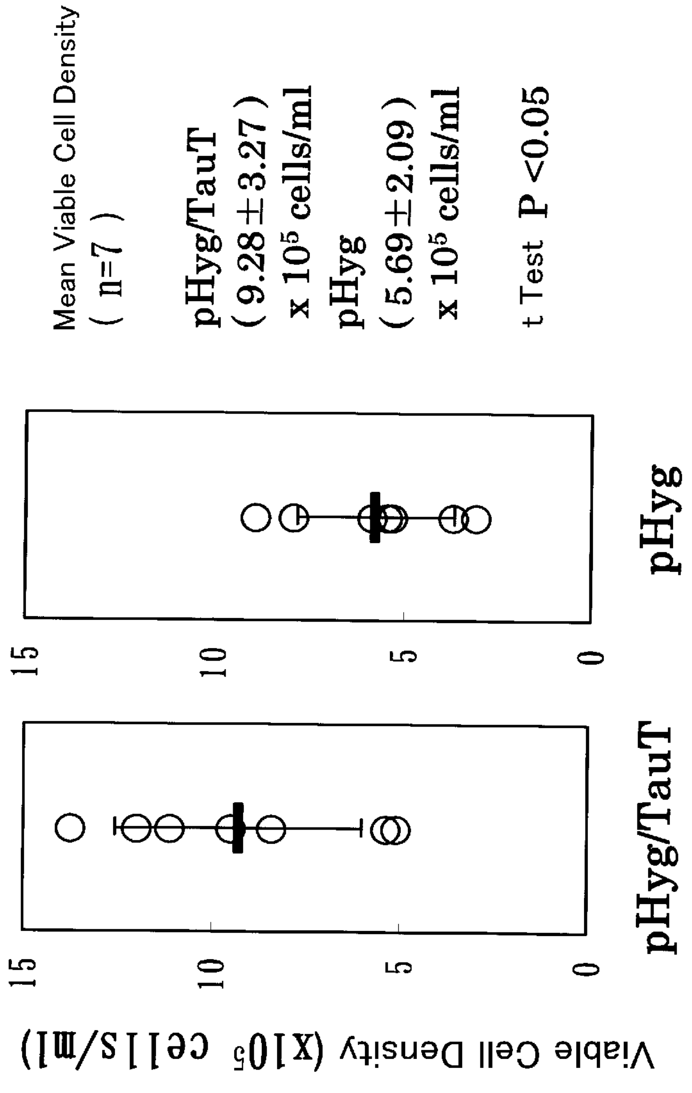
FIG. 19 shows viable cell density plots on day 7 of 50 ml shaker flask batch culture. The viable cell density in pHyg/TauT-transferred cell was superior to that in pHyg-transferred cell.
Figure 20:
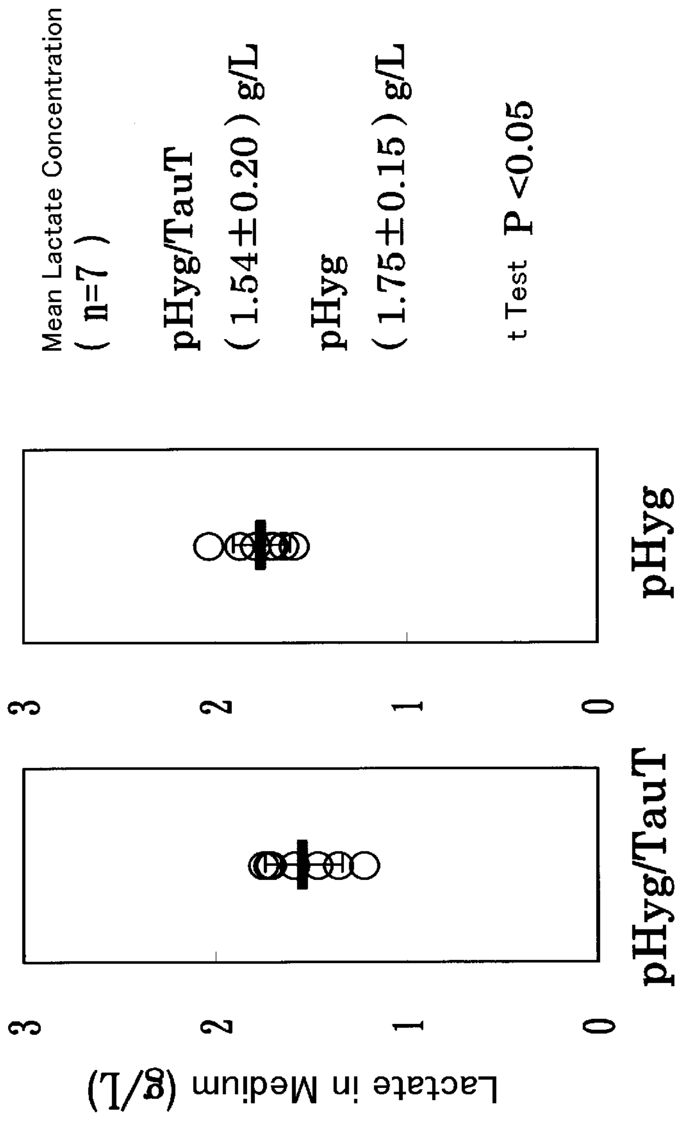
FIG. 20 shows lactate yield plots on day 7 of 50 ml shaker flask batch culture. pHyg/TauT-transferred cell produced less lactate, and was superior to pHyg-transferred cell.
Figure 21:
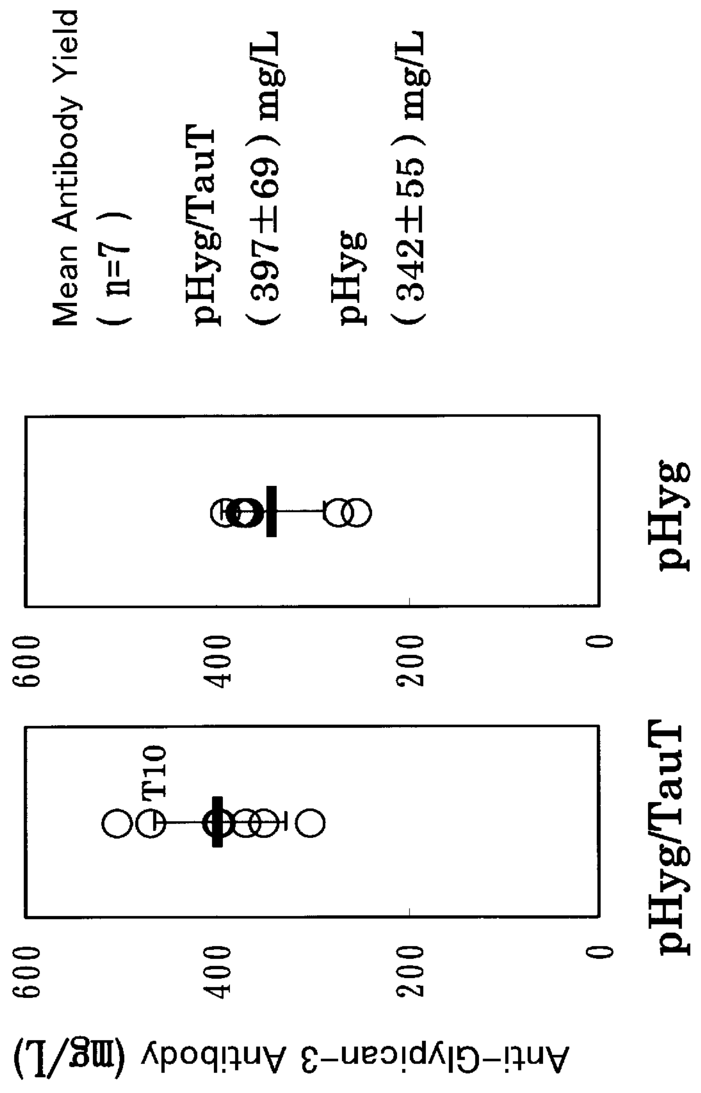
FIG. 21 shows anti-glypican-3 antibody yield plots on day 7 of 50 ml shaker flask batch culture. Four out of the 7 strains of pHyg/TauT-transferred cell showed antibody yields higher than the highest yield in pHyg-transferred cell.
Figure 22:
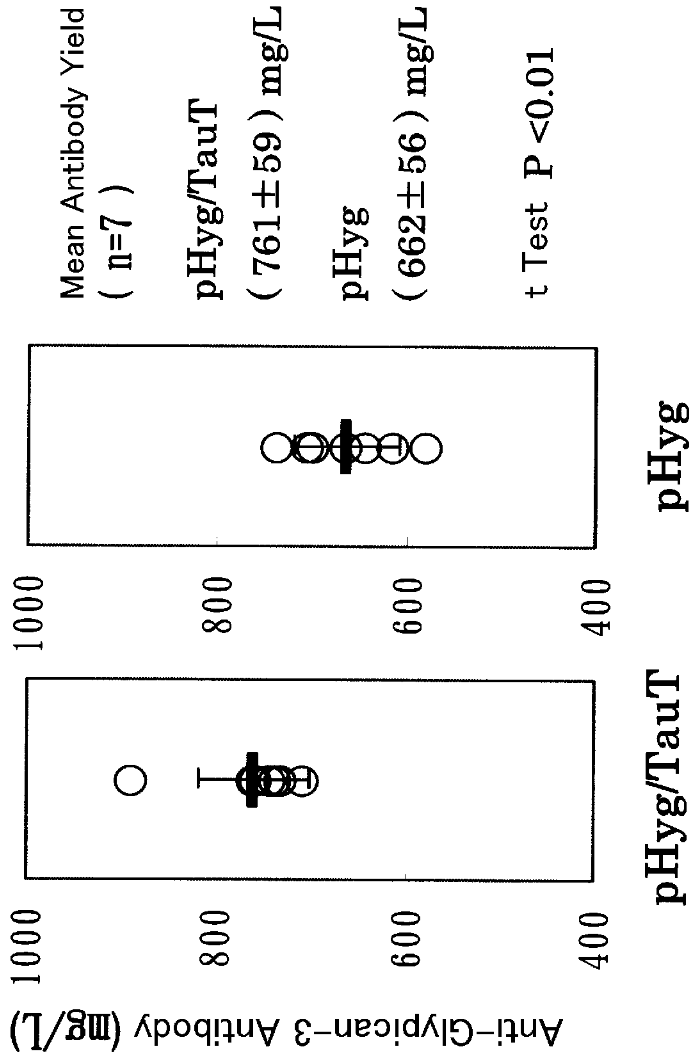
FIG. 22 shows anti-glypican-3 antibody yield plots on day 7 of 50 ml shaker flask fed-batch culture. The antibody yield in pHyg/TauT-transferred cell was superior to that in pHyg-transferred cell.
Figure 23:
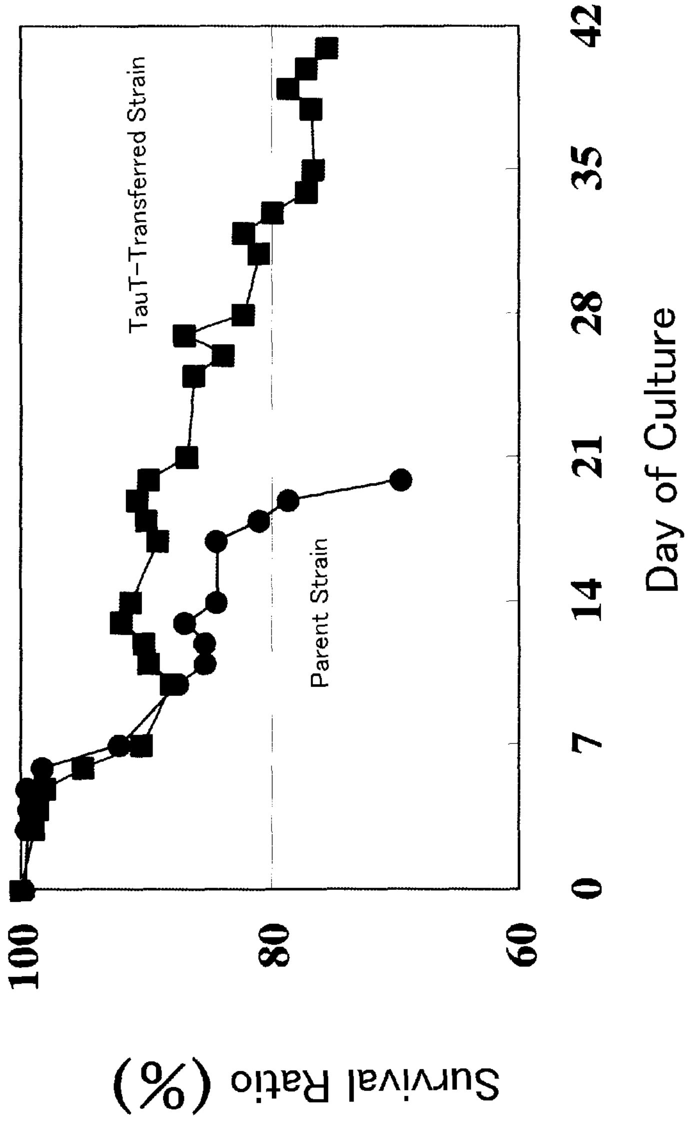
FIG. 23 is a graph showing the survival ratio of a pHyg/TauT-transferred cell T10 (which showed high growth ability) in 1 L jar fed-batch culture. The survival ratio of T10 was 80% or more even on day 32 of the culture.
Figure 24:
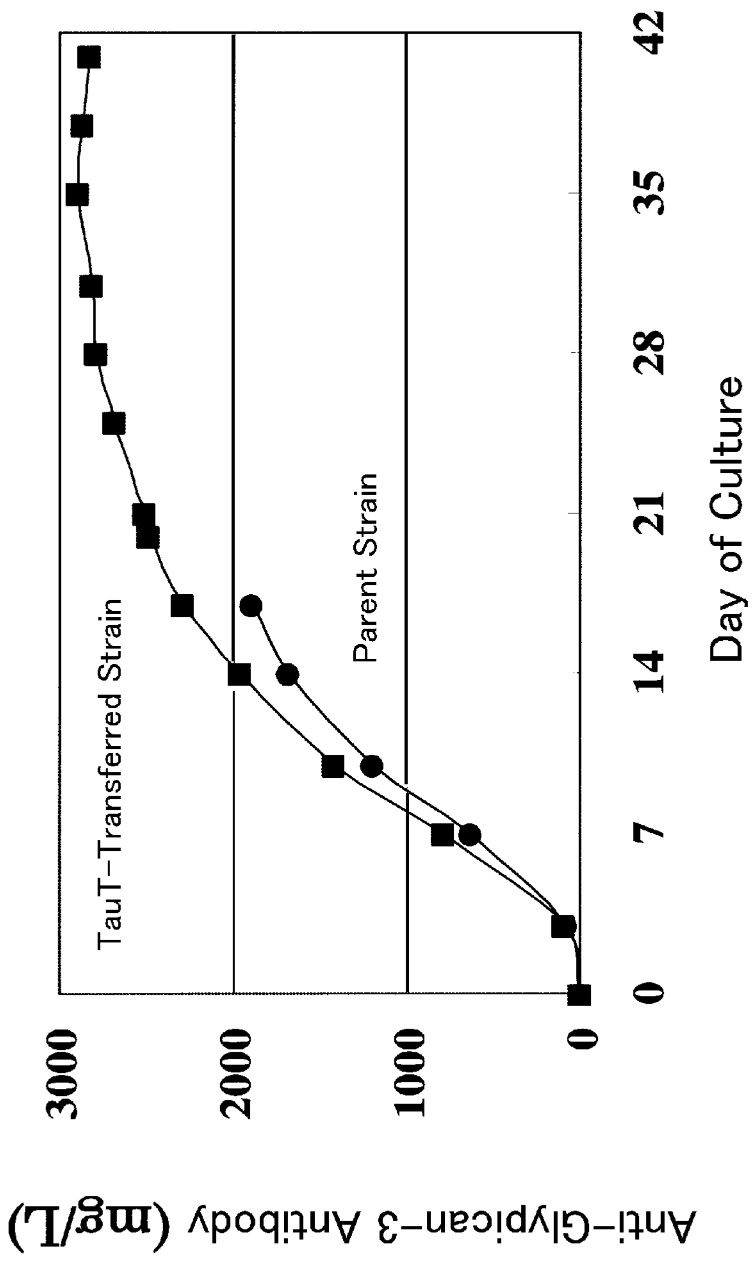
FIG. 24 is a graph showing the antibody yield of a pHyg/TauT-transferred cell T10 (which showed high growth ability during the expansion process in static culture) in 1 L jar fed-batch culture. The anti-glypican-3 antibody yield of T10 was 2.9 g/L on day 35 of the culture.
Figure 25:
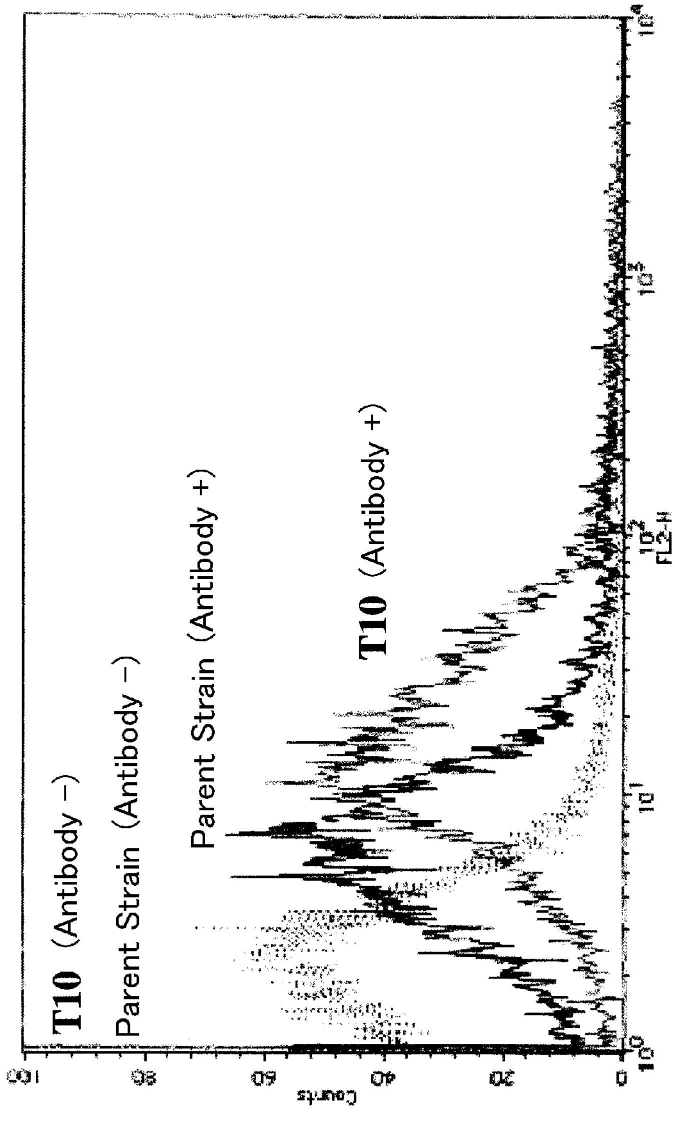
FIG. 25 shows the results of flow cytometric analysis indicating that TauT-transferred T10 cell is expressing TauT molecules on its cell membrane.

Increase in Viable Cell Density, Inhibition of Lactate Production and Increase in Antibody Yield, as Caused by Transfer of Hamster Taurine Transporter CMV promoter expression plasmid pHyg/TauT (FIG. 18) was constructed by adding Kozak sequence to the hamster TauT (hereinafter, TauT) gene obtained by cloning in Reference Example 1. Control plasmid pHyg without pHyg/TauT or TauT gene was introduced by electroporation into the parent strain anti-glypican-3 antibody producing CHO cell (see WO 2006/006693). After selection of expression plasmid-transferred cells in the presence of hygromycin (400 μg/ml), all of the stably growing cell strains were expanded (pHyg/TauT: 8 strains; pHyg: 7 strains). TauT mRNA was prepared. Subsequently, 7 strains were confirmed to express TauT more strongly than the parent strain by the TaqMan method; they were selected as pHyg/TauT transferred cells. The mean mRNA expression level of these transferred cells (7 strains) was about 40 times larger than the control (7 strains). Cells of the total 14 strains were subjected to batch culture and fed-batch culture in 50 ml shaker flasks with an initial cell density of $2\times10^5$ cells/ml. On day 7 of culture (late-stage), viable cell densities, lactate yields and anti-glypican-3 antibody yields in those strains were compared. In batch culture, growth inhibitory substances such as lactate accumulate in culture broth as cells grow and their growth is inhibited. However, the viable cell densities (FIG. 19) and lactate yields (FIG. 20) in pHyg/TauT transferred cells were superior to those in pHyg transferred cells (t test; $p<0.05$). With respect to anti-glypican-3 antibody yield, 4 out of the 7 strains of pHyg/TauT-transferred cell showed antibody yields higher than the highest yield in pHyg-transferred cell (FIG. 21). Further, since superiority of pHyg/TauT transferred cells in anti-glypican-3 antibody yield became more evident (t test; $P<0.01$; FIG. 22) in fed-batch culture, pHyg/TauT transferred T10 strain (which showed the highest growth ability among the above 4 strains) and the parent strain were subjected to fed-batch culture in 1 L jar. As a result, the viable ratio of T10 was maintained at 80% or more even on day 32 of culture (FIG. 23), with inhibited lactate production. Consequently, its anti-glypican-3 antibody yield achieved 2.9 g/L on day 35 of culture (FIG. 24). It was confirmed by flow cytometric analysis that TauT-transferred T10 cell was expressing TauT molecules on the cell membrane (FIG. 25). These results suggest that by artificially expressing hamster Taut, it is possible to raise the potential of antibody-producing cells and create strains capable of enhanced antibody production.

The present invention is applicable to any antibody-producing cell.

The fact that cells capable of producing antibodies in high yield were also obtained in a batch culture suggests that strong expression of TauT induced nonspecific integration of not only taurine but also β-alanine and many other amino acids. Organic osmolytes except taurine that have a cellular osmoregulatory function include β-alanine, alanine, glycine, proline, glutamic acid, glutamine, and aspartic acid, and the foregoing results predict that cells capable of high-yield antibody production can also be obtained by causing artificial expression of transporters for those organic osmolytes.

All publications, patent and patent applications cited herein are incorporated herein by reference in their entirety.

INDUSTRIAL APPLICABILITY

The present invention is applicable to production of polypeptides.

SEQUENCE LISTING FREE TEXT

<SEQ ID NO: 1>

SEQ ID NO: 1 shows the nucleotide sequence of a gene encoding hamster cysteine sulfinic acid decarboxylase.

<SEQ ID NO: 2>

SEQ ID NO: 2 shows the amino acid sequence of hamster cysteine sulfinic acid decarboxylase.

<SEQ ID NO: 3>

SEQ ID NO: 3 shows the nucleotide sequence of a gene encoding rat cysteine sulfinic acid decarboxylase.

<SEQ ID NO: 4>

SEQ ID NO: 4 shows the amino acid sequence of rat cysteine sulfinic acid decarboxylase.

<SEQ ID NO: 5>

SEQ ID NO: 5 shows the nucleotide sequence of a gene encoding mouse cysteine sulfinic acid decarboxylase.

<SEQ ID NO: 6>

SEQ ID NO: 6 shows the amino acid sequence of mouse cysteine sulfinic acid decarboxylase.

<SEQ ID NO: 7>

SEQ ID NO: 7 shows the nucleotide sequence of a gene encoding human cysteine sulfinic acid decarboxylase.

<SEQ ID NO: 8>

SEQ ID NO: 8 shows the amino acid sequence of human cysteine sulfinic acid decarboxylase.

<SEQ ID NO: 9>

SEQ ID NO: 9 shows the nucleotide sequence of a gene encoding hamster cysteine dioxygenase.

<SEQ ID NO: 10>

SEQ ID NO: 10 shows the amino acid sequence of hamster cysteine dioxygenase.

<SEQ ID NO: 11>

SEQ ID NO: 11 shows the nucleotide sequence of a gene encoding rat cysteine dioxygenase.

<SEQ ID NO: 12>

SEQ ID NO: 12 shows the amino acid sequence of rat cysteine dioxygenase.

<SEQ ID NO: 13>

SEQ ID NO: 13 shows the nucleotide sequence of a gene encoding mouse cysteine dioxygenase.

<SEQ ID NO: 14>

SEQ ID NO: 14 shows the amino acid sequence of mouse cysteine dioxygenase.

<SEQ ID NO: 15>

SEQ ID NO: 15 shows the nucleotide sequence of a gene encoding human cysteine dioxygenase.

<SEQ ID NO: 16>

SEQ ID NO: 16 shows the amino acid sequence of human cysteine dioxygenase.

<SEQ ID NO: 17>

SEQ ID NO: 17 shows the nucleotide sequence of a gene encoding bovine cysteine dioxygenase.

<SEQ ID NO: 18>

SEQ ID NO: 18 shows the amino acid sequence of bovine cysteine dioxygenase.

<SEQ ID NO: 19>

SEQ ID NO: 19 shows the nucleotide sequence of a gene encoding hamster taurine transporter.

<SEQ ID NO: 20>

SEQ ID NO: 20 shows the amino acid sequence of hamster taurine transporter.

<SEQ ID NO: 21>

SEQ ID NO: 21 shows the nucleotide sequence of a gene encoding rat taurine transporter.

<SEQ ID NO: 22>

SEQ ID NO:22 shows the amino acid sequence of rat taurine transporter.

<SEQ ID NO: 23>

SEQ ID NO: 23 shows the nucleotide sequence of a gene encoding mouse taurine transporter.

<SEQ ID NO: 24>

SEQ ID NO: 24 shows the amino acid sequence of mouse taurine transporter.

<SEQ ID NO: 25>

SEQ ID NO: 25 shows the nucleotide sequence of a gene encoding human taurine transporter.

<SEQ ID NO: 26>

SEQ ID NO: 26 shows the amino acid sequence of human taurine transporter.

The invention claimed is:

1. A method for producing a desired antibody, comprising culturing a cell capable of high-yield production of β-alanine to produce the desired antibody;

wherein the cell has been transformed by DNA encoding the desired antibody, wherein the cell has been transformed by DNA encoding cysteine sulfinic acid decarboxylase or a mutant thereof, wherein the mutant has the same enzyme activity as cysteine sulfinic acid decarboxylase, and wherein the DNA encoding the cysteine sulfinic acid decarboxylase is selected from the group consisting of:

(a) a DNA encoding a polypeptide consisting of the amino acid sequence as shown in SEQ ID NO: 8;

(b) a DNA encoding a polypeptide consisting of an amino acid sequence derived from the amino acid sequence as shown in SEQ ID NO: 8 by substitution, deletion and/or addition of 1-10 amino acid residues, wherein the polypeptide has cysteine sulfinic acid decarboxylase activity;

(c) a DNA encoding a polypeptide having 98% or more amino acid sequence homology with the amino acid sequence as shown in SEQ ID NO: 2, wherein the polypeptide has cysteine sulfinic acid decarboxylase activity;

(d) a DNA consisting of the nucleotide sequence as shown in SEQ ID NO: 7; and (e) a DNA that hybridizes to a DNA complementary to a DNA consisting of the nucleotide sequence as shown in SEQ ID NO: 7 under high stringent conditions of 65° C., 2×SSC and 0.1% SDS, wherein the DNA encodes a polypeptide having cysteine sulfinic acid decarboxylase activity.

2. The method according to claim 1, wherein the cell comprises a ratio of (i) intracellular concentration of β-alanine on the 6th or subsequent days after initiating culture to (ii) intracellular concentration of β-alanine at initiation of the culture of 2 or greater.

3. The method according to claim 1, wherein the cell is capable of increasing the β-alanine concentration in the culture medium on 6th or subsequent days after initiating the culture by 50μM or more.

4. A method for producing a desired antibody, comprising culturing a cell that strongly expresses cysteine sulfinic acid decarboxylase to produce the desired antibody;

wherein the cell has been transformed by DNA encoding the desired antibody, wherein the cell has been transformed by DNA encoding cysteine sulfinic acid, decarboxylase, and wherein the DNA encoding the cysteine sulfinic acid decarboxylase is selected from the group consisting of:

(a) a DNA encoding a polypeptide consisting of the amino acid sequence as shown in SEQ ID NO: 8;

(b) a DNA encoding a polypeptide consisting of an amino acid sequence derived from the amino acid sequence as shown in SEQ ID NO: 8 by substitution, deletion and/or addition of 1-10 amino acid residues, wherein the polypeptide has cysteine sulfinic acid decarboxylase activity;

(c) a DNA encoding a polypeptide having 98% or more amino acid sequence homology with the amino acid sequence as shown in SEQ ID NO: 2, wherein the polypeptide has cysteine sulfinic acid decarboxylase activity;

(d) a DNA consisting of the nucleotide sequence as shown in SEQ ID NO: 7; and (e) a DNA that hybridizes to a DNA complementary to a DNA consisting of the nucleotide sequence as shown in SEQ ID NO: 7 under high stringent conditions of 65° C., 2×SSC and 0.1% SDS, wherein the DNA encodes a polypeptide having cysteine sulfinic acid decarboxylase activity.

5. The method according to claim 4, wherein the cell is a Chinese hamster ovary cell.

6. A recombinant vector comprising a DNA encoding cysteine sulfinic acid decarboxylase selected from the group consisting of:

(a) a DNA encoding a polypeptide consisting of the amino acid sequence as shown in SEQ ID NO: 8;

(b) a DNA encoding a polypeptide consisting of an amino acid sequence derived from the amino acid sequence as shown in SEQ ID NO: 8 by substitution, deletion and/or addition of 1-10 amino acid residues, wherein the polypeptide has cysteine sulfinic acid decarboxylase activity;

(c) a DNA encoding a polypeptide having 98% or more amino acid sequence homology with the amino acid sequence as shown in SEQ ID NO: 2, wherein the polypeptide has cysteine sulfinic acid decarboxylase activity;

(d) a DNA consisting of the nucleotide sequence as shown in SEQ ID NO: 7; and (e) a DNA that hybridizes to a DNA complementary to a DNA consisting of the nucleotide sequence as shown in SEQ ID NO: 7 under high stringent conditions of 65° C., 2×SSC and 0.1% SDS, wherein the DNA encodes a polypeptide having cysteine sulfinic acid decarboxylase activity.

7. A cell transfected with the DNA according to claim 6.

8. The cell according to claim 7, wherein the cell is further transfected with DNA encoding a desired antibody.

9. The cell according to claim 8, wherein the cell is further transfected with DNA encoding a taurine transporter.

10. A cell capable of high-yield production of β-alanine and transfected with DNA according to claim 6.

11. The cell according to claim 10, wherein the cell is further transfected with a DNA encoding a desired antibody.

12. The method of claim 11, wherein the DNA encoding the cysteine sulfinic acid decarboxylase encodes a polypeptide having 97% or more amino acid sequence homology to the amino acid sequence of SEQ ID NO: 8.

* * * * *

SEQUENCE LISTING

<160> NUMBER OF SEQ ID NOS: 26

<210> SEQ ID NO 1
<211> LENGTH: 1482
<212> TYPE: DNA
<213> ORGANISM: Cricetulus griseus

<400> SEQUENCE: 1

```
atggctgact caaaaccact caatgccctg gatggggacc ctgtggctgt ggagtcctta     60

ctccgggatg tgtttgggat tgttgtagat gaggccattc ggaaagggac cagtgcctcg    120

gagaaggttt gtgaatggaa ggagcctgaa gagctcaagc atctgctgga tttggagctg    180

cagagccagg gcgagtctca agagcagatt ctagagcgct gccgggctgt gattcactac    240

agtgtcaaga ctggtcaccc ccggttcttc aaccagctct tctcagggtt agacccccat    300

gctctggctg ggcgcatcat cacagaaagc ctcaacacca gccagtacac atatgagatt    360

gcccctgtgt ttgtcctcat ggaagaggag gtgctgaaga aactccgtgc cctggtgggc    420

tggaactctg gggatggggt cttctgtcct ggtggctcca tctcgaacat gtatgccatg    480

aacctggccc gctatcagcg ctacccagac tgcaagcaaa gaggcctccg ggccctgccg    540

cccttggctc tcttcacttc aaaggagtgt cactactcca tcagtaaggg agctgctttt    600

ctgggacttg gcactgacag tgtccgagtg gtcaaggctg atgagagagg gaaaatgatc    660

cctgaggatc tggagaggca gatcagtctg gctgaggcag agggctctgt gccatttctg    720

gtcagtacca cctctggtac caccgtgcta ggggcctttg accccctgga tgcaattgct    780

gatgtttgcc agcgtcacgg attatggtta cacgtggatg ccgcctgggg tgggagcgtc    840

ctgctgtccc ggacacacag gcatctcctg gatgggatcc agagggctga ctctgtggcc    900

tggaaccctc acaagcttct cggtgcaggg ctgcagtgct ctgctcttct tctccgggac    960

acctcgaacc tgctcaagcg ctgccatggg tcccaggcca gctacctgtt ccagcaggac   1020

aaattctatg acgtggctct tgacactgga gacaaggtgg tgcagtgtgg ccgccgtgtg   1080

gactgtctga agttgtggct catgtggaag gcacagggtg ggcaaggact ggagcggcgc   1140

atcgaccagg cctttgctct cacccggtac ctggtggagg agataaaaaa gcgggaagga   1200

tttgagttgg tcatggagcc tgagtttgtc aatgtgtgct tctggtttgt gcctcccagc   1260

ctgcggggga agaaagagag tccagattac agcaaaaggc tgtctcaggt ggcgcctgta   1320

ctcaaggagc gcatggtgaa gaagggctcc atgatgattg gctaccagcc ccatgggacc   1380

cgggccaact tcttccggat ggtggtggcc aaccccacac tgacccaggc tgatatagac   1440

ttccttctgg gcgagctgga gcgtctgggc caggacctgt ga                      1482
```

<210> SEQ ID NO 2
<211> LENGTH: 493
<212> TYPE: PRT
<213> ORGANISM: Cricetulus griseus

<400> SEQUENCE: 2

```
Met Ala Asp Ser Lys Pro Leu Asn Ala Leu Asp Gly Asp Pro Val Ala
1               5                   10                  15

Val Glu Ser Leu Leu Arg Asp Val Phe Gly Ile Val Val Asp Glu Ala
            20                  25                  30

Ile Arg Lys Gly Thr Ser Ala Ser Glu Lys Val Cys Glu Trp Lys Glu
        35                  40                  45

Pro Glu Glu Leu Lys His Leu Leu Asp Leu Glu Leu Gln Ser Gln Gly
    50                  55                  60
```

-continued

```
Glu Ser Gln Glu Gln Ile Leu Glu Arg Cys Arg Ala Val Ile His Tyr
65                  70                  75                  80

Ser Val Lys Thr Gly His Pro Arg Phe Phe Asn Gln Leu Phe Ser Gly
                85                  90                  95

Leu Asp Pro His Ala Leu Ala Gly Arg Ile Ile Thr Glu Ser Leu Asn
            100                 105                 110

Thr Ser Gln Tyr Thr Tyr Glu Ile Ala Pro Val Phe Val Leu Met Glu
        115                 120                 125

Glu Glu Val Leu Lys Lys Leu Arg Ala Leu Val Gly Trp Asn Ser Gly
    130                 135                 140

Asp Gly Val Phe Cys Pro Gly Gly Ser Ile Ser Asn Met Tyr Ala Met
145                 150                 155                 160

Asn Leu Ala Arg Tyr Gln Arg Tyr Pro Asp Cys Lys Gln Arg Gly Leu
                165                 170                 175

Arg Ala Leu Pro Pro Leu Ala Leu Phe Thr Ser Lys Glu Cys His Tyr
            180                 185                 190

Ser Ile Ser Lys Gly Ala Ala Phe Leu Gly Leu Gly Thr Asp Ser Val
        195                 200                 205

Arg Val Val Lys Ala Asp Glu Arg Gly Lys Met Ile Pro Glu Asp Leu
    210                 215                 220

Glu Arg Gln Ile Ser Leu Ala Glu Ala Glu Gly Ser Val Pro Phe Leu
225                 230                 235                 240

Val Ser Thr Thr Ser Gly Thr Thr Val Leu Gly Ala Phe Asp Pro Leu
                245                 250                 255

Asp Ala Ile Ala Asp Val Cys Gln Arg His Gly Leu Trp Leu His Val
            260                 265                 270

Asp Ala Ala Trp Gly Gly Ser Val Leu Leu Ser Arg Thr His Arg His
        275                 280                 285

Leu Leu Asp Gly Ile Gln Arg Ala Asp Ser Val Ala Trp Asn Pro His
    290                 295                 300

Lys Leu Leu Gly Ala Gly Leu Gln Cys Ser Ala Leu Leu Leu Arg Asp
305                 310                 315                 320

Thr Ser Asn Leu Leu Lys Arg Cys His Gly Ser Gln Ala Ser Tyr Leu
                325                 330                 335

Phe Gln Gln Asp Lys Phe Tyr Asp Val Ala Leu Asp Thr Gly Asp Lys
            340                 345                 350

Val Val Gln Cys Gly Arg Arg Val Asp Cys Leu Lys Leu Trp Leu Met
        355                 360                 365

Trp Lys Ala Gln Gly Gly Gln Gly Leu Glu Arg Arg Ile Asp Gln Ala
    370                 375                 380

Phe Ala Leu Thr Arg Tyr Leu Val Glu Glu Ile Lys Lys Arg Glu Gly
385                 390                 395                 400

Phe Glu Leu Val Met Glu Pro Glu Phe Val Asn Val Cys Phe Trp Phe
                405                 410                 415

Val Pro Pro Ser Leu Arg Gly Lys Lys Glu Ser Pro Asp Tyr Ser Lys
            420                 425                 430

Arg Leu Ser Gln Val Ala Pro Val Leu Lys Glu Arg Met Val Lys Lys
        435                 440                 445

Gly Ser Met Met Ile Gly Tyr Gln Pro His Gly Thr Arg Ala Asn Phe
    450                 455                 460

Phe Arg Met Val Val Ala Asn Pro Thr Leu Thr Gln Ala Asp Ile Asp
465                 470                 475                 480
```

-continued

Phe Leu Leu Gly Glu Leu Glu Arg Leu Gly Gln Asp Leu
485 490

<210> SEQ ID NO 3
<211> LENGTH: 1482
<212> TYPE: DNA
<213> ORGANISM: Rattus norvegicus

<400> SEQUENCE: 3
atggctgact caaaaccact cagaaccctg gatggggacc ctgtggctgt ggaggctttg 60
ctccgggacg tgtttgggat tgtcgtagat gaggccattc ggaaggggac caatgcctct 120
gagaaggtct gcgaatggaa ggagcctgaa gagctcaagc agctgctgga cttggagctg 180
cagagccagg gcgagtctag ggagcggatc ctggagcgct gccgggctgt gattcattac 240
agtgtcaaga ctggtcaccc ccggttcttc aaccagctct tctcaggatt agatccccat 300
gctctggccg ggcgcatcat tacggagagc ctcaatacca gccagtacac atatgagatt 360
gcccccgtgt ttgtgctcat ggaagaggag gtgctgaaga aactccgtgc ccttgtgggc 420
tggaacactg ggatggggt cttctgtcct ggtggttcca tctctaacat gtacgccata 480
aacctggccc gctttcagcg ctacccagac tgcaagcaga ggggcctccg ggccctgcca 540
cccttggccc tcttcacttc aaaggagtgc cactactcca tcaccaaggg agctgctttt 600
ctgggacttg gcaccgacag tgtccgagtg gtcaaggctg atgagagagg gaagatgatc 660
cctgaggatc tggagaggca gatcagtctg gcagaggctg agggctcggt gccatttctg 720
gtcagtgcca cctctggtac caccgtgcta ggggcctttg accccctgga tgcaattgcc 780
gatgtttgcc agcgtcacgg gctgtggtta cacgtggatg ccgcctgggg tgggagcgtc 840
ctgctgtccc ggacacacag gcatctcctg gatgggatcc agagggctga ctccgtggcc 900
tggaaccctc acaagcttct cgccgcgggg ctgcagtgct ctgctcttct tctccgggac 960
acctcgaacc tgctcaagcg ctgccacggg tcccaggcca gctacctctt ccagcaagac 1020
aagttctaca acgtggctct ggacaccgga gacaaggtgg tgcagtgtgg ccgccgcgtg 1080
gactgtctga agctgtggct catgtggaag gcgcagggtg ggcaagggct ggagtggcgc 1140
atcgaccagg cctttgctct cactcggtac ttggtggagg agataaaaaa gcgggaagga 1200
tttgagttgg tcatggagcc cgagttcgtc aacgtgtgct tctggtttgt gcctcccagc 1260 ctgcgggga agaaggagag cccagattac agccagaggc tgtctcaggt ggcccctgtg 1320
ctcaaggagc gcatggtgaa gaagggaacc atgatgatcg gctaccagcc ccatgggacc 1380
cgggccaact tcttccgaat ggtggtggcc aaccccatac tggtccaggc cgatatagac 1440
ttccttctgg gcgagctgga gcgtctgggc caggacctgt ga 1482

<210> SEQ ID NO 4
<211> LENGTH: 493
<212> TYPE: PRT
<213> ORGANISM: Rattus norvegicus

<400> SEQUENCE: 4

Met Ala Asp Ser Lys Pro Leu Arg Thr Leu Asp Gly Asp Pro Val Ala
1 5 10 15

Val Glu Ala Leu Leu Arg Asp Val Phe Gly Ile Val Val Asp Glu Ala
20 25 30

Ile Arg Lys Gly Thr Asn Ala Ser Glu Lys Val Cys Glu Trp Lys Glu
35 40 45

Pro Glu Glu Leu Lys Gln Leu Leu Asp Leu Glu Leu Gln Ser Gln Gly

```
    50                  55                  60

Glu Ser Arg Glu Arg Ile Leu Glu Arg Cys Arg Ala Val Ile His Tyr
65                  70                  75                  80

Ser Val Lys Thr Gly His Pro Arg Phe Phe Asn Gln Leu Phe Ser Gly
                85                  90                  95

Leu Asp Pro His Ala Leu Ala Gly Arg Ile Ile Thr Glu Ser Leu Asn
            100                 105                 110

Thr Ser Gln Tyr Thr Tyr Glu Ile Ala Pro Val Phe Val Leu Met Glu
        115                 120                 125

Glu Glu Val Leu Lys Lys Leu Arg Ala Leu Val Gly Trp Asn Thr Gly
    130                 135                 140

Asp Gly Val Phe Cys Pro Gly Gly Ser Ile Ser Asn Met Tyr Ala Ile
145                 150                 155                 160

Asn Leu Ala Arg Phe Gln Arg Tyr Pro Asp Cys Lys Gln Arg Gly Leu
                165                 170                 175

Arg Ala Leu Pro Pro Leu Ala Leu Phe Thr Ser Lys Glu Cys His Tyr
            180                 185                 190

Ser Ile Thr Lys Gly Ala Ala Phe Leu Gly Leu Gly Thr Asp Ser Val
        195                 200                 205

Arg Val Val Lys Ala Asp Glu Arg Gly Lys Met Ile Pro Glu Asp Leu
    210                 215                 220

Glu Arg Gln Ile Ser Leu Ala Glu Ala Glu Gly Ser Val Pro Phe Leu
225                 230                 235                 240

Val Ser Ala Thr Ser Gly Thr Thr Val Leu Gly Ala Phe Asp Pro Leu
                245                 250                 255

Asp Ala Ile Ala Asp Val Cys Gln Arg His Gly Leu Trp Leu His Val
            260                 265                 270

Asp Ala Ala Trp Gly Gly Ser Val Leu Leu Ser Arg Thr His Arg His
        275                 280                 285

Leu Leu Asp Gly Ile Gln Arg Ala Asp Ser Val Ala Trp Asn Pro His
    290                 295                 300

Lys Leu Leu Ala Ala Gly Leu Gln Cys Ser Ala Leu Leu Leu Arg Asp
305                 310                 315                 320

Thr Ser Asn Leu Leu Lys Arg Cys His Gly Ser Gln Ala Ser Tyr Leu
                325                 330                 335

Phe Gln Gln Asp Lys Phe Tyr Asn Val Ala Leu Asp Thr Gly Asp Lys
            340                 345                 350

Val Val Gln Cys Gly Arg Arg Val Asp Cys Leu Lys Leu Trp Leu Met
        355                 360                 365

Trp Lys Ala Gln Gly Gly Gln Gly Leu Glu Trp Arg Ile Asp Gln Ala
    370                 375                 380

Phe Ala Leu Thr Arg Tyr Leu Val Glu Glu Ile Lys Lys Arg Glu Gly
385                 390                 395                 400

Phe Glu Leu Val Met Glu Pro Glu Phe Val Asn Val Cys Phe Trp Phe
                405                 410                 415

Val Pro Pro Ser Leu Arg Gly Lys Lys Glu Ser Pro Asp Tyr Ser Gln
            420                 425                 430

Arg Leu Ser Gln Val Ala Pro Val Leu Lys Glu Arg Met Val Lys Lys
        435                 440                 445

Gly Thr Met Met Ile Gly Tyr Gln Pro His Gly Thr Arg Ala Asn Phe
    450                 455                 460

Phe Arg Met Val Val Ala Asn Pro Ile Leu Val Gln Ala Asp Ile Asp
465                 470                 475                 480
```

Phe Leu Leu Gly Glu Leu Glu Arg Leu Gly Gln Asp Leu
485 490

<210> SEQ ID NO 5
<211> LENGTH: 1482
<212> TYPE: DNA
<213> ORGANISM: Mus musculus

<400> SEQUENCE: 5
atggctgact caaaaccact caggaccctg gatggggacc ccgtggctgt ggaggccttg 60
ctccaggacg tgtttgggat tgttgtagat gaggccattc tgaaggggac cagtgcctct 120
gagaaggtct gcgaatggaa ggagcctgaa gaactcaagc agctgctgga cttggagctg 180
cagagccagg gcgagtcccg ggagcagatc ctggagcgct gccggactgt gattcactac 240
agtgtcaaga ctggtcaccc ccggttcttc aaccagctct tctcagggtt agatccccat 300
gctctggctg ggcgcatcat cacggagagc ctcaacacta gccagtacac atatgagatt 360
gcccccgtgt ttgtgctcat ggaagaggag gtgctgaaga aactccgtgc cctggtgggc 420
tggaactctg gggatggggt cttctgtcct ggtggctcca tctccaacat gtacgccatg 480
aacctggccc gctttcagcg ctacccagac tgcaagcaga ggggcctccg ggccctgccg 540
cccttggctc tcttcacttc aaaggagtgt cactactcca tcaccaaggg agctgctttt 600
ctgggacttg gcaccgacag tgtccgagtg gtcaaggctg atgagagagg gaggatgatc 660
cctgaggacc tggagaggca gatcattctg gcagaggctg agggctctgt gccatttctg 720
gtcagtgcca cctctggtac caccgtgcta ggggcctttg acccccctgga tgcaattgcc 780 gatgtttgcc agcgacacgg actgtggttc catgtggatg ctgcctgggg tgggagcgtc 840
ctgctgtctc ggacacacag gcatctcctg gatgggatcc agagggctga ctctgtggcc 900
tggaaccctc acaagcttct cgccgcaggg ctgcagtgct ccgctcttct tctccgggac 960
acctcgaacc tgctcaagcg ctgccatgga tcccaggcca gctacctctt ccagcaagac 1020
aagttctacg atgtggctct ggacaccgga gacaaagtgg tgcagtgtgg ccgccgcgtg 1080
gactgtctga agctatggct catgtggaag gcacagggtg ggcaggggtt ggagcggcgc 1140
atcgaccagg cctttgctct cacccggtac ttggtggagg agattaaaaa gcgggaagga 1200
tttgagttgg taatggagcc cgagttcgtc aacgtgtgct tctggtttgt gcctccaagc 1260 cttcgggggga agaaggagag tccagattac agccaaaggc tgtctcaggt ggcccctgtg 1320
ctcaaggagc gcatggtgaa gaaggggacc atgatgattg gctaccagcc ccatgggacc 1380
cgggccaact tcttccgaat ggtggtggcc aaccccatac tggcccaggc cgatatagat 1440
ttccttctgg gcgagctgga gctcctgggc caggacctgt ga 1482

<210> SEQ ID NO 6
<211> LENGTH: 493
<212> TYPE: PRT
<213> ORGANISM: Mus musculus

<400> SEQUENCE: 6

Met Ala Asp Ser Lys Pro Leu Arg Thr Leu Asp Gly Asp Pro Val Ala
1 5 10 15

Val Glu Ala Leu Leu Gln Asp Val Phe Gly Ile Val Val Asp Glu Ala
20 25 30

Ile Leu Lys Gly Thr Ser Ala Ser Glu Lys Val Cys Glu Trp Lys Glu
35 40 45

-continued

```
Pro Glu Glu Leu Lys Gln Leu Leu Asp Leu Glu Leu Gln Ser Gln Gly
    50                  55                  60

Glu Ser Arg Glu Gln Ile Leu Glu Arg Cys Arg Thr Val Ile His Tyr
65                  70                  75                  80

Ser Val Lys Thr Gly His Pro Arg Phe Phe Asn Gln Leu Phe Ser Gly
                85                  90                  95

Leu Asp Pro His Ala Leu Ala Gly Arg Ile Ile Thr Glu Ser Leu Asn
            100                 105                 110

Thr Ser Gln Tyr Thr Tyr Glu Ile Ala Pro Val Phe Val Leu Met Glu
        115                 120                 125

Glu Glu Val Leu Lys Lys Leu Arg Ala Leu Val Gly Trp Asn Ser Gly
    130                 135                 140

Asp Gly Val Phe Cys Pro Gly Gly Ser Ile Ser Asn Met Tyr Ala Met
145                 150                 155                 160

Asn Leu Ala Arg Phe Gln Arg Tyr Pro Asp Cys Lys Gln Arg Gly Leu
                165                 170                 175

Arg Ala Leu Pro Pro Leu Ala Leu Phe Thr Ser Lys Glu Cys His Tyr
            180                 185                 190

Ser Ile Thr Lys Gly Ala Ala Phe Leu Gly Leu Gly Thr Asp Ser Val
        195                 200                 205

Arg Val Val Lys Ala Asp Glu Arg Gly Arg Met Ile Pro Glu Asp Leu
    210                 215                 220

Glu Arg Gln Ile Ile Leu Ala Glu Ala Glu Gly Ser Val Pro Phe Leu
225                 230                 235                 240

Val Ser Ala Thr Ser Gly Thr Thr Val Leu Gly Ala Phe Asp Pro Leu
                245                 250                 255

Asp Ala Ile Ala Asp Val Cys Gln Arg His Gly Leu Trp Phe His Val
            260                 265                 270

Asp Ala Ala Trp Gly Gly Ser Val Leu Leu Ser Arg Thr His Arg His
        275                 280                 285

Leu Leu Asp Gly Ile Gln Arg Ala Asp Ser Val Ala Trp Asn Pro His
    290                 295                 300

Lys Leu Leu Ala Ala Gly Leu Gln Cys Ser Ala Leu Leu Leu Arg Asp
305                 310                 315                 320

Thr Ser Asn Leu Leu Lys Arg Cys His Gly Ser Gln Ala Ser Tyr Leu
                325                 330                 335

Phe Gln Gln Asp Lys Phe Tyr Asp Val Ala Leu Asp Thr Gly Asp Lys
            340                 345                 350

Val Val Gln Cys Gly Arg Arg Val Asp Cys Leu Lys Leu Trp Leu Met
        355                 360                 365

Trp Lys Ala Gln Gly Gly Gln Gly Leu Glu Arg Arg Ile Asp Gln Ala
    370                 375                 380

Phe Ala Leu Thr Arg Tyr Leu Val Glu Glu Ile Lys Lys Arg Glu Gly
385                 390                 395                 400

Phe Glu Leu Val Met Glu Pro Glu Phe Val Asn Val Cys Phe Trp Phe
                405                 410                 415

Val Pro Pro Ser Leu Arg Gly Lys Lys Glu Ser Pro Asp Tyr Ser Gln
            420                 425                 430

Arg Leu Ser Gln Val Ala Pro Val Leu Lys Glu Arg Met Val Lys Lys
        435                 440                 445

Gly Thr Met Met Ile Gly Tyr Gln Pro His Gly Thr Arg Ala Asn Phe
    450                 455                 460

Phe Arg Met Val Val Ala Asn Pro Ile Leu Ala Gln Ala Asp Ile Asp
```

-continued 465 470 475 480

Phe Leu Leu Gly Glu Leu Glu Leu Leu Gly Gln Asp Leu
485 490

<210> SEQ ID NO 7
<211> LENGTH: 1482
<212> TYPE: DNA
<213> ORGANISM: Homo sapiens

<400> SEQUENCE: 7
atggctgact cagaagcact cccctccctt gctggggacc cagtggctgt ggaagccttg 60
ctccgggccg tgtttggggt tgttgtggat gaggccattc agaaaggaac cagtgtctcc 120
cagaaggtct gtgagtggaa ggagcctgag gagctgaagc agctgctgga tttggagctg 180
cggagccagg gcgagtcaca gaagcagatc ctggagcggt gtcgggctgt gattcgctac 240
agtgtcaaga ctggtcaccc tcggttcttc aaccagctct tctctgggtt ggatccccat 300
gctctggccg ggcgcattat cactgagagc ctcaacacca gccagtacac atatgaaatc 360
gcccccgtgt ttgtgctcat ggaagaggag gtgctgagga aactgcgggc cctggtgggc 420
tggagctctg ggacggaat cttctgccct ggtggctcca tctccaacat gtatgctgta 480
aatctggccc gctatcagcg ctacccggat tgcaagcaga ggggcctccg cacactgccg 540
cccctggccc tattcacatc gaaggagtgt cactactcca tccagaaggg agctgcgttt 600
ctgggacttg gcaccgacag tgtccgagtg gtcaaggctg atgagagagg gaaaatggtc 660
cccgaggatc tggagaggca gattggtatg gccgaggctg agggtgctgt gccgttcctg 720
gtcagtgcca cctctggcac cactgtgcta ggggcctttg accccctgga ggcaattgct 780
gatgtgtgcc agcgtcatgg gctatggctg catgtggatg ctgcctgggg tgggagcgtc 840
ctgctgtcac agacacacag gcatctcctg gatgggatcc agagggctga ctctgtggcc 900
tggaatcccc acaagctcct cgcagcaggc ctgcaatgct ctgcacttct tctccaggat 960
acctcgaacc tgctcaagcg ctgccatggg tcccaggcca gctacctttt ccagcaggac 1020
aagttctacg atgtggctct ggacacggga gacaaggtgg tgcagtgtgg ccgccgtgtg 1080
gactgtctga agctgtggct catgtggaag gcacagggcg atcaagggct ggagcggcgc 1140
atcgaccagg cctttgtcct tgcccggtac ctggtggagg aaatgaagaa gcgggaaggg 1200
tttgagctag tcatggagcc tgagtttgtc aatgtgtgtt tctggttcgt accccccagc 1260
ctgcgaggga agcaggagag tccagattac cacgaaaggc tgtcaaaggt ggcccccgtg 1320
ctcaaggagc gcatggtgaa ggagggctcc atgatgattg gctaccagcc ccacgggacc 1380
cggggcaact tcttccgtgt ggttgtggcc aactctgcac tgacctgtgc tgatatggac 1440
ttcctcctca acgagctgga gcggctaggc caggacctgt ga 1482

<210> SEQ ID NO 8
<211> LENGTH: 493
<212> TYPE: PRT
<213> ORGANISM: Homo sapiens

<400> SEQUENCE: 8

Met Ala Asp Ser Glu Ala Leu Pro Ser Leu Ala Gly Asp Pro Val Ala
1 5 10 15

Val Glu Ala Leu Leu Arg Ala Val Phe Gly Val Val Val Asp Glu Ala
20 25 30

Ile Gln Lys Gly Thr Ser Val Ser Gln Lys Val Cys Glu Trp Lys Glu
35 40 45

-continued

```
Pro Glu Glu Leu Lys Gln Leu Leu Asp Leu Glu Leu Arg Ser Gln Gly
    50                  55                  60

Glu Ser Gln Lys Gln Ile Leu Glu Arg Cys Arg Ala Val Ile Arg Tyr
65                  70                  75                  80

Ser Val Lys Thr Gly His Pro Arg Phe Phe Asn Gln Leu Phe Ser Gly
                85                  90                  95

Leu Asp Pro His Ala Leu Ala Gly Arg Ile Ile Thr Glu Ser Leu Asn
            100                 105                 110

Thr Ser Gln Tyr Thr Tyr Glu Ile Ala Pro Val Phe Val Leu Met Glu
        115                 120                 125

Glu Glu Val Leu Arg Lys Leu Arg Ala Leu Val Gly Trp Ser Ser Gly
    130                 135                 140

Asp Gly Ile Phe Cys Pro Gly Gly Ser Ile Ser Asn Met Tyr Ala Val
145                 150                 155                 160

Asn Leu Ala Arg Tyr Gln Arg Tyr Pro Asp Cys Lys Gln Arg Gly Leu
                165                 170                 175

Arg Thr Leu Pro Pro Leu Ala Leu Phe Thr Ser Lys Glu Cys His Tyr
            180                 185                 190

Ser Ile Gln Lys Gly Ala Ala Phe Leu Gly Leu Gly Thr Asp Ser Val
        195                 200                 205

Arg Val Val Lys Ala Asp Glu Arg Gly Lys Met Val Pro Glu Asp Leu
    210                 215                 220

Glu Arg Gln Ile Gly Met Ala Glu Ala Glu Gly Ala Val Pro Phe Leu
225                 230                 235                 240

Val Ser Ala Thr Ser Gly Thr Thr Val Leu Gly Ala Phe Asp Pro Leu
                245                 250                 255

Glu Ala Ile Ala Asp Val Cys Gln Arg His Gly Leu Trp Leu His Val
            260                 265                 270

Asp Ala Ala Trp Gly Gly Ser Val Leu Leu Ser Gln Thr His Arg His
        275                 280                 285

Leu Leu Asp Gly Ile Gln Arg Ala Asp Ser Val Ala Trp Asn Pro His
    290                 295                 300

Lys Leu Leu Ala Ala Gly Leu Gln Cys Ser Ala Leu Leu Leu Gln Asp
305                 310                 315                 320

Thr Ser Asn Leu Leu Lys Arg Cys His Gly Ser Gln Ala Ser Tyr Leu
                325                 330                 335

Phe Gln Gln Asp Lys Phe Tyr Asp Val Ala Leu Asp Thr Gly Asp Lys
            340                 345                 350

Val Val Gln Cys Gly Arg Arg Val Asp Cys Leu Lys Leu Trp Leu Met
        355                 360                 365

Trp Lys Ala Gln Gly Asp Gln Gly Leu Glu Arg Arg Ile Asp Gln Ala
    370                 375                 380

Phe Val Leu Ala Arg Tyr Leu Val Glu Glu Met Lys Lys Arg Glu Gly
385                 390                 395                 400

Phe Glu Leu Val Met Glu Pro Glu Phe Val Asn Val Cys Phe Trp Phe
                405                 410                 415

Val Pro Pro Ser Leu Arg Gly Lys Gln Glu Ser Pro Asp Tyr His Glu
            420                 425                 430

Arg Leu Ser Lys Val Ala Pro Val Leu Lys Glu Arg Met Val Lys Glu
        435                 440                 445

Gly Ser Met Met Ile Gly Tyr Gln Pro His Gly Thr Arg Gly Asn Phe
    450                 455                 460
```

-continued

```
Phe Arg Val Val Val Ala Asn Ser Ala Leu Thr Cys Ala Asp Met Asp
465                 470                 475                 480

Phe Leu Leu Asn Glu Leu Glu Arg Leu Gly Gln Asp Leu
                485                 490


<210> SEQ ID NO 9
<211> LENGTH: 603
<212> TYPE: DNA
<213> ORGANISM: Cricetulus griseus

<400> SEQUENCE: 9

atggaacgga ccgagctgct gaagccgcgg accctggccg acctcatccg catcttgcat      60

gagctcttcg cgggcgacga ggtcaacgta gaggaggtgc aggctgtact ggaagcctac     120

gagagcaatc cagccgagtg ggctttgtac gccaaattcg accagtacag gtatactcga     180

aatcttgtgg atcaaggaaa tgggaagttt aatctgatga ttctgtgctg gggtgaagga     240

catggcagca gtattcacga tcacacggac tcccactgct tttgaagat gctgcaagga      300

aacctaaagg agacattgtt tgcctggcct gacaaaaaat caaatgagat gatcaagaag     360

tcagaaagga ccttaaggga aaaccagtgt gcctacatta atgattccat tgggttacat     420

cgagtagaga atgtcagcca cacggagcct gctgtgagcc ttcacttgta cagtccacct     480

ttcgatacat gccatgcctt tgatcaaaga acgggacaca aaaacaaagt caccatgaca     540

ttccacagca aatttggaat caggactcca tttccaactt caggttcact ggagaacaac     600

taa                                                                   603


<210> SEQ ID NO 10
<211> LENGTH: 200
<212> TYPE: PRT
<213> ORGANISM: Cricetulus griseus

<400> SEQUENCE: 10

Met Glu Arg Thr Glu Leu Leu Lys Pro Arg Thr Leu Ala Asp Leu Ile
1               5                   10                  15

Arg Ile Leu His Glu Leu Phe Ala Gly Asp Glu Val Asn Val Glu Glu
            20                  25                  30

Val Gln Ala Val Leu Glu Ala Tyr Glu Ser Asn Pro Ala Glu Trp Ala
        35                  40                  45

Leu Tyr Ala Lys Phe Asp Gln Tyr Arg Tyr Thr Arg Asn Leu Val Asp
    50                  55                  60

Gln Gly Asn Gly Lys Phe Asn Leu Met Ile Leu Cys Trp Gly Glu Gly
65                  70                  75                  80

His Gly Ser Ser Ile His Asp His Thr Asp Ser His Cys Phe Leu Lys
                85                  90                  95

Met Leu Gln Gly Asn Leu Lys Glu Thr Leu Phe Ala Trp Pro Asp Lys
            100                 105                 110

Lys Ser Asn Glu Met Ile Lys Lys Ser Glu Arg Thr Leu Arg Glu Asn
        115                 120                 125

Gln Cys Ala Tyr Ile Asn Asp Ser Ile Gly Leu His Arg Val Glu Asn
    130                 135                 140

Val Ser His Thr Glu Pro Ala Val Ser Leu His Leu Tyr Ser Pro Pro
145                 150                 155                 160

Phe Asp Thr Cys His Ala Phe Asp Gln Arg Thr Gly His Lys Asn Lys
                165                 170                 175

Val Thr Met Thr Phe His Ser Lys Phe Gly Ile Arg Thr Pro Phe Pro
            180                 185                 190
```

-continued

```
Thr Ser Gly Ser Leu Glu Asn Asn
        195                 200


<210> SEQ ID NO 11
<211> LENGTH: 603
<212> TYPE: DNA
<213> ORGANISM: Rattus norvegicus

<400> SEQUENCE: 11

atggaacgga ccgagctgct gaagccccgg accctggccg acctcatccg aatcttgcat      60

gagctcttcg ccggggacga agtcaatgtg gaggaggtgc aggctgtgct ggaagcctac     120

gagagcaatc ctgccgagtg ggctttgtat gccaaattcg atcaatacag gtatactcga     180

aaccttgtgg atcaaggaaa tgggaagttt aatctgatga ttctgtgctg gggtgaaggg     240

catggcagca gtattcacga tcactcggac tcccactgct tttgaagct gctgcaagga      300

aatctaaagg agacattgtt tgactggcct gacaagaaat ccaacgagat gatcaagaag     360

tctgaaagaa ctttgaggga aaatcagtgt gcctacatta atgattctat tggcttacat     420

cgagtagaga acgtcagcca cacagagcct gctgtgagcc ttcacttgta cagtccacct     480

ttcgatacat gccatgcctt tgaccaacga acagggcata aaaacaaagt caccatgaca     540

ttccacagca aatttggaat cagaactcca tttacaactt caggttcact ggagaacaac     600

taa                                                                   603


<210> SEQ ID NO 12
<211> LENGTH: 200
<212> TYPE: PRT
<213> ORGANISM: Rattus norvegicus

<400> SEQUENCE: 12

Met Glu Arg Thr Glu Leu Leu Lys Pro Arg Thr Leu Ala Asp Leu Ile
1               5                   10                  15

Arg Ile Leu His Glu Leu Phe Ala Gly Asp Glu Val Asn Val Glu Glu
            20                  25                  30

Val Gln Ala Val Leu Glu Ala Tyr Glu Ser Asn Pro Ala Glu Trp Ala
        35                  40                  45

Leu Tyr Ala Lys Phe Asp Gln Tyr Arg Tyr Thr Arg Asn Leu Val Asp
    50                  55                  60

Gln Gly Asn Gly Lys Phe Asn Leu Met Ile Leu Cys Trp Gly Glu Gly
65                  70                  75                  80

His Gly Ser Ser Ile His Asp His Ser Asp Ser His Cys Phe Leu Lys
                85                  90                  95

Leu Leu Gln Gly Asn Leu Lys Glu Thr Leu Phe Asp Trp Pro Asp Lys
            100                 105                 110

Lys Ser Asn Glu Met Ile Lys Lys Ser Glu Arg Thr Leu Arg Glu Asn
        115                 120                 125

Gln Cys Ala Tyr Ile Asn Asp Ser Ile Gly Leu His Arg Val Glu Asn
    130                 135                 140

Val Ser His Thr Glu Pro Ala Val Ser Leu His Leu Tyr Ser Pro Pro
145                 150                 155                 160

Phe Asp Thr Cys His Ala Phe Asp Gln Arg Thr Gly His Lys Asn Lys
                165                 170                 175

Val Thr Met Thr Phe His Ser Lys Phe Gly Ile Arg Thr Pro Phe Thr
            180                 185                 190

Thr Ser Gly Ser Leu Glu Asn Asn
```

```
        195                 200

<210> SEQ ID NO 13
<211> LENGTH: 603
<212> TYPE: DNA
<213> ORGANISM: Mus musculus

<400> SEQUENCE: 13

atggaacgga ccgagctgct gaagccccgg accctggcgg acctcatccg catcttacat     60

gagctcttcg cgggggacga agtcaacgtg gaggaggtgc aggctgtact ggaagcctac    120

gagagcaatc ccgccgagtg ggctttgtat gccaaattcg atcaatacag gtatactcga    180

aatcttgtgg atcaaggaaa tgggaagttt aatctgatga ttctgtgctg gggtgaaggg    240

cacggcagca gtattcatga tcacacggac tcccactgct ttctgaagct gctgcaagga    300

aatctaaagg agacattgtt tgactggcct gacaaaaaat ccaacgagat gatcaagaag    360

tctgaaagaa ccctgaggga aaaccagtgt gcctacatta atgattccat tggcttacac    420

cgagtagaga acgtcagcca cacagagcct gccgtgagcc tccacttgta cagtccaccc    480

ttcgatacat gccacgcttt tgaccagaga acagggcata aaaacaaagt caccatgaca    540

ttccacagca agtttggaat caggactcca tttacaactt cagggtcact ggagaacaac    600

tag                                                                  603

<210> SEQ ID NO 14
<211> LENGTH: 200
<212> TYPE: PRT
<213> ORGANISM: Mus musculus

<400> SEQUENCE: 14

Met Glu Arg Thr Glu Leu Leu Lys Pro Arg Thr Leu Ala Asp Leu Ile
1               5                   10                  15

Arg Ile Leu His Glu Leu Phe Ala Gly Asp Glu Val Asn Val Glu Glu
            20                  25                  30

Val Gln Ala Val Leu Glu Ala Tyr Glu Ser Asn Pro Ala Glu Trp Ala
        35                  40                  45

Leu Tyr Ala Lys Phe Asp Gln Tyr Arg Tyr Thr Arg Asn Leu Val Asp
    50                  55                  60

Gln Gly Asn Gly Lys Phe Asn Leu Met Ile Leu Cys Trp Gly Glu Gly
65                  70                  75                  80

His Gly Ser Ser Ile His Asp His Thr Asp Ser His Cys Phe Leu Lys
                85                  90                  95

Leu Leu Gln Gly Asn Leu Lys Glu Thr Leu Phe Asp Trp Pro Asp Lys
            100                 105                 110

Lys Ser Asn Glu Met Ile Lys Lys Ser Glu Arg Thr Leu Arg Glu Asn
        115                 120                 125

Gln Cys Ala Tyr Ile Asn Asp Ser Ile Gly Leu His Arg Val Glu Asn
    130                 135                 140

Val Ser His Thr Glu Pro Ala Val Ser Leu His Leu Tyr Ser Pro Pro
145                 150                 155                 160

Phe Asp Thr Cys His Ala Phe Asp Gln Arg Thr Gly His Lys Asn Lys
                165                 170                 175

Val Thr Met Thr Phe His Ser Lys Phe Gly Ile Arg Thr Pro Phe Thr
            180                 185                 190

Thr Ser Gly Ser Leu Glu Asn Asn
        195                 200
```

<210> SEQ ID NO 15
<211> LENGTH: 603
<212> TYPE: DNA
<213> ORGANISM: Homo sapiens

<400> SEQUENCE: 15
atggaacaga ccgaagtgct gaagccacgg accctggctg atctgatccg catcctgcac 60
cagctctttg ccggcgatga ggtcaatgta gaggaggtgc aggccatcat ggaagcctac 120
gagagcgacc ccaccgagtg ggcaatgtac gccaagttcg accagtacag gtatacccga 180
aatcttgtgg atcaaggaaa tggaaaattt aatctgatga ttctctgttg ggggtgaagga 240 catggcagca gtattcatga tcataccaac tcccactgct ttctgaagat gctacaggga 300
aatctaaagg agacattatt tgcctggcct gacaaaaaat ccaatgagat ggtcaagaag 360
tctgaaagag tcttgaggga aaaccagtgt gcctacatca atgattccat tggcttacat 420
cgagtagaga acatcagcca tacggaacct gctgtgagcc ttcacttgta cagtccacct 480
tttgatacat gccatgcctt tgatcaaaga acaggacata aaaacaaagt cacaatgaca 540
ttccatagta aatttggaat cagaactcca aatgcaactt cgggctcgct ggagaacaac 600
taa 603

<210> SEQ ID NO 16
<211> LENGTH: 200
<212> TYPE: PRT
<213> ORGANISM: Homo sapiens

<400> SEQUENCE: 16

Met Glu Gln Thr Glu Val Leu Lys Pro Arg Thr Leu Ala Asp Leu Ile
1 5 10 15

Arg Ile Leu His Gln Leu Phe Ala Gly Asp Glu Val Asn Val Glu Glu
20 25 30

Val Gln Ala Ile Met Glu Ala Tyr Glu Ser Asp Pro Thr Glu Trp Ala
35 40 45

Met Tyr Ala Lys Phe Asp Gln Tyr Arg Tyr Thr Arg Asn Leu Val Asp
50 55 60

Gln Gly Asn Gly Lys Phe Asn Leu Met Ile Leu Cys Trp Gly Glu Gly
65 70 75 80

His Gly Ser Ser Ile His Asp His Thr Asn Ser His Cys Phe Leu Lys
85 90 95

Met Leu Gln Gly Asn Leu Lys Glu Thr Leu Phe Ala Trp Pro Asp Lys
100 105 110

Lys Ser Asn Glu Met Val Lys Lys Ser Glu Arg Val Leu Arg Glu Asn
115 120 125

Gln Cys Ala Tyr Ile Asn Asp Ser Ile Gly Leu His Arg Val Glu Asn
130 135 140

Ile Ser His Thr Glu Pro Ala Val Ser Leu His Leu Tyr Ser Pro Pro
145 150 155 160

Phe Asp Thr Cys His Ala Phe Asp Gln Arg Thr Gly His Lys Asn Lys
165 170 175

Val Thr Met Thr Phe His Ser Lys Phe Gly Ile Arg Thr Pro Asn Ala
180 185 190

Thr Ser Gly Ser Leu Glu Asn Asn
195 200

<210> SEQ ID NO 17

<211> LENGTH: 603
<212> TYPE: DNA
<213> ORGANISM: Bos taurus

<400> SEQUENCE: 17
atggagcgga ccgaggtgct aaagccccgc accctggccg atctgatccg cgtcctgcac 60
cagctcttcg ccggcgagga gatcaacgtg gaggaagtgc aggccgtcat ggaagcctat 120
gagagcaacc ccgccgagtg ggcagtgtac gccaagttcg accagtacag gtatactcga 180
aatcttgtgg atcaaggaaa tggaaagttt aatctcatga ttctatgctg gggtgaagga 240
catggcagca gtatccatga tcacaccgac tcccactgct ttctgaagat gctgcaggga 300
aatctaaagg agacattgtt tgcctggcct gacaagaaat ccaatgagat gatcaagaag 360
tctgaaagaa tcttgaggga aaaccagtgt gcctacatca atgattccat tggcttacat 420
cgagtagaga atattagcca tacagagcct gccgtgagcc ttcacttgta tagtccgcct 480
tttgacacat gccacgcctt tgatcaaaga acaggacata aaaacaaagt catcatgaca 540
ttccatagca aatttggaat caagactcca tttacaactt caggatccct ggagaacaac 600
taa 603

<210> SEQ ID NO 18
<211> LENGTH: 200
<212> TYPE: PRT
<213> ORGANISM: Bos taurus

<400> SEQUENCE: 18

Met Glu Arg Thr Glu Val Leu Lys Pro Arg Thr Leu Ala Asp Leu Ile
1 5 10 15

Arg Val Leu His Gln Leu Phe Ala Gly Glu Glu Ile Asn Val Glu Glu
20 25 30

Val Gln Ala Val Met Glu Ala Tyr Glu Ser Asn Pro Ala Glu Trp Ala
35 40 45

Val Tyr Ala Lys Phe Asp Gln Tyr Arg Tyr Thr Arg Asn Leu Val Asp
50 55 60

Gln Gly Asn Gly Lys Phe Asn Leu Met Ile Leu Cys Trp Gly Glu Gly
65 70 75 80

His Gly Ser Ser Ile His Asp His Thr Asp Ser His Cys Phe Leu Lys
85 90 95

Met Leu Gln Gly Asn Leu Lys Glu Thr Leu Phe Ala Trp Pro Asp Lys
100 105 110

Lys Ser Asn Glu Met Ile Lys Lys Ser Glu Arg Ile Leu Arg Glu Asn
115 120 125

Gln Cys Ala Tyr Ile Asn Asp Ser Ile Gly Leu His Arg Val Glu Asn
130 135 140

Ile Ser His Thr Glu Pro Ala Val Ser Leu His Leu Tyr Ser Pro Pro
145 150 155 160

Phe Asp Thr Cys His Ala Phe Asp Gln Arg Thr Gly His Lys Asn Lys
165 170 175

Val Ile Met Thr Phe His Ser Lys Phe Gly Ile Lys Thr Pro Phe Thr
180 185 190

Thr Ser Gly Ser Leu Glu Asn Asn
195 200

<210> SEQ ID NO 19
<211> LENGTH: 1869
<212> TYPE: DNA

-continued

<213> ORGANISM: Cricetulus griseus

<400> SEQUENCE: 19

```
atggccacca aggagaagct gcagtgtctg aaagacttcc acaaagacat cctgaagcct      60
tctccaggga agagcccagg cacacggcct gaggatgagg ctgaggggaa gccccctcag     120
agggagaagt ggtccagcaa gattgacttt gtgctgtctg tggccggagg cttcgtgggt     180
ttgggcaacg tttggcgttt cccgtacctc tgctacaaaa atggtggagg tgctttcctc     240
ataccgtatt ttattttcct gtttgggagt ggcctgcctg tgtttttcct ggaggtcata     300
ataggccagt acacctcaga agggggaatc acctgctggg agaagatctg ccccttgttc     360
tctggcattg gctacgcatc catcgtcatc gtgtccctcc tgaatgtgta ctacattgtc     420
atcctggcct gggccacata ctacctattt cactccttcc agacagagct tccctgggcc     480
cactgcaacc acagctggaa cacaccacat tgcatggagg acaccctgcg taggaatgag     540
agtctctggg tctcccttag cgcctccaac ttcacctcgc ctgtcatcga gttctgggag     600
cgcaatgtac tcagcctgtc ttccggaatc gacgaaccag gcgctctgaa atggaccctt     660
gcgctctgcc tcctcttagt ctggcttgtc tgtttttct  gcatatggaa gggtgttcga     720
tccacaggca aggttgtcta cttcaccgcc actttcccgt ttgccatgct tctggtgctg     780
ctggtccgtg gactgaccct gccgggtgct ggcgaaggca tcaaattcta cctgtaccct     840
gacatcagcc gccttgagga cccacaggtg tggatcgacg ccggaaccca gatattcttt     900
tcctatgcca tctgcctggg ggccatgacc tcactgggaa gctacaacaa gtacaagtat     960
aactcgtaca gggactgtat gctgctggga tgcctgaaca gtggtaccag ttttgtgtct    1020
ggcttcgcag tttttttccat cctgggcttc atggcacaag agcaaggggt ggacattgct   1080
gatgtggctg agtcaggtcc tggcttggcc ttcattgcct atccaaaagc tgtgactatg    1140
atgccgctgc ccaccttttg gtccattctg tttttatta  tgctcctctt gcttggactg    1200
gacagccagt ttgttgaagt cgaaggacag atcacatcct tggttgatct ttacccgtcc    1260
ttcctaagga agggttatcg tcgggaagtc ttcatcgcca tcctgtgtag catcagctac    1320
ctgctggggc tgtcgatggt gacggagggt ggcatgtatg tgtttcaact ctttgactac    1380
tatgcagcta gtggtgtatg ccttttgtgg gttgcattct ttgaatgttt tgttattgcc    1440
tggatatatg gtggtgataa cttatatgac ggtattgagg acatgattgg ctatcggcct    1500
gggccctgga tgaagtacag ctgggctgtc atcactccag ttctctgtgc tggatgtttc    1560
atcttctctc ttgtcaagta tgtacccctg acctacaaca aagtctacgt gtatcctgat    1620
tgggcaattg ggctgggctg gggcctggcc ctatcctcca tggtgtgtat ccccttggtc    1680
attgccatcc tcctctgccg gacggaggga ccgttccgcg tgagaatcca atacctgata    1740
acccccaggg agcccaaccg ctgggctgtg gagcgtgagg gggccacacc cttccactcc    1800
cgcacaagcc tcgtcatgaa cggcgcactc atgaaaccca gtcacgtcat tgtggagacc    1860
atgatgtga                                                            1869
```

<210> SEQ ID NO 20
<211> LENGTH: 622
<212> TYPE: PRT
<213> ORGANISM: Cricetulus griseus

<400> SEQUENCE: 20

```
Met Ala Thr Lys Glu Lys Leu Gln Cys Leu Lys Asp Phe His Lys Asp
1               5                   10                  15
```

-continued

```
Ile Leu Lys Pro Ser Pro Gly Lys Ser Pro Gly Thr Arg Pro Glu Asp
            20                  25                  30

Glu Ala Glu Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Val Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Ile
        115                 120                 125

Val Ile Val Ser Leu Leu Asn Val Tyr Tyr Ile Val Ile Leu Ala Trp
    130                 135                 140

Ala Thr Tyr Tyr Leu Phe His Ser Phe Gln Thr Glu Leu Pro Trp Ala
145                 150                 155                 160

His Cys Asn His Ser Trp Asn Thr Pro His Cys Met Glu Asp Thr Leu
                165                 170                 175

Arg Arg Asn Glu Ser Leu Trp Val Ser Leu Ser Ala Ser Asn Phe Thr
            180                 185                 190

Ser Pro Val Ile Glu Phe Trp Glu Arg Asn Val Leu Ser Leu Ser Ser
        195                 200                 205

Gly Ile Asp Glu Pro Gly Ala Leu Lys Trp Asp Leu Ala Leu Cys Leu
    210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Glu
            260                 265                 270

Gly Ile Lys Phe Tyr Leu Tyr Pro Asp Ile Ser Arg Leu Glu Asp Pro
        275                 280                 285

Gln Val Trp Ile Asp Ala Gly Thr Gln Ile Phe Phe Ser Tyr Ala Ile
    290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Val Phe Ser Ile Leu Gly Phe Met Ala
            340                 345                 350

Gln Glu Gln Gly Val Asp Ile Ala Asp Val Ala Glu Ser Gly Pro Gly
        355                 360                 365

Leu Ala Phe Ile Ala Tyr Pro Lys Ala Val Thr Met Met Pro Leu Pro
    370                 375                 380

Thr Phe Trp Ser Ile Leu Phe Phe Ile Met Leu Leu Leu Leu Gly Leu
385                 390                 395                 400

Asp Ser Gln Phe Val Glu Val Glu Gly Gln Ile Thr Ser Leu Val Asp
                405                 410                 415

Leu Tyr Pro Ser Phe Leu Arg Lys Gly Tyr Arg Arg Glu Val Phe Ile
            420                 425                 430

Ala Ile Leu Cys Ser Ile Ser Tyr Leu Leu Gly Leu Ser Met Val Thr
```

-continued

```
        435                 440                 445

Glu Gly Gly Met Tyr Val Phe Gln Leu Phe Asp Tyr Tyr Ala Ala Ser
    450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
            500                 505                 510

Pro Val Leu Cys Ala Gly Cys Phe Ile Phe Ser Leu Val Lys Tyr Val
        515                 520                 525

Pro Leu Thr Tyr Asn Lys Val Tyr Val Tyr Pro Asp Trp Ala Ile Gly
    530                 535                 540

Leu Gly Trp Gly Leu Ala Leu Ser Ser Met Val Cys Ile Pro Leu Val
545                 550                 555                 560

Ile Ala Ile Leu Leu Cys Arg Thr Glu Gly Pro Phe Arg Val Arg Ile
                565                 570                 575

Gln Tyr Leu Ile Thr Pro Arg Glu Pro Asn Arg Trp Ala Val Glu Arg
            580                 585                 590

Glu Gly Ala Thr Pro Phe His Ser Arg Thr Ser Leu Val Met Asn Gly
        595                 600                 605

Ala Leu Met Lys Pro Ser His Val Ile Val Glu Thr Met Met
    610                 615                 620


<210> SEQ ID NO 21
<211> LENGTH: 1866
<212> TYPE: DNA
<213> ORGANISM: Rattus norvegicus

<400> SEQUENCE: 21

atggccacca aggagaagct tcaatgtctg aaagacttcc acaaagacat cctgaagcct      60

tctccaggga agagcccagg cacgcggcct gaggatgagg ctgatgggaa gcccccctcag    120

agggagaagt ggtccagcaa gatcgacttt gtgctgtctg tggccggagg cttcgtgggt    180

ttgggcaatg tctggcgttt cccgtacctc tgctacaaaa atggtggagg tgcattcctc    240

ataccgtatt ttattttcct gtttgggagc ggcctgcctg tgtttttcct ggaggtcatc    300

ataggccagt acacctcaga agggggcatc acctgctggg agaagatctg ccccttgttc    360

tctggcattg gctacgcgtc catcgtcatc gtgtccctcc tgaatgtgta ctacatcgtc    420

atcctggcct gggccacata ctacctattc cagtctttcc agaaggatct tccctgggcc    480

cactgcaacc atagctggaa cacgccacag tgcatggagg acaccctgcg taggaacgag    540

agtcactggg tctcccttag cgccgccaac ttcacttcgc ctgtgatcga gttctgggag    600

cgcaacgtgc tcagcctgtc ctccggaatc gaccacccag gcagtctgaa atgggacctc    660

gcgctctgcc tcctcttagt ctggctcgtc tgttttttct gcatctggaa gggtgttcgg    720

tccacaggca aggttgtcta cttcactgct actttcccgt ttgccatgct tctggtgctg    780

ctggtccgtg gactgaccct gccaggtgct ggtgaaggca tcaaattcta cctgtaccct    840

aacatcagcc gccttgagga cccacaggtg tggatcgacg ctggaactca gatattcttt    900

tcctacgcta tctgcctggg ggccatgacc tcactgggaa gctataacaa gtacaagtat    960

aactcgtaca gggactgtat gctgctggga tgcctgaaca gtggtaccag ttttgtgtct   1020

ggcttcgcaa ttttttccat cctgggcttc atggcacaag agcaaggggt ggacattgct   1080
```

```
gatgtggctg agtcaggtcc tggcttggcc ttcattgcct acccaaaagc tgtgaccatg   1140

atgccgctgc ccaccttttg gtccattctg tttttatta tgctcctctt gcttggactg   1200

gacagccagt ttgttgaagt cgaaggacag atcacatcct tggttgatct ttacccgtcc   1260

ttcctaagga agggttatcg tcgggaaatc ttcattgcca tcgtgtgcag catcagctac   1320

ctgctggggc tgacgatggt gacggagggt ggcatgtatg tgtttcaact ctttgactac   1380

tatgcagcta gtggtgtatg ccttttgtgg gtcgcattct ttgaatgttt tgttattgcc   1440

tggatatatg gcggtgataa cttatatgac ggtattgagg acatgatcgg ctatcggcct   1500

ggaccctgga tgaagtacag ctgggctgtc atcactccag ctctctgtgt tggatgtttc   1560

atcttctctc tcgtcaagta tgtacccctg acctacaaca aagtctaccg gtaccctgat   1620

tgggcaatcg ggctgggctg gggcctggcc ctttcctcca tggtgtgtat ccccttggtc   1680

attgtcatcc tcctctgccg gacggaggga ccgctccgcg tgagaatcaa atacctgata   1740

acccccaggg agcccaaccg ctgggctgtg gagcgtgaag ggctacgcc ctttcactcc   1800

agagcaaccc tcatgaacgg tgcactcatg aaacccagtc acgtcattgt ggagaccatg   1860

atgtga                                                                1866


<210> SEQ ID NO 22
<211> LENGTH: 621
<212> TYPE: PRT
<213> ORGANISM: Rattus norvegicus

<400> SEQUENCE: 22

Met Ala Thr Lys Glu Lys Leu Gln Cys Leu Lys Asp Phe His Lys Asp
1               5                   10                  15

Ile Leu Lys Pro Ser Pro Gly Lys Ser Pro Gly Thr Arg Pro Glu Asp
            20                  25                  30

Glu Ala Asp Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Val Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Ile
        115                 120                 125

Val Ile Val Ser Leu Leu Asn Val Tyr Tyr Ile Val Ile Leu Ala Trp
    130                 135                 140

Ala Thr Tyr Tyr Leu Phe Gln Ser Phe Gln Lys Asp Leu Pro Trp Ala
145                 150                 155                 160

His Cys Asn His Ser Trp Asn Thr Pro Gln Cys Met Glu Asp Thr Leu
                165                 170                 175

Arg Arg Asn Glu Ser His Trp Val Ser Leu Ser Ala Ala Asn Phe Thr
            180                 185                 190

Ser Pro Val Ile Glu Phe Trp Glu Arg Asn Val Leu Ser Leu Ser Ser
        195                 200                 205

Gly Ile Asp His Pro Gly Ser Leu Lys Trp Asp Leu Ala Leu Cys Leu
    210                 215                 220

Leu Leu Val Trp Leu Val Cys Phe Phe Cys Ile Trp Lys Gly Val Arg
```

-continued

```
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Glu
            260                 265                 270

Gly Ile Lys Phe Tyr Leu Tyr Pro Asn Ile Ser Arg Leu Glu Asp Pro
        275                 280                 285

Gln Val Trp Ile Asp Ala Gly Thr Gln Ile Phe Phe Ser Tyr Ala Ile
    290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Ile Phe Ser Ile Leu Gly Phe Met Ala
            340                 345                 350

Gln Glu Gln Gly Val Asp Ile Ala Asp Val Ala Glu Ser Gly Pro Gly
        355                 360                 365

Leu Ala Phe Ile Ala Tyr Pro Lys Ala Val Thr Met Met Pro Leu Pro
    370                 375                 380

Thr Phe Trp Ser Ile Leu Phe Phe Ile Met Leu Leu Leu Leu Gly Leu
385                 390                 395                 400

Asp Ser Gln Phe Val Glu Val Glu Gly Gln Ile Thr Ser Leu Val Asp
                405                 410                 415

Leu Tyr Pro Ser Phe Leu Arg Lys Gly Tyr Arg Arg Glu Ile Phe Ile
            420                 425                 430

Ala Ile Val Cys Ser Ile Ser Tyr Leu Leu Gly Leu Thr Met Val Thr
        435                 440                 445

Glu Gly Gly Met Tyr Val Phe Gln Leu Phe Asp Tyr Tyr Ala Ala Ser
    450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
            500                 505                 510

Pro Ala Leu Cys Val Gly Cys Phe Ile Phe Ser Leu Val Lys Tyr Val
        515                 520                 525

Pro Leu Thr Tyr Asn Lys Val Tyr Arg Tyr Pro Asp Trp Ala Ile Gly
    530                 535                 540

Leu Gly Trp Gly Leu Ala Leu Ser Ser Met Val Cys Ile Pro Leu Val
545                 550                 555                 560

Ile Val Ile Leu Leu Cys Arg Thr Glu Gly Pro Leu Arg Val Arg Ile
                565                 570                 575

Lys Tyr Leu Ile Thr Pro Arg Glu Pro Asn Arg Trp Ala Val Glu Arg
            580                 585                 590

Glu Gly Ala Thr Pro Phe His Ser Arg Ala Thr Leu Met Asn Gly Ala
        595                 600                 605

Leu Met Lys Pro Ser His Val Ile Val Glu Thr Met Met
    610                 615                 620
```

<210> SEQ ID NO 23
<211> LENGTH: 1866
<212> TYPE: DNA
<213> ORGANISM: Mus musculus -continued

<400> SEQUENCE: 23
atggccacga aggagaagct gcaatgtctg aaagacttcc acaaagacat cctgaagcct 60
tctccaggga agagcccagg cacacggcct gaagatgagg cggacgggaa gccccctcag 120
agggagaagt ggtccagcaa gatcgacttt gtgctgtctg tggccggagg cttcgtgggt 180
ttgggcaacg tctggcgttt cccgtacctc tgctacaaaa atggtggagg tgcgttcctc 240
ataccgtatt ttattttcct gtttgggagc ggcctgcctg tgtttttctt ggaggtcatc 300
ataggccagt acacatcaga agggggcatc acctgctggg agaagatctg tcctttgttc 360
tctggcattg gctacgcatc catcgtcatt gtgtccctcc tgaacgtgta ctacatcgtc 420
atcctggcct gggccacata ctacctattc cactctttcc agaaggatct tccctgggcc 480
cactgcaacc atagctggaa cacaccacag tgcatggagg acaccctgcg taggaacgag 540
agtcactggg tctcccttag cactgccaac ttcacctcac ccgtcatcga gttctgggag 600
cgcaatgtgc tcagcctgtc ctccggaatc gacaacccag gcagtctgaa atgggacctc 660
gcgctctgcc tcctcttagt ctggctcgtc tgtttttctt gcatctggaa gggtgttcga 720
tccacaggca aggttgtcta cttcaccgct actttcccgt ttgccatgct tctggtgctg 780
ctggtccgtg gactgaccct gccaggtgct ggtgaaggca tcaaattcta cctgtaccct 840
gacatcagcc gccttgggga cccacaggtg tggatcgacg ctggaactca gatattcttt 900
tcctacgcaa tctgcctggg ggccatgacc tcactgggaa gctataacaa gtacaagtat 960
aactcgtaca gggactgtat gctgctggga tgcctgaaca gtggtaccag ttttgtgtct 1020
ggcttcgcaa ttttttccat cctgggcttc atggcacaag agcaaggggt ggacattgct 1080
gatgtggctg agtcaggtcc tggcttggcc ttcattgcct acccaaaagc tgtaaccatg 1140
atgccgctgc ccacctttgg gtctattctg tttttcatta tgctcctctt gcttggactg 1200
gacagccagt ttgttgaagt cgaaggacag atcacatcct tggttgatct ttacccgtcc 1260
ttcctaagga agggttatcg tcgggaaatc ttcatagcca tcttgtgtag catcagctac 1320
ctgctggggc tgacgatggt gacggagggt ggcatgtatg tgtttcaact ctttgactac 1380
tatgcagcta gtggtgtatg ccttttgtgg gttgcattct ttgaatgttt tgttattgcc 1440
tggatatatg gcggtgataa cttatatgac ggtattgagg acatgattgg ctatcggcct 1500
gggccctgga tgaagtacag ctgggctgtc atcactccag ctctttgtgt tggatgtttc 1560
gtcttctcgc ttgtcaagta tgtacccctg acctacaaca aagtgtaccg gtacccggat 1620
tgggcaattg ggctgggctg gggcctggcc ctttcctcca tgctgtgtat ccccttggtc 1680
attgtcatcc tcctctgccg gacggaggga ccgctccgcg tgagaatcaa atacctgata 1740
acccccaggg agcccaaccg ctgggctgtg gagcgtgaag ggccacaccc ctttcactcc 1800
cgagtaaccc tcatgaacgg cgcactcatg aaacccagtc acgtcattgt ggagaccatg 1860
atgtga 1866

<210> SEQ ID NO 24
<211> LENGTH: 621
<212> TYPE: PRT
<213> ORGANISM: Mus musculus

<400> SEQUENCE: 24

Met Ala Thr Lys Glu Lys Leu Gln Cys Leu Lys Asp Phe His Lys Asp
1 5 10 15

Ile Leu Lys Pro Ser Pro Gly Lys Ser Pro Gly Thr Arg Pro Glu Asp

-continued

```
            20                  25                  30

Glu Ala Asp Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Val Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Ile
        115                 120                 125

Val Ile Val Ser Leu Leu Asn Val Tyr Tyr Ile Val Ile Leu Ala Trp
    130                 135                 140

Ala Thr Tyr Tyr Leu Phe His Ser Phe Gln Lys Asp Leu Pro Trp Ala
145                 150                 155                 160

His Cys Asn His Ser Trp Asn Thr Pro Gln Cys Met Glu Asp Thr Leu
                165                 170                 175

Arg Arg Asn Glu Ser His Trp Val Ser Leu Ser Thr Ala Asn Phe Thr
            180                 185                 190

Ser Pro Val Ile Glu Phe Trp Glu Arg Asn Val Leu Ser Leu Ser Ser
        195                 200                 205

Gly Ile Asp Asn Pro Gly Ser Leu Lys Trp Asp Leu Ala Leu Cys Leu
    210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Glu
            260                 265                 270

Gly Ile Lys Phe Tyr Leu Tyr Pro Asp Ile Ser Arg Leu Gly Asp Pro
        275                 280                 285

Gln Val Trp Ile Asp Ala Gly Thr Gln Ile Phe Phe Ser Tyr Ala Ile
    290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Ile Phe Ser Ile Leu Gly Phe Met Ala
            340                 345                 350

Gln Glu Gln Gly Val Asp Ile Ala Asp Val Ala Glu Ser Gly Pro Gly
        355                 360                 365

Leu Ala Phe Ile Ala Tyr Pro Lys Ala Val Thr Met Met Pro Leu Pro
    370                 375                 380

Thr Phe Trp Ser Ile Leu Phe Phe Ile Met Leu Leu Leu Leu Gly Leu
385                 390                 395                 400

Asp Ser Gln Phe Val Glu Val Glu Gly Gln Ile Thr Ser Leu Val Asp
                405                 410                 415

Leu Tyr Pro Ser Phe Leu Arg Lys Gly Tyr Arg Arg Glu Ile Phe Ile
            420                 425                 430

Ala Ile Leu Cys Ser Ile Ser Tyr Leu Leu Gly Leu Thr Met Val Thr
        435                 440                 445
```

-continued

```
Glu Gly Gly Met Tyr Val Phe Gln Leu Phe Asp Tyr Tyr Ala Ala Ser
    450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
            500                 505                 510

Pro Ala Leu Cys Val Gly Cys Phe Val Phe Ser Leu Val Lys Tyr Val
        515                 520                 525

Pro Leu Thr Tyr Asn Lys Val Tyr Arg Tyr Pro Asp Trp Ala Ile Gly
    530                 535                 540

Leu Gly Trp Gly Leu Ala Leu Ser Ser Met Leu Cys Ile Pro Leu Val
545                 550                 555                 560

Ile Val Ile Leu Leu Cys Arg Thr Glu Gly Pro Leu Arg Val Arg Ile
                565                 570                 575

Lys Tyr Leu Ile Thr Pro Arg Glu Pro Asn Arg Trp Ala Val Glu Arg
            580                 585                 590

Glu Gly Ala Thr Pro Phe His Ser Arg Val Thr Leu Met Asn Gly Ala
        595                 600                 605

Leu Met Lys Pro Ser His Val Ile Val Glu Thr Met Met
    610                 615                 620
```

<210> SEQ ID NO 25
<211> LENGTH: 1863
<212> TYPE: DNA
<213> ORGANISM: Homo sapiens

<400> SEQUENCE: 25

```
atggccacca aggagaagct gcagtgtctg aaagatttcc acaaggacat cctgaagccc     60

tcaccaggga agagcccagg cacgcggcct gaggacgagg ctgagggaaa acctccgcag    120

agggagaagt ggtctagcaa gatcgacttt gtgctctctg tggctggcgg cttcgtgggc    180

ttgggcaacg tctggcgctt cccgtacctc tgctacaaga atggtggagg tgcgtttctc    240

ataccgtatt ttattttcct gtttgggagc ggcctgcctg tgtttttctt ggagatcatc    300

ataggccagt acacctctga agggggcatc acctgctggg aaaagatctg ccccttgttc    360

tctggtatcg gctatgcctc cgttgtaatt gtgtccctcc tgaatgtcta ctacatcgtc    420

atcctggcct gggccacata ctacctgttc cagtccttcc agaaggagct gccctgggca    480

cactgcaacc acagctggaa cacacctcac tgcatggagg acaccatgcg caagaacaag    540

agtgtctgga tcaccatcag ctccaccaac ttcacctccc ctgtcatcga gttctgggag    600

cgcaacgtgc tgagcttgtc ccctggaatc gaccacccag gctctctgaa atgggacctc    660

gctctctgcc ttcttttagt ctggctagtg tgtttcttct gcatctggaa gggcgtcagg    720

tccactggga aggtcgtcta cttcacagcc acttttccat tcgccatgct cctggtgctg    780

ctggtccgag ggctgacgct gccgggcgcg ggcgcaggca tcaagttcta tctgtatcct    840

gacatcaccc gccttgagga cccacaggtg tggattgacg ctgggactca gatattcttc    900

tcttatgcca tctgcctggg ggctatgacc tcgctgggga gctacaacaa gtacaagtat    960

aactcgtaca gggactgtat gctgctggga tgcctgaaca gtggtaccag ttttgtgtct   1020

ggcttcgcaa ttttttccat cctgggcttc atggcacaag agcaaggggt ggacattgct   1080

gatgtggctg agtcaggtcc tggcctggcc ttcattgcct acccaaaagc tgtgacaatg   1140
```

-continued atgccgctgc ccacattttg gtccattctt ttttttatta tgcttctctt gcttggactg 1200
gatagccagt ttgttgaagt tgaaggacag atcacatcct tggttgatct ttacccatcc 1260
ttcctaagga agggttatcg tcgggaaatc ttcatcgcct tcgtgtgtag catcagctac 1320
ctgctggggc tgacgatggt gacggagggt ggcatgtatg tgtttcagct ctttgactac 1380
tatgcagcta gcggtgtatg ccttttgtgg gttgcattct ttgaatgttt tgttattgcc 1440
tggatatatg gaggtgataa cctttatgat ggtattgagg acatgattgg ctatcggccc 1500
gggccctgga tgaagtacag ctgggctgtg atcactccag ttctctgtgt tggatgtttc 1560
atcttctcgc tcgtcaagta cgtacccctg acctacaaca aaacatacgt gtaccccaac 1620
tgggccattg ggctgggctg gagcctggcc ctttcctcca tgctctgcgt tcccttggtc 1680
atcgtcatcc gcctctgcca gactgagggg ccgttccttg tgagagtcaa gtacctgctg 1740
accccaaggg aacccaaccg ctgggctgtg gagcgcgagg gagccacacc ttacaactct 1800
cgcaccgtca tgaacggcgc tctcgtgaaa ccgacccaca tcattgtgga gaccatgatg 1860
tga 1863

<210> SEQ ID NO 26
<211> LENGTH: 620
<212> TYPE: PRT
<213> ORGANISM: Homo sapiens

<400> SEQUENCE: 26

Met Ala Thr Lys Glu Lys Leu Gln Cys Leu Lys Asp Phe His Lys Asp
1 5 10 15

Ile Leu Lys Pro Ser Pro Gly Lys Ser Pro Gly Thr Arg Pro Glu Asp
20 25 30

Glu Ala Glu Gly Lys Pro Pro Gln Arg Glu Lys Trp Ser Ser Lys Ile
35 40 45

Asp Phe Val Leu Ser Val Ala Gly Gly Phe Val Gly Leu Gly Asn Val
50 55 60

Trp Arg Phe Pro Tyr Leu Cys Tyr Lys Asn Gly Gly Gly Ala Phe Leu
65 70 75 80

Ile Pro Tyr Phe Ile Phe Leu Phe Gly Ser Gly Leu Pro Val Phe Phe
85 90 95

Leu Glu Ile Ile Ile Gly Gln Tyr Thr Ser Glu Gly Gly Ile Thr Cys
100 105 110

Trp Glu Lys Ile Cys Pro Leu Phe Ser Gly Ile Gly Tyr Ala Ser Val
115 120 125

Val Ile Val Ser Leu Leu Asn Val Tyr Tyr Ile Val Ile Leu Ala Trp
130 135 140

Ala Thr Tyr Tyr Leu Phe Gln Ser Phe Gln Lys Glu Leu Pro Trp Ala
145 150 155 160

His Cys Asn His Ser Trp Asn Thr Pro His Cys Met Glu Asp Thr Met
165 170 175

Arg Lys Asn Lys Ser Val Trp Ile Thr Ile Ser Ser Thr Asn Phe Thr
180 185 190

Ser Pro Val Ile Glu Phe Trp Glu Arg Asn Val Leu Ser Leu Ser Pro
195 200 205

Gly Ile Asp His Pro Gly Ser Leu Lys Trp Asp Leu Ala Leu Cys Leu
210 215 220

Leu Leu Val Trp Leu Val Cys Phe Phe Cys Ile Trp Lys Gly Val Arg
225 230 235 240

-continued

```
Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Ala
            260                 265                 270

Gly Ile Lys Phe Tyr Leu Tyr Pro Asp Ile Thr Arg Leu Glu Asp Pro
        275                 280                 285

Gln Val Trp Ile Asp Ala Gly Thr Gln Ile Phe Phe Ser Tyr Ala Ile
    290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Ile Phe Ser Ile Leu Gly Phe Met Ala
            340                 345                 350

Gln Glu Gln Gly Val Asp Ile Ala Asp Val Ala Glu Ser Gly Pro Gly
        355                 360                 365

Leu Ala Phe Ile Ala Tyr Pro Lys Ala Val Thr Met Met Pro Leu Pro
    370                 375                 380

Thr Phe Trp Ser Ile Leu Phe Phe Ile Met Leu Leu Leu Leu Gly Leu
385                 390                 395                 400

Asp Ser Gln Phe Val Glu Val Glu Gly Gln Ile Thr Ser Leu Val Asp
                405                 410                 415

Leu Tyr Pro Ser Phe Leu Arg Lys Gly Tyr Arg Arg Glu Ile Phe Ile
            420                 425                 430

Ala Phe Val Cys Ser Ile Ser Tyr Leu Leu Gly Leu Thr Met Val Thr
        435                 440                 445

Glu Gly Gly Met Tyr Val Phe Gln Leu Phe Asp Tyr Tyr Ala Ala Ser
    450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
            500                 505                 510

Pro Val Leu Cys Val Gly Cys Phe Ile Phe Ser Leu Val Lys Tyr Val
        515                 520                 525

Pro Leu Thr Tyr Asn Lys Thr Tyr Val Tyr Pro Asn Trp Ala Ile Gly
    530                 535                 540

Leu Gly Trp Ser Leu Ala Leu Ser Ser Met Leu Cys Val Pro Leu Val
545                 550                 555                 560

Ile Val Ile Arg Leu Cys Gln Thr Glu Gly Pro Phe Leu Val Arg Val
                565                 570                 575

Lys Tyr Leu Leu Thr Pro Arg Glu Pro Asn Arg Trp Ala Val Glu Arg
            580                 585                 590

Glu Gly Ala Thr Pro Tyr Asn Ser Arg Thr Val Met Asn Gly Ala Leu
        595                 600                 605

Val Lys Pro Thr His Ile Ile Val Glu Thr Met Met
    610                 615                 620
```